US012673043B2

(12) United States Patent
Longaker et al.

(10) Patent No.: US 12,673,043 B2
(45) Date of Patent: Jul. 7, 2026

(54) USE OF INHIBITORS OF THE ACTIVATOR PROTEIN 1 (AP-1) FOR PREVENTING ADHESIONS

(71) Applicant: The Board of Trustees of the Leland Stanford Junior University, Stanford, CA (US)

(72) Inventors: Michael T. Longaker, Atherton, CA (US); Gerlinde Wernig, Woodside, CA (US); Jeffrey A. Norton, Redwood City, CA (US); Geoffrey Gurtner, Portola Valley, CA (US); Michael Januszyk, Daly City, CA (US); Deshka Foster, San Bruno, CA (US); Malini Chinta, Redwood City, CA (US)

(73) Assignee: The Board of Trustees of the Leland Stanford Junior University

( * ) Notice: Subject to any disclaimer, the term of this patent is extended or adjusted under 35 U.S.C. 154(b) by 717 days.

(21) Appl. No.: 18/009,637

(22) PCT Filed: Jun. 17, 2021

(86) PCT No.: PCT/US2021/037910
§ 371 (c)(1),
(2) Date: Dec. 9, 2022

(87) PCT Pub. No.: WO2021/257887
PCT Pub. Date: Dec. 23, 2021

(65) Prior Publication Data
US 2023/0241035 A1 Aug. 3, 2023

Related U.S. Application Data

(60) Provisional application No. 63/041,458, filed on Jun. 19, 2020.

(51) Int. Cl.
*A61K 31/423* (2006.01)
*A61P 41/00* (2006.01)

(52) U.S. Cl.
CPC ............ *A61K 31/423* (2013.01); *A61P 41/00* (2018.01)

(58) Field of Classification Search
CPC ............................. A61K 31/423; A61P 41/00
See application file for complete search history.

(56) References Cited

U.S. PATENT DOCUMENTS 6,689,803 B2 2/2004 Hunter
8,093,289 B2 1/2012 Kakuda et al.
8,945,537 B2 2/2015 Turzi

OTHER PUBLICATIONS

Makino, H., Seki, S., Yahara, Y. et al. A selective inhibition of c-Fos/activator protein-1 as a potential therapeutic target for intervertebral disc degeneration and associated pain. Sci Rep 7, 16983 (2017). https://doi.org/10.1038/s41598-017-17289-y.*
Balli et al. (2019) "Activator Protein-1 Transcriptional Activity Drives Soluble Micrograft-Mediated Cell Migration and Promotes the Matrix Remodeling Machinery", Stem Cells International vol. 2019, Article ID 6461580.
Foster et al. (2020) "Elucidating the fundamental fibrotic processes driving abdominal adhesion formation", Nature Communications vol. 11, Article No. 4061.

* cited by examiner

*Primary Examiner* — Alicia L Otton
(74) *Attorney, Agent, or Firm* — Pamela J. Sherwood; Bozicevic, Field & Francis LLP

(57) ABSTRACT

Aspects of the present disclosure include methods of treating a subject to reduce adhesion formation.

10 Claims, 49 Drawing Sheets

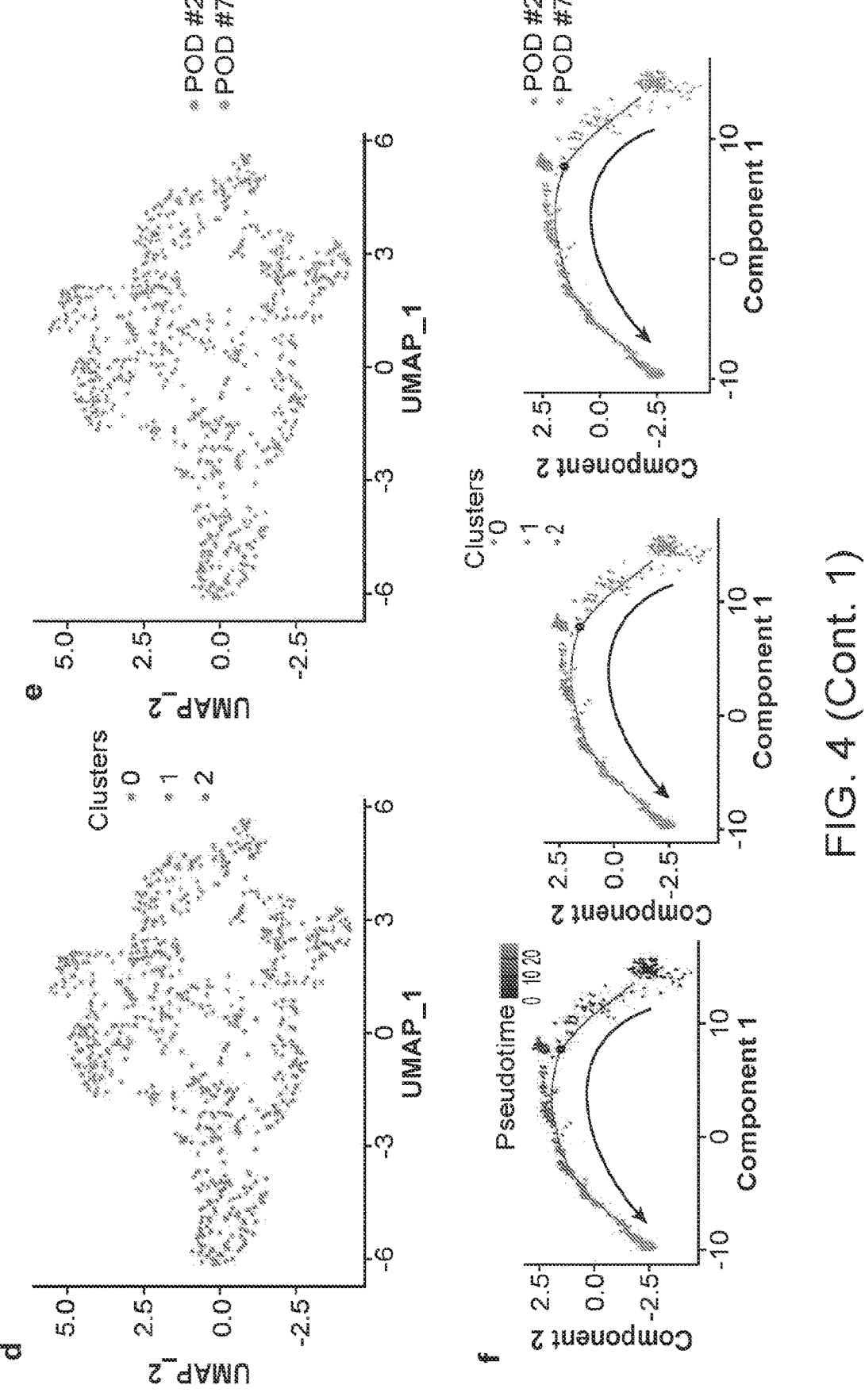
FIG. 4 (Cont. 1)

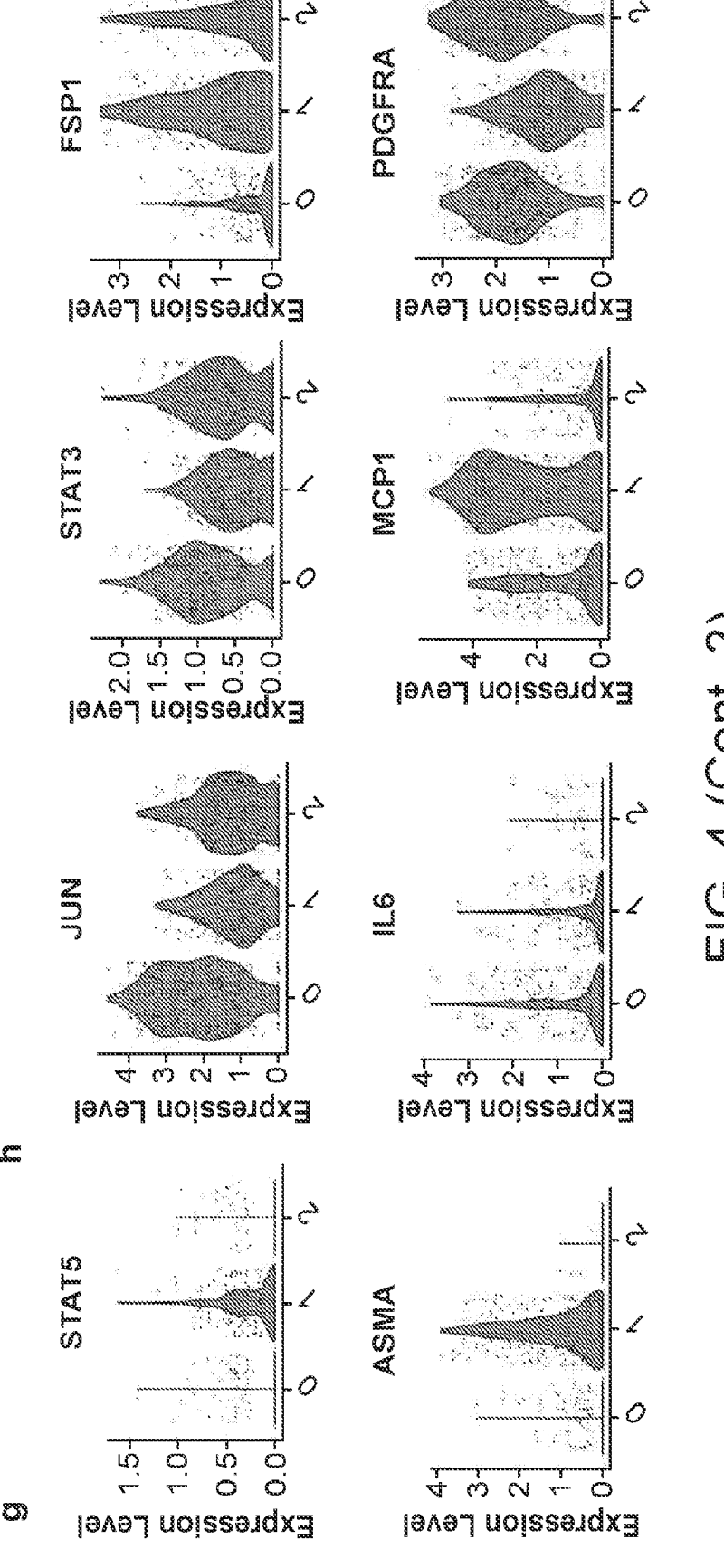
FIG. 4 (Cont. 2)

FIG. 5

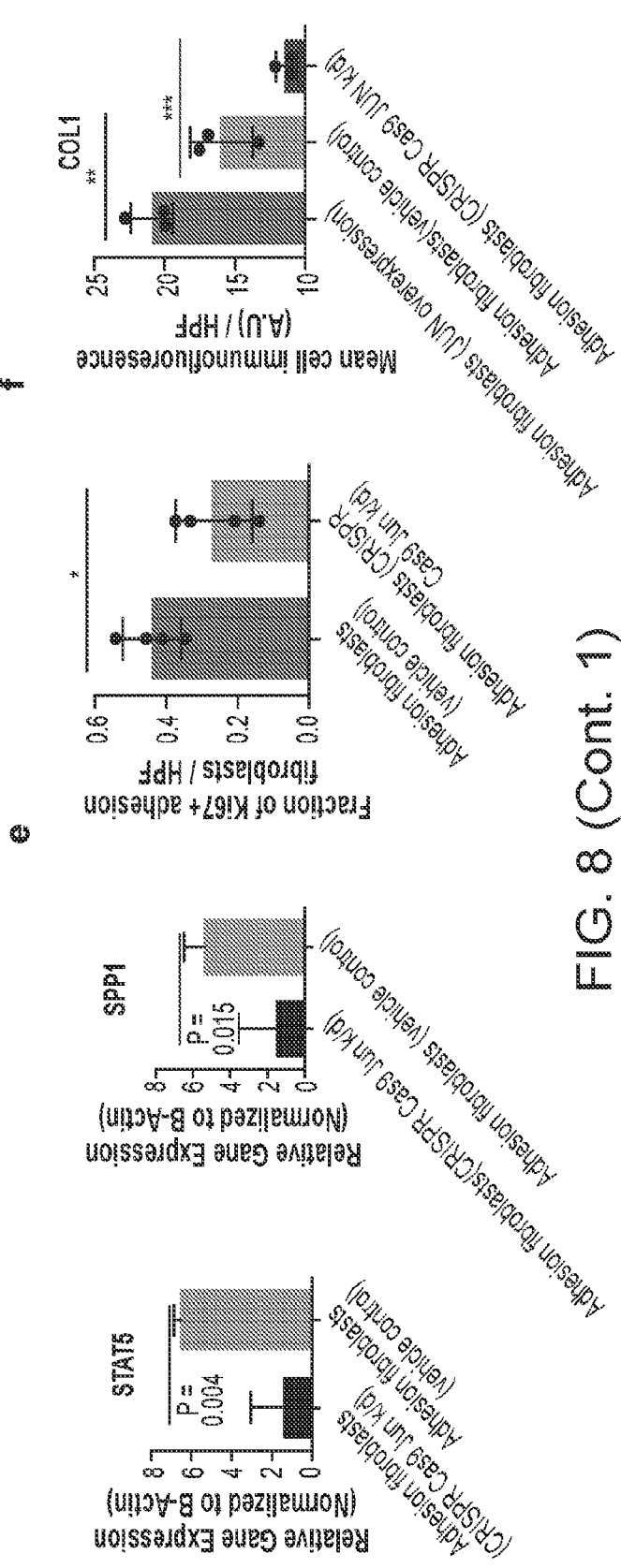
FIG. 8 (Cont. 1)

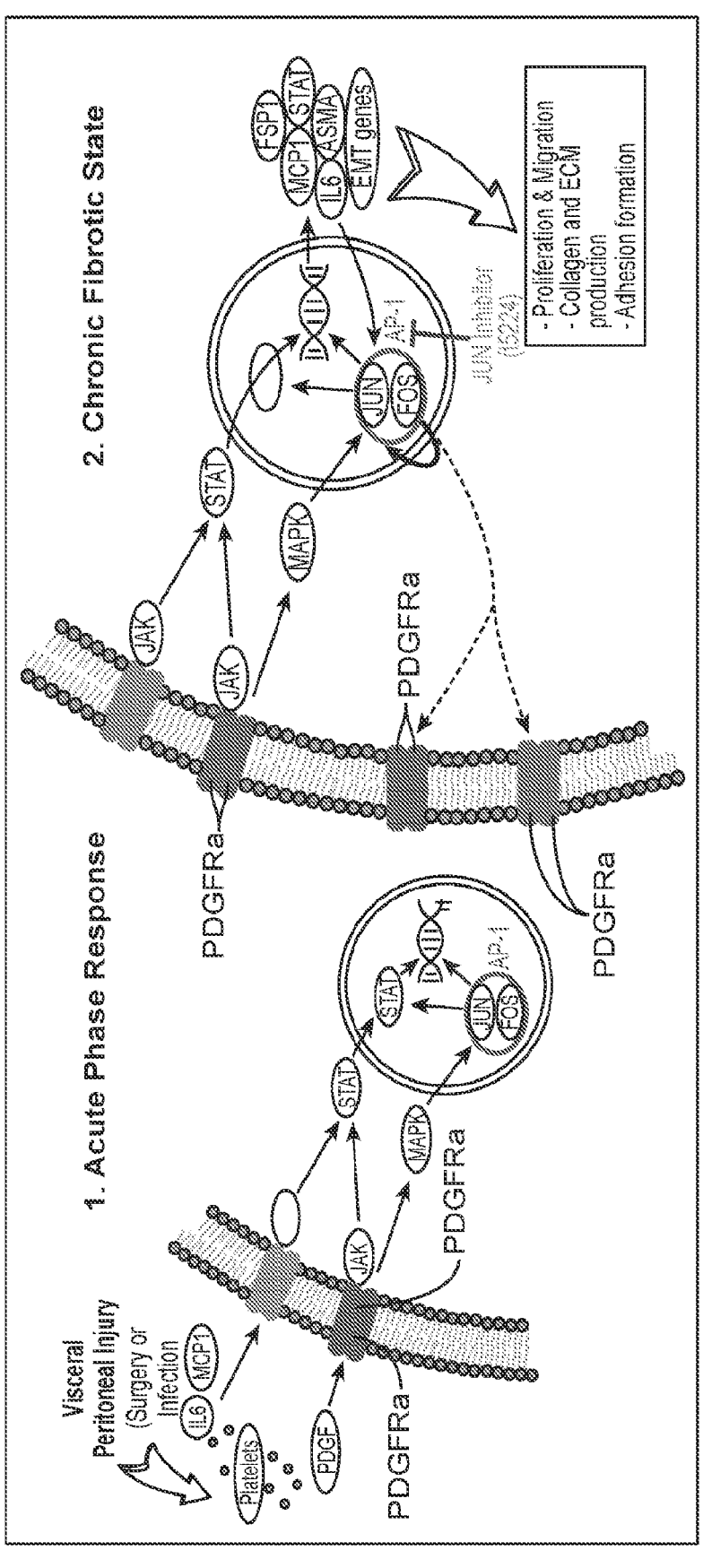
FIG. 8 (Cont. 2)

Mouse adhension fibroblast bulk RNA-seq GSEA and GO analysis a b a          Mouse abdominal adhesion tissues express JUN
early and related pathways are activated b Images of human abdominal adhesions specimens Characterization of human abdominal adhesion fibroblasts marker Human adhesion fibroblast RNA-seq GSEA and Go Analysis a b a b
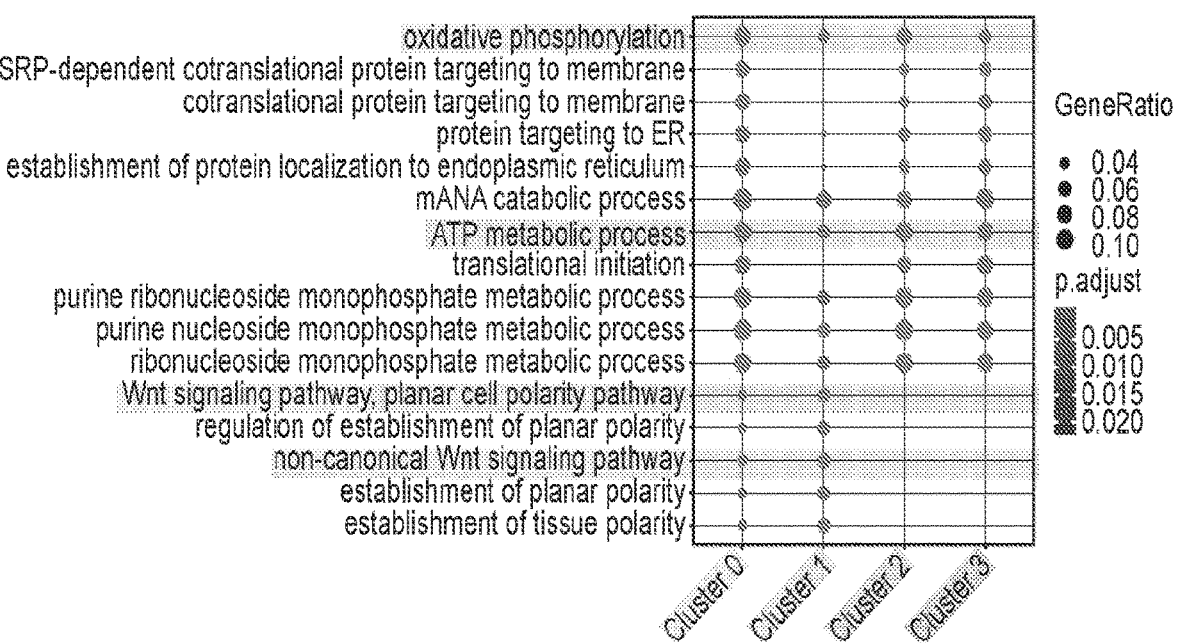
FIG. 28 (Cont. 1)

c
FIG. 28 (Cont. 2)

USE OF INHIBITORS OF THE ACTIVATOR PROTEIN 1 (AP-1) FOR PREVENTING ADHESIONS

CROSS REFERENCE TO RELATED APPLICATIONS

The present application claims the benefit of and priority to U.S. Provisional Patent Application No. 63/041,458 filed Jun. 19, 2020, the entire disclosure of which is hereby incorporated by reference herein in its entireties for all purposes.

STATEMENT REGARDING FEDERALLY SPONSORED RESEARCH

This invention was made with Government support under contract GM116892 awarded by the National Institutes of Health. The Government has certain rights in the invention.

BACKGROUND OF THE INVENTION

Adhesions are fibrotic scars that form between abdominal organs following surgery or infection, and cause bowel obstruction, chronic pain, or infertility. Adhesions occur post-operatively in 50-90% of all open abdominal operations and as such, represent an enormous clinical problem impacting hundreds of millions of patients worldwide. There are essentially no available treatments that prevent adhesions.

The present disclosure provides insights into the molecular and genetic mechanisms of adhesion formation and provides therapeutic prevention and treatments based on these findings.

SUMMARY OF THE INVENTION

Methods are provided for the treatment and prevention of fibrosis, e.g. abdominal adhesions. In some embodiments an individual at risk of abdominal adhesion formation is treated with a small molecule inhibitor of the Activator Protein 1 (AP-1) transcription factor complex. In some embodiments the small molecule inhibitor of AP-1 is T-5224 (3-[5-(4-Cyclopentyloxy-2-hydroxybenzoyl)-2-[(3-oxo-1,2-benzo-xazol-6-yl)methoxy]phenyl]propanoic acid) or a derivative thereof, including prodrugs, salts, analogs, and the like. In some embodiments the inhibitor is applied locally, e.g. at the site of surgery that can predispose to adhesion formation.

The AP-1 inhibitor is administered at an effective dose for inhibition of fibrosis. In some embodiments, the AP-1 inhibitor, alone or in combination with an additional active agent, is administered to a local site for inhibition of fibrosis in a drug delivery device, including without limitation a biodegradable implant. In some embodiments the AP-1 inhibitor is provided in a particulate form for sustained release. In some embodiments the particulate form is a biodegradable nanoparticle or microparticle, which may include, without limitation, PLGA particles. In other embodiments the particulate form is a liposomal particle. In other embodiments the AP-1 inhibitor is provided as an implant for sustained release, including without limitation PLGA implants, a biocompatible matrix, e.g. a hydrogel, etc.

In some embodiments the effective unit dose of a AP-1 inhibitor is from about 1 μg to about 100 mg or more. For delivery to a human, the dose may be from about 1 μg, 10 μg, from about 25 μg, from about 50 μg, from about 100 μg, up to about 50 mg, up to about 25 mg, up to about 10 mg, up to about 5 mg, up to about 1 mg, up to about 10 mg, up to about 50 mg, up to about 100 mg, or more.

The inhibitor may be administered immediately following an injury, such as surgery, etc., or within 1 hour, within 2 hours, within 4 hours, within 6 hours, within 12 hours, within 1 day, within 2 days, within 3 days. The inhibitor is optionally formulated in a particulate form. The drug delivery device is optionally a biodegradable matrix, e.g. a hydrogel, that does not need to be removed. The surgical site is closed, and function may be assessed after about 1 week, after about 2 weeks, after about 3 weeks, after about 4 week, after about 6 weeks, after about 8 weeks, or more, as needed, and may be assessed at multiple time points.

Without being limited by the theory, it is believed that c-Jun expression is upregulated in abdominal adhesion fibroblasts. Application of an AP-1 inhibitor, e.g. T-5224, inhibits c-JUN and related profibrotic signaling in adhesion fibroblasts thereby reducing fibrosis. In particular, topical application of the inhibitor inhibits adhesion formation in vivo.

In certain embodiments, the present disclosure provides methods of treating a subject to prevent or reduce adhesion formation, the method comprising administering to a subject in need of thereof a small molecule that that inhibits AP-1, including without limitation T-5224 (3-[5-(4-Cyclopentyloxy-2-hydroxybenzoyl)-2-[(3-oxo-1,2-benzoxazol-6-yl)methoxy]phenyl]propanoic acid).

These and other objects, advantages, and features of the invention will become apparent to those persons skilled in the art upon reading the details of the subject methods and compositions as more fully described below.

DEFINITIONS

Figure 1:
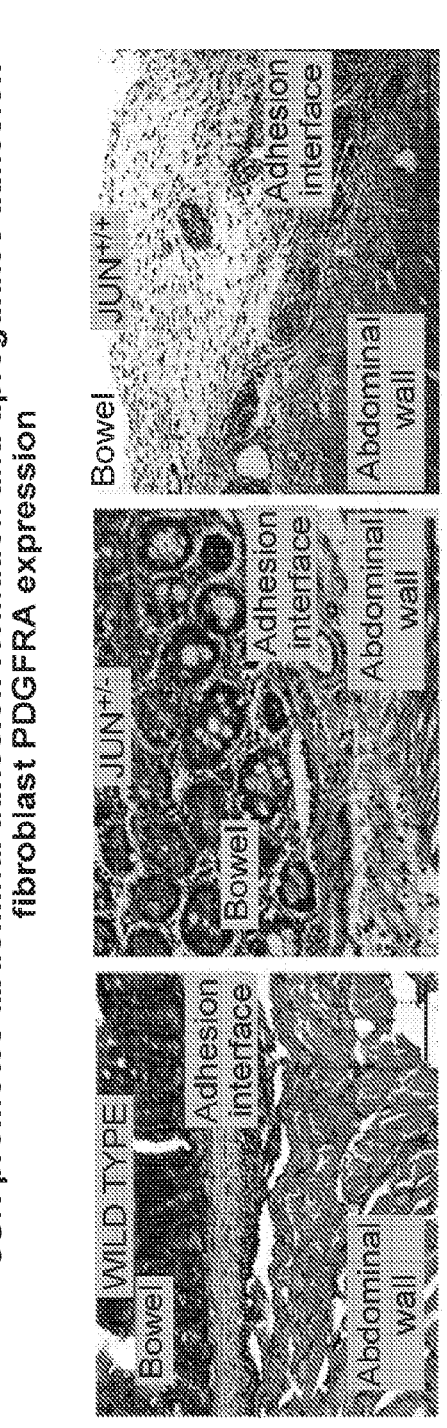
FIG. 1. JUN promotes abdominal adhesion formation and upregulates adhesion fibroblast PDGFRA expression a, Representative samples of hematoxylin and eosin (H&E) stained abdominal adhesion tissue specimen from $JUN^{+/+}$ (right panel), $JUN^{+/-}$ (middle panel) and wild-type mice (left panel). Green dotted lines outline adhesion interface, structures as labeled in figure. n=10. Scale bars, 100 μm. b, Application of an objective histologic adhesion rating score by blinded pathologists (based on to the gross score used by Tsai et al. (2018) and the histologic score used by Linsky et al., (1987)) quantifies relative adhesion severity in wild-type, $JUN^{+/-}$, and $JUN^{+/+}$ mouse specimens. n=10. c, Schematic of the $PDGFRA^{GFP}$ mouse construct. d, Fluorescent imaging of $PDGFRA^{GFP}$ mouse uninjured (control) visceral and parietal peritoneum. Structures as labelled in figure, white dotted lines outline area of potential adhesion interface, POD=post-operative day. n=5. Scale bar, 100 um. e, Fluorescent imaging of $PDGFRA^{GFP}$ mouse adhesion tissue at POD 7 (top panel), POD 14 (middle panel—visceral-parietal adhesion, bottom panel—visceral-visceral adhesion); Structures as labelled in figure, white dotted lines outline adhesion interface. n=5. Scale bars, 100 um. f, Quantitation of GFP+ ($PDGFRA^{GFP}$) cells per high power field (HPF) in the adhesion interface in mouse adhesions (from FIG. 1d-e). n=5. g, Immunofluorescent staining of representative samples shows PDGFRA and phospho (p)-JUN co-localization (left panels) and independent expression (right panels) within the adhesion interface. Individual panels at top, merge in bottom row, white dotted lines highlight cells of interest. Scale bars, 25 μm. Data and error bars represent means±standard deviation (SD). *P=0.0001 (one-way Anova), **P=0.0001 (one-way Anova).
Figure 1:
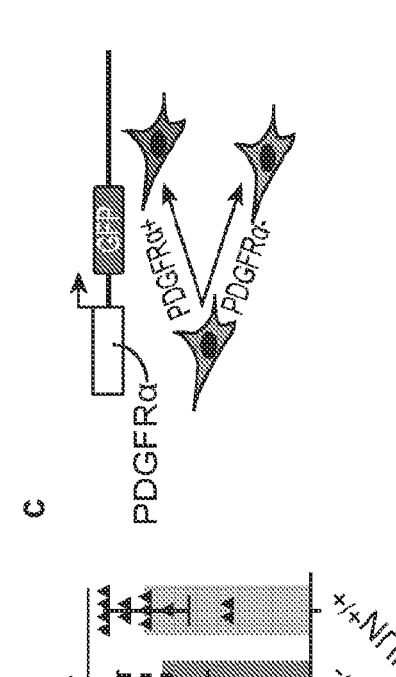
Figure 1:
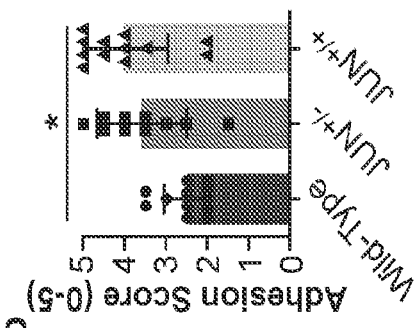
Figure 1:
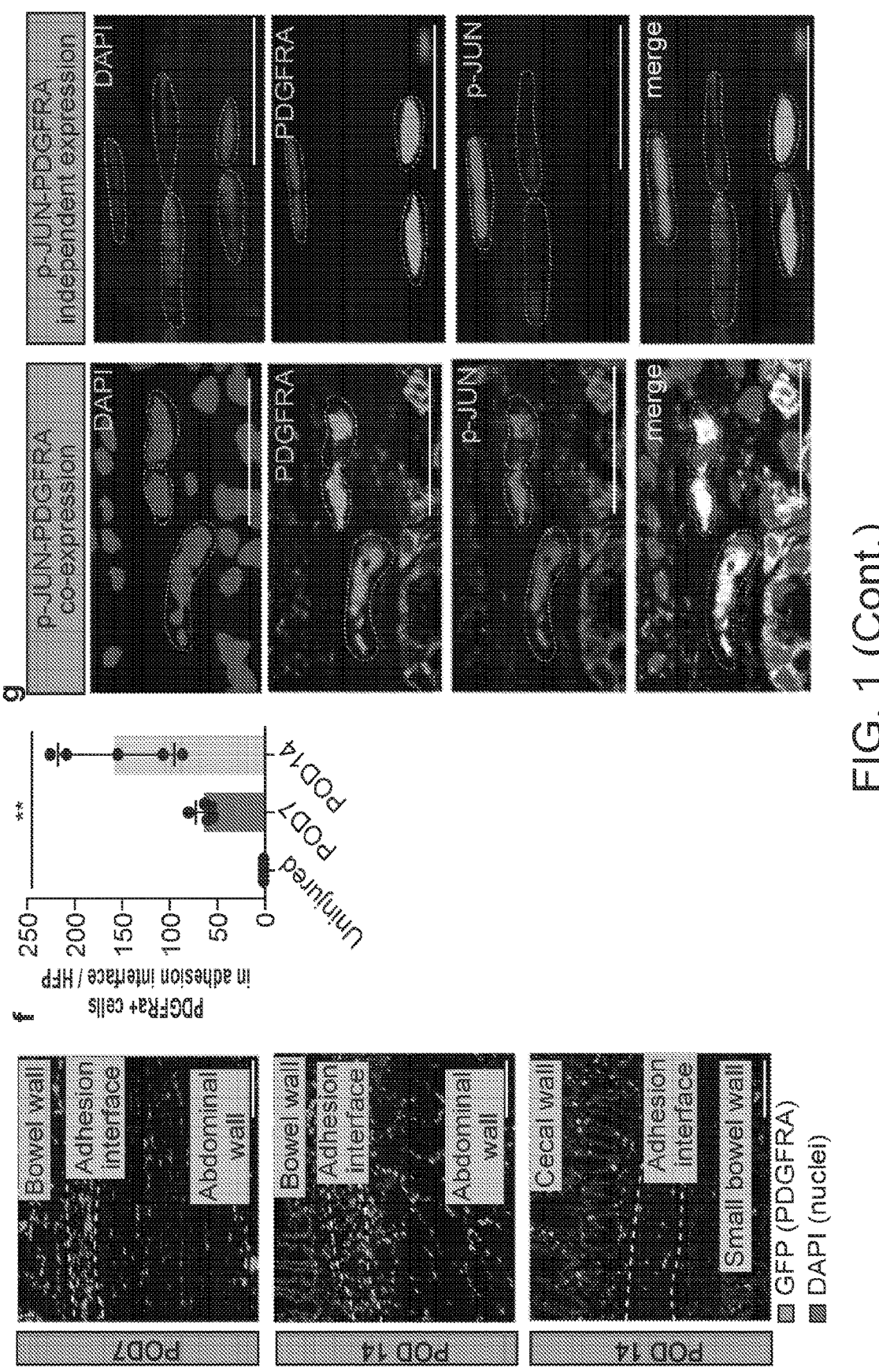

In the description that follows, a number of terms conventionally used in the field of cell culture are utilized. In order to provide a clear and consistent understanding of the specification and claims, and the scope to be given to such terms, the following definitions are provided.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clon-Tech.

The term "therapeutic agent" as used herein includes one or more "therapeutic agents" or "drugs." The terms "therapeutic agents" or "drugs" can be used interchangeably herein and include pharmaceutically active compounds. Examples include, without limitation: antibiotics, small molecules, proteins or polypeptides, polynucleotides, nucleic acids, oligonucleotides, ribozymes, anti-sense oligonucleotides, gene/vector systems, antisense nucleic acid (RNA or DNA), virus vectors or vectors derived from viral sources, antibodies, receptor antagonists, transcriptional repressors, etc. Polynucleotides can code for therapeutic proteins or polypeptides.

"Polynucleotide" or "oligonucleotide" is used interchangeably and each means a linear polymer of nucleotide monomers, e.g., deoxyribonucleotides and/or ribonucleotides.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. An amino acid analog refers to a compound that has the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having or at risk of having an adhesion. Subjects may be human, but also include other mammals, particularly those mammals useful as laboratory models for human disease, e.g. mouse, rat, etc.

Anti-AP-1 agent. c-Jun is a protein that combines with c-Fos to form the AP-1 early response transcription factor, which functions in regulating gene expression for differentiation, cell cycle progression, proliferation, apoptosis, extracellular matrix production, and other cellular processes. As used herein, the term "anti-AP1 agent" or refers to an agent that inhibits activity of the AP-1 complex. In some embodiments the agent is T-5224 (3-[5-(4-Cyclopentyloxy-2-hydroxybenzoyl)-2-[(3-oxo-1,2-benzoxazol-6-yl) methoxy]phenyl]propanoic acid) or a derivative or mimetic thereof, including prodrugs, salts, analogs, and the like.

The definition of an appropriate patient sample encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents; washed; or enrichment for certain cell populations. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's sample cell, e.g., a sample comprising polynucleotides and/or polypeptides that is obtained from a patient's sample cell (e.g., a cell lysate or other cell extract comprising polynucleotides and/or polypeptides); and a sample comprising sample cells from a patient. A biological sample comprising a sample cell from a patient can also include normal, non-diseased cells.

The term "diagnosis" is used herein to refer to the identification of a molecular or pathological state, disease, or condition, such as the identification of fibrosis.

Adhesions are fibrotic scars that form between abdominal organs following surgery or infection, and may cause bowel obstruction, chronic pain, or infertility. Adhesions are believed to derive primarily from the visceral peritoneum, and are formed by poly-clonal proliferating tissue-resident fibroblasts. A therapy that can be applied intra-operatively or post-operatively to prevent adhesion formation could dramatically improve the lives of surgical patients. Adhesions form postoperatively in 50-90% of all open abdominal operations and as such, represent an enormous clinical problem impacting hundreds of millions of patients each year.

Fibrosis is the excessive accumulation of extracellular matrix components (ECM) in and around inflamed or damaged tissue, often associated with chronic inflammation or cancer, which forms adhesions. The presence of fibrosis can be detected by means known in the art, for example by examination of tissue for excess scarring. Prior to fibrosis, an individual may be determined to be susceptible based on a tissue injury (such as surgery), and/or an undesirable increase in inflammatory mediators that can exacerbate tissue injury, such as IL-1β, TNF-α and reactive oxygen and nitrogen species. Profibrotic mediators such as TGF-β1 may be present. Also present are activated fibroblasts (also known as myofibroblasts), which may be resistant to induction of apoptosis.

Exemplary forms of fibrosis include, but are not limited to, tumor fibrosis, cardiac fibrosis, liver fibrosis, kidney and bladder fibrosis, lung fibrosis, dermal scarring and keloids, wound healing, abdominal and pleural adhesions, post-irradiation fibrosis, fibrosis related to chronic graft v host disease (GvHD), and Alzheimer's disease. In still further embodiments, cardiac fibrosis is associated with hypertension, hypertensive heart disease (HHD), myocardial infarction (MI), cardiac scarring related to ischemia congestive heart failure, cardiomyopathy, post-myocardial infarction defects in heart function, atherosclerosis, and restenosis. Kidney fibrosis may include, but not be limited to, diabetic nephropathy, vesicoureteral reflux, tubulointerstitial renal fibrosis, glomerulonephritis or glomerular nephritis (GN), focal segmental glomerulosclerosis, membranous glomerulonephritis, or mesangiocapillary GN. Liver fibrosis may include, but not be limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, autoimmune hepatitis). Lung fibrosis may include idiopathic pulmonary fibrosis (IPF) or cryptogenic fibrosing alveolitis, chronic fibrosing interstitial pneumonia, interstitial lung disease (ILD), and diffuse parenchymal lung disease (DPLD)), lung scarring including without limitation damage from bacterial viral or fungal infection, emphysema, chronic obstructive pulmonary disease (COPD); and chronic asthma may also be prevented, treated, or ameliorated with compositions of described herein. Also included is fibrosis of the eye and lens, for example glaucoma; age-related macular degeneration (wet AMD and dry AMD), fibrosis of the lens, periorbital fibrosis as in IgG4-related disease, hyperthyroidism, etc.

In an embodiment of the invention the fibrosis is abdominal adhesion fibrosis.

The methods of the invention may further comprise analysis of fibrosis or fibrotic activity following treatment according to the methods as claimed. Analysis of fibrosis may be made by obtaining a biological sample and examining molecular or pathological state, disease or condition, and the like.

As used herein, the terms "treatment," "treating," and the like, refer to administering an agent, or carrying out a procedure, for the purposes of obtaining an effect in a subject (e.g., a patient). The effect may be prophylactic in terms of completely or partially preventing an undesirable condition, disease or symptom thereof and/or may be therapeutic in terms of effecting a partial or complete remedy, remission, or cure for an undesirable condition, disease and/or symptoms of the disease. Treating thus encompasses the dinistration of an agent before an undesirable condition, disease or symptom thereof occurs, during the development of an undesirable condition, disease or symptom thereof, and/or after an undesirable condition, disease or symptom thereof has occurred. Treating may refer to any indicia of success in the treatment or amelioration or prevention of an undesirable condition or disease, including any objective or subjective parameter such as abatement; remission; diminishing of symptoms or making the undesirable condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present disclosure to prevent or delay, to alleviate, or to arrest or inhibit development of the symptoms or undesirable condition. The term "therapeutic effect" refers to the reduction, elimination, or prevention of the undesirable condition, disease, or symptoms or side effects of thereof.

"In combination with", "combination therapy" and "combination products" refer, in certain embodiments, to the concurrent administration to a patient of a first therapeutic and a second therapeutic. When administered in combination, each component can be administered at the same time or sequentially in any order at different points in time. Thus, each component can be administered separately but sufficiently closely in time so as to provide the desired therapeutic effect.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject, is sufficient to effect treatment of an undesirable condition, symptom, or disease of the subject. The effective dose is sufficient to reduce adhesions by at least about 10%, at least about 20%, at least about 30%, at least about 40%, at least about 50%, at least about 60%, at least about 70%, at least about 80%, at least about 90%, or more. The dose of an AP-1 inhibitor, for example, may be from about 0.01 mg/kg body weight to about 100 mg/kg body weight, and may be administered immediately following surgery or other event expected to result in adhesion formation; or for reducing existing adhesions. Dosing may be repeated daily, every 2 days, every 3 days, semi-weekly, weekly, etc.

Nanoparticles and microparticles. Polymer-encapsulated or conjugated drugs provide enhanced activity by protecting agents from degradation, targeting delivery to the desired site, ensuring combined agents are delivered, etc. Particulate formulations provide for a longer biological half-life and improved efficacy with reduced systemic side effects. Polymers of interest are biodegradable polymers, including without limitation lactic acid polymers (PLA), glycolic acid polymers (PLG) and poly(lactic-co-glycolic acid) (PLGA). Active agents can be encapsulated in the nanoparticles.

Oil-water (single) or water-oil-water (double) emulsion is one method by which polymers can be used to encapsulate active in micro- or nano-scale form. The polymer is dissolved into an organic phase (oil) that is emulsified with a surfactant or stabilizer (water). Hydrophobic drugs are added directly to the oil phase, whereas hydrophilic drugs (water) may be first emulsified with the polymer solution prior to formation of particles. High intensity sonication bursts facilitate the formation of small polymer droplets. The resulting emulsion is added to a larger aqueous phase and stirred for several hours, which allows the solvent to evaporate. Hardened nanoparticles are collected and washed by centrifugation.

The concentration of polymer will usually be at least about 0.01 mg/ml, more usually at least about 0.1 mg/ml, at least about 1 mg/ml, and not more than about 100 mg/ml, usually not more than about 50 mg/ml. The ratio of active agents to polymer as a weight percent will vary, from around about 1:1000; 1:500; 1:100, 1:50; 1:10; 1:5, and the like.

Solvents of interest are organic solvents, including, without limitation, dichloromethane (DCM), chloroform (CHF), tetrahydrofuran (THF), ethyl acetate, etc. The solvent solution with nucleic acid and polymer is dropped or injected at a set flow rate into a vessel filled with a miscible non-solvent. Flow rate may be optimized for each nucleic acid/polymer/solvent system. The selection is based on the desired yield and particle size. Miscible non-solvents for nanoprecipitation include, without limitation, ethanol, methanol, butanol etc.

Generally a temperature selected to maintain the stability of the active agent, and is usually not more than about 100° C., more usually not more than about 80° C., and may be not more than about 40° C., 30° C., or 20° C. It is desirable to keep the temperature below the glass transition temperature of the polymer, which typically ranges from 45-65° C., e.g. for PLGA. Therefore in some embodiments a temperature of around about 40° C. is used to advantage.

The particulates may have a controlled size, as appropriate for optimization of delivery of the biologically active agents. Usually the particle will have a diameter of from about about 50 nm, from about 100 nm, up to about 250 nm, up to about 500 nm, up to about 1 µm, up to about 2.5 µm, up to about 5 µm, and not more than about 10 m in diameter. In some embodiments the nanoparticle size is from about 100 nm to about 5 m in diameter, for example from about 100 nm to about 300 nm, from about 300 nm to about 2 µm, and the like. The particles optionally has a defined size range, which may be substantially homogeneous, where the variability may not be more than 100%, 50%, or 10% of the diameter. The sizes of particles can be altering by varying parameters, including the payload, the hydrophobicity of polymer, the type of organic solvent, organic solvent volume, solvent to polymer ratio, emulsifier, sonication intensity, centrifugation speed and time, and the like. See, for example, McCall, R. L., Sirianni, R. W. PLGA Nanoparticles Formed by Single- or Double-emulsion with Vitamin E-TPGS. *J. Vis. Exp.* (82), e51015, doi:10.3791/51015 (2013).

The particles may comprise a coating of any biologically compatible polymer. Some examples of biodegradable polymers useful as coating include hydroxyaliphatic carboxylic acids, either homo- or copolymers, such as poly(lactic acid), poly(glycolic acid), Poly(dl-lactide/glycolide, poly(ethylene glycol); polysaccharides, e.g. lectins, glycosaminoglycans, e.g. chitosan; celluloses, acrylate polymers, and the like. The selection of coating may be determined by the desired rate of degradation after administration, by targeting to a desired tissue, by protection from oxidation, and the like.

In some specific embodiments, the particles comprise a coating of polyethylene glycol, which may be conjugated to a polymer used to form the nanoparticle, or may be conjugated to the nanoparticle after it is formed. In some embodiments the coating is polyethylene glycol (PEG) at a molecular weight of from about 1000, from about 2000, from about 5000, up to about 20,000, up to about 15,000, up to about 10,000.

The particles of the invention may be incorporated in a pharmaceutical formulation. Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

Drug delivery devices include structures that can be implanted and that release the active agents, e.g. a AP-1 inhibitor at the targeted site. Implanted devices include spray formulations that may, for example, provide a coating on the inner abdominal surface. Implantable drug delivery devices can be broadly classified in two main groups: passive implants and active implants. The first group includes two main types of implants: biodegradable and non-biodegradable implants. Active systems rely on energy dependent methods that provide the driving force to control drug release. The second group includes devices such as osmotic pressure gradients and electromechanical drives.

Passive Polymeric Implants are normally relatively simple devices with no moving parts, they rely on passive diffusion for drug release. They are generally made of drugs packed within a biocompatible polymer molecule. Several parameters such as: drug type/concentration, polymer type, implant design and surface properties can be modified to control the release profile. Passive implants can be classified in two main categories: non-biodegradable and biodegradable systems.

Non-biodegradable implants are commonly prepared using polymers such as silicones, poly(urethanes), poly(acrylates) or copolymers such as poly(ethyelene vinyl acetate). Poly(ethylene-vinyl acetate) (PEVA) is a thermoplastic copolymer of ethylene and vinyl acetate. Poly(siloxanes) or silicones are organosilicon polymeric materials composed of silicon and oxygen atoms. Lateral groups can be methyl, vinyl or phenyl groups. These groups will influence the properties of the polymer. Poly(siloxanes) have been extensively used in medicine due to the unique combination of thermal stability, biocompatibility, chemical inertness and elastomeric properties. The silicones commonly used for medical devices are vulcanised at room temperature. They are prepared using a two-component poly(dimethylsiloxanes) (PDMS) in the presence of a catalyst (platinum based compound). The final material is formed via an addition hydrosilation reaction. An alternative method to obtain silicones for medical applications is the using linear PDMS with hydroxyl terminal groups. This linear polymer is cross-linked with low molecular weight tetra(alkyloxysilane) using stannous octoate catalyst.

This type of device can be monolithic or reservoir type implant. Monolithic type implants are made from a polymer matrix in which the drug is homogeneously dispersed. On the other hand, reservoir-type implants contain a compact drug core covered by a permeable non-biodegradable membrane. The membrane thickness and the permeability of the drug through the membrane will govern the release kinetics.

Biodegradable implants are made using polymers or block copolymers that can be broken down into smaller fragments that will be subsequently excreted or absorbed by the body. Normally they are made using polymers such as collagen, PEG, chitin, poly(caprolactone) (PCL), poly(lactic acid) (PLA) or poly(lactic-co-glycolic acid) (PLGA). Numerous other biodegradable polymers for drug delivery exist including: poly(amides), poly(anhydrides), poly(phosphazenes) and poly(dioxanone). Poly(anhydrides) have a low hydrolytic stability resulting in rapid degradation rates, making them suitable for use in short-term controlled delivery systems. Poly(phosphazenes) have a degradation rate that can be finely tuned by appropriate substitution with specific chemical groups and use of these polymers has been investigated for skeletal tissue regeneration and drug delivery. Poly(dioxanone), like PCL, is a polylactone that has been used for purposes such as drug delivery, and tissue engineering They do not need to be extracted after implantation, as they will be degraded by the body of the patient. They can be manufactured as monolithic implants and reservoir-type implants. In addition to the biopolymers, such as the above-mentioned PLA, there a few natural polymers which also represent a promising class of materials with a wide range of applications, including use in implantable devices. These natural polymers include, collagen, hyaluronic acid, cellulose, chitosan, silk and others naturally derived proteins, as well as collagen, gelatin, albumin, elastin and milk proteins. These materials present certain advantages compared to the traditional materials (metals and ceramics) or synthetic polymers, such as biocompatibility, biodegradation and non-cytotoxicity, which make them ideal to be used in implantable drug delivery devices.

Dynamic or Active Polymeric Implants have a positive driving force to control the release of drugs from the device. The majority of the implants in this category are electronic systems made of metallic materials. Dynamic drug delivery implants are mainly pump type implants. The main type of polymeric active implants are osmotic pumps. This type of device is formed mainly by a semipermeable membrane that surrounds a drug reservoir. The membrane should have an orifice that will allow drug release. Osmotic gradients will allow a steady inflow of fluid within the implant. This process will lead to an increase in the pressure within the implant that will force drug release trough the orifice. This design allows constant drug release (zero order kinetics). This type of device allows a favorable release rate but the drug loading is limited.

In some embodiments, the factors are prepared as an injectable paste. The paste can be injected into the implant site. In some embodiments, the paste can be prepared prior to implantation and/or store the paste in the syringe at sub-ambient temperatures until needed.

In other embodiments the factors are prepared as formable putty. The hydrated graft putty can be prepared and molded to approximate any implant shape. The putty can then be pressed into place to fill a void in the cartilage, bone, tooth socket or other site. In some embodiments, graft putty can be used to repair defects in non-union bone or in other situations where the fracture, hole or void to be filled is large and requires a degree of mechanical integrity in the implant material to both fill the gap and retain its shape.

A system for pharmaceutical use, i.e. a drug delivery device with factors, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the NR pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical composition can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxin, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

DETAILED DESCRIPTION OF THE EMBODIMENTS

As summarized above, the present disclosure provides methods for treating adhesions in a subject, which includes, e.g., preventing adhesion formation, halting or reducing the formation of adhesions, and/or reversing or eliminating established adhesions in a subject. Compositions and kits are also provided for performing such methods.

Before aspects of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The present disclosure relates to methods for treating a subject to reduce fibrosis that results in adhesion formation formation, e.g., surgical adhesions, and includes administering to a subject an effective dose of an agent that inhibits AP-1 complex. In some embodiments the fibrosis is an abdominal adhesion. In some embodiments the fibrosis is the result of surgery.

Methods include administering to a subject in need of treatment a therapeutically effective amount or an effective dose of a therapeutic entity. In some embodiments, effective doses of the therapeutic entity described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. Reduction in fibrosis may be monitored for decrease in fibrotic cells, decrease in fatty infiltrating cells, decrease in scar (extracellular matrix) tissue deposition, etc.

In one embodiment, a method of administration for adhesion prevention comprises application of the agent topically as a peritoneal lavage after completion of a surgical procedure.

The effective dose of an agent can vary with the agent, but will generally range from up to about 30 mg/kg, up to about 20 mg/kg, up to about 10 mg/kg, up to about 5 mg/kg, up to about 1 mg/kg, up to about 0.5 mg/kg; up to about 0.1 mg/kg, up to about 0.05 mg/kg; up to about 0.01 mg/kg; for oral administration, where the dose may vary with the specific molecule and route of delivery.

The therapeutic agent may be administered one or a plurality of days, and in some embodiments is administered daily, every two days, semi-weekly, weekly, etc. for a period of from about 1, about 2, about 3, about 4, about 5, about 6, about 7 or more weeks, up to a chronic maintenance level of dosing.

An exemplary treatment regime entails administration once per every day, week, two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage can be administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still yet some other embodiments, for prophylactic applications, pharmaceutical compositions or medicaments are administered to a patient susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. For example, the therapeutic agent may be locally applied at the time of surgery.

In still yet some other embodiments, for therapeutic applications, therapeutic entities of the present invention are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved.

According to the present invention, compositions can be administered by oral, parenteral, topical, including at the site of surgery, intravenous, oral, subcutaneous, intraarterial, intracranial, intraperitoneal, intranasal or intramuscular means. The most typical route of administration is intravenous although other routes can be equally effective.

For parenteral administration, compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies and/or polypeptides can be administered in the form of a depot injection or implant preparation which can be formulated in such a manner as to permit a sustained release of the active ingredient. An exemplary composition comprises polypeptide at 1 mg/mL, formulated in aqueous buffer consisting of 10 mM Tris, 210 mM sucrose, 51 mM L-arginine, 0.01% polysorbate 20, adjusted to pH 7.4 with HCl or NaOH.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

The pharmaceutical compositions are generally formulated as sterile, substantially isotonic and in full compliance with all Good Manufacturing Practice (GMP) regulations of the U.S. Food and Drug Administration. Preferably, a therapeutically effective dose will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1).

Also within the scope of the invention are kits comprising the compositions of the invention and instructions for use. The kit can further contain a least one additional reagent. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Peritoneal adhesions are fibrous tissues that tether organs to one another or to the peritoneal wall and are a significant cause of post-surgical and infectious morbidity. Extensive studies have been done and suggest that hematopoietic cells, cytokines, and fibrin deposition play a major role in promoting adhesion formation. However, the molecular pathogenesis initially promoting adhesion formation has not been well characterized.

Example 1

AP-1 (JUN) Promotes Abdominal Adhesions in Mice and Humans

Adhesions are fibrotic scars that form between abdominal organs following surgery or infection, and may cause bowel obstruction, chronic pain, or infertility. Adhesions occur post-operatively in 50-90% of all open abdominal operations and as such, represent an enormous clinical problem impacting hundreds of millions of patients worldwide. Our understanding of the biology of adhesion formation is very limited, which explains why there are essentially no available treatments that prevent adhesions. To bridge this gap in knowledge, we systemically analyzed abdominal adhesions in mouse and human tissues, at a cellular, transcriptomic, and protein level. First, we show that adhesions derive primarily from the visceral peritoneum, consistent with our clinical experience that adhesion formation is most significant following laparotomy (which involves manipulation of the bowel), rather than laparoscopy with injury to only the parietal peritoneum. Second, adhesion tissue is formed by poly-clonal proliferation of tissue-resident fibroblasts. Third, using single cell RNA-seq, we show that there is heterogeneity among adhesion-forming fibroblasts in both mice and humans, which is more pronounced at an early timepoint. Fourth, AP-1 (JUN) promotes adhesion formation, via JAK-STAT and epithelial mesenchymal transition (EMT) pathway signaling, and results in upregulation of PDGFRA expression among adhesion fibroblasts. With suppression, adhesion formation and profibrotic signaling are significantly diminished. Our findings support AP-1 complexes as a therapeutic target to prevent adhesion formation clinically. A therapy that could be applied intraoperatively to prevent this devastating pathology could dramatically improve the lives of patients who undergo abdominal surgery every year.

In this study, we investigate the origin of adhesion forming cells, and show using in vivo models that adhesions derive primarily from the visceral peritoneum. This is in line with our clinical observation that adhesions are most severe following open abdominal surgical procedures that involve manipulation of the bowel. Using bulk and single cell RNA-seq, we explore patterns of gene expression and heterogeneity among abdominal adhesion fibroblasts derived from mouse and human tissue specimens. These data suggest that JUN is a transcriptional master regulator of fibroblasts in the context of abdominal adhesions. Further, we show that JUN signals via JAKSTAT and epithelial mesenchymal transition (EMT) pathways, and results in upregulation of PDGFRA expression among adhesion fibroblasts. With in vivo JUN suppression, adhesion formation is dramatically decreased. Application of JUN knock-down to primary human adhesion fibroblasts, significantly reduces profibrotic signaling, proliferation, and collagen production.

Our findings suggest that an anti-JUN therapy might be effective to prevent adhesions clinically.

Results

Figure 10:
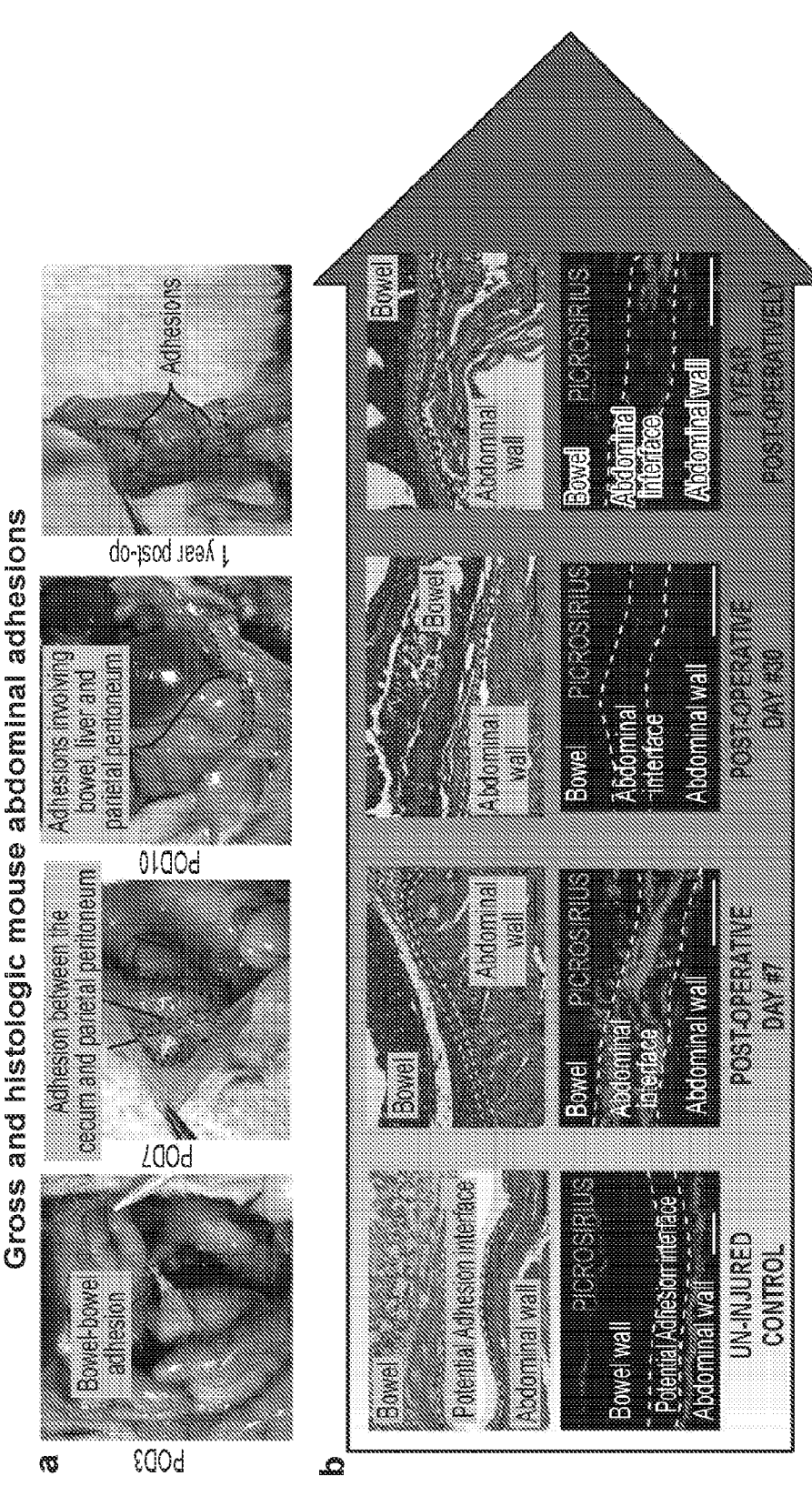
FIG. 10. Gross and histologic mouse abdominal adhesions. a, Photographs of representative samples illustrating adhesions in mice: bowel-bowel adhesion at POD 3 (far left), parietal to visceral peritoneal adhesion at POD 7 (2nd to left), adhesions also involving of the liver (2nd to right), persistence of adhesions at one year post-operatively (far right). Adhesion interfaces outlined with black dotted lines, POD=post-operative day. n=5. b, Time course of mouse adhesion formation using H&E (top panels) and picrosirius red (bottom panels) staining: Images of representative samples, uninjured control tissue from healthy litter mates (potential adhesion interface indicated, far left), POD 7 (2nd to left), POD 30 (2nd to right), 1 year post-operatively (far right). Stains as labelled in figure, adhesion interfaces outlined with dotted lines. n=5. Grey scale bars, 200 μm; black scale bars, 100 μm; white scale bars, 50 μm.
Figure 11:
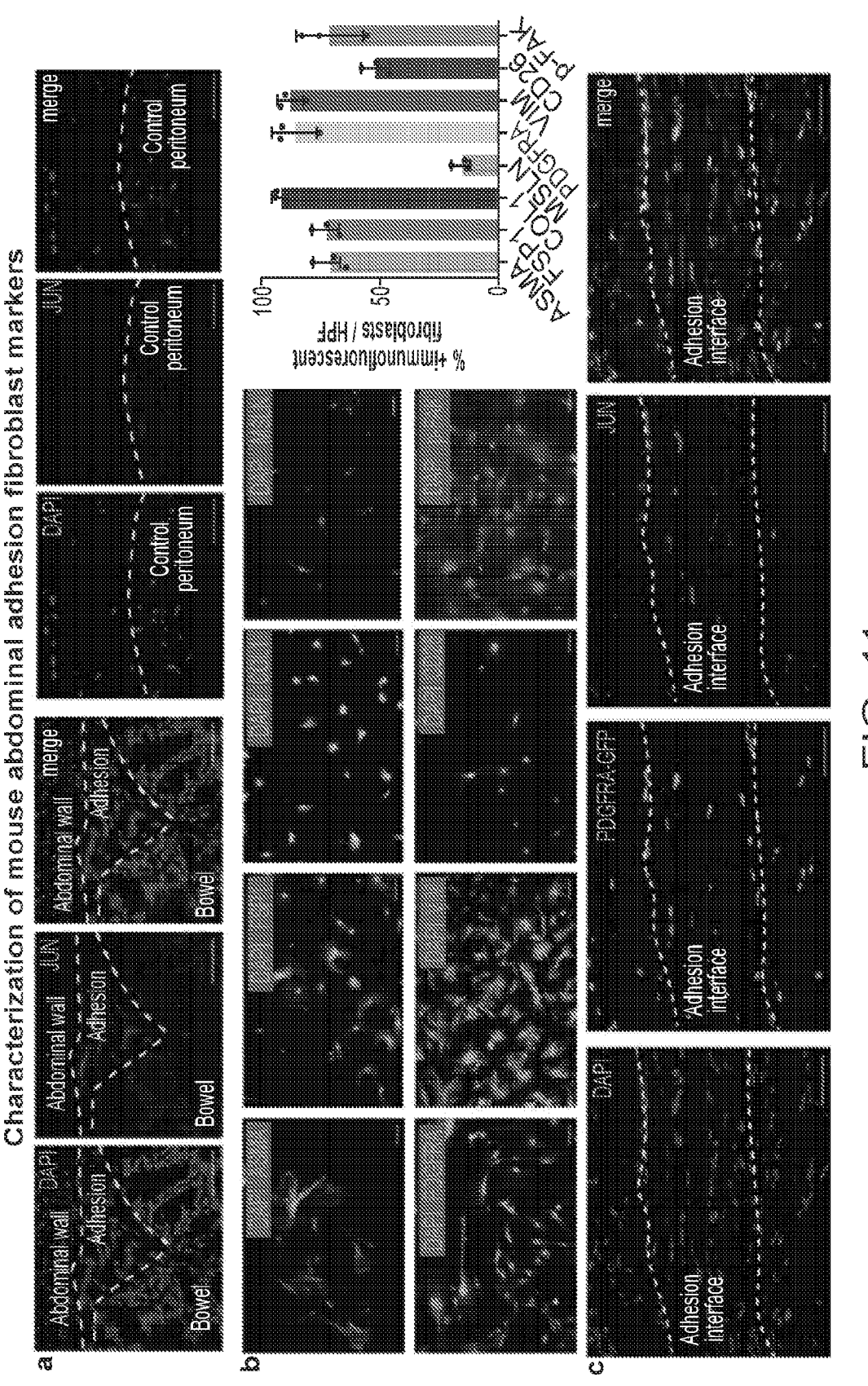
FIG. 11. Characterization of mouse abdominal adhesion fibroblast markers. a, Representative sample showing immunofluorescent staining for JUN in wild-type mouse adhesions (left panels) compared with control (uninjured) peritoneum from healthy litter mates (right panels). Individual channels, merge and structures as labelled in figure, white dotted lines highlight adhesion interface in left panel and edge of peritoneum in right panel. n=3. Scale bars, 50 μm. b, Representative images of immunocytochemistry screening of unbiased, FACS-isolated abdominal adhesion fibroblasts from wild-type mouse adhesions using ASMA, PDGFRA, FSP1, Vimentin (VIM), COL1, CD26, MSLN, phospho-FAK. Quantitation at far right—shows % of + cells per marker per high power field (HPF). n=3. Scale bars, 100 μm. c, Immunofluorescent staining for p-JUN in a representative PDGFRAGFP adhesion tissue sample. Individual channels, merge and structures as labelled in figure, white dotted lines highlight adhesion interface. n=5. Scale bars, 50 μm. d, Immunofluorescent staining of representative wild-type mouse abdominal adhesion tissue samples for fibrosis-relevant markers. Adhesion interfaces outlined with thick white dotted lines, antibody markers indicated at top right of images, individual channels with merge at right, zoom at far right, co-expressing cells indicated with thin white dotted lines where identified. n=3. Scale bars, 50 μm. Data and error bars represent means±SD.
Figure 11:
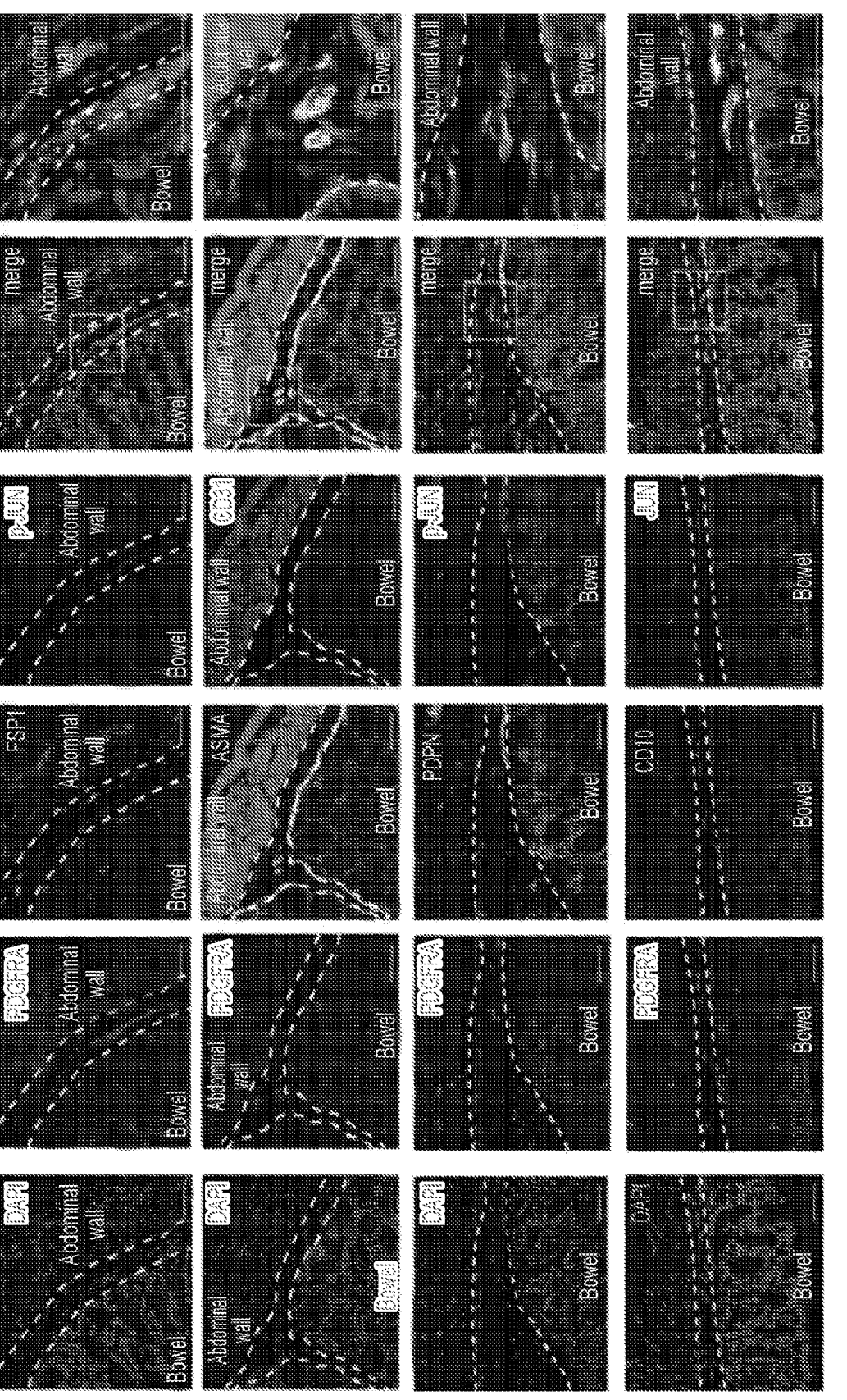
Figure 12:
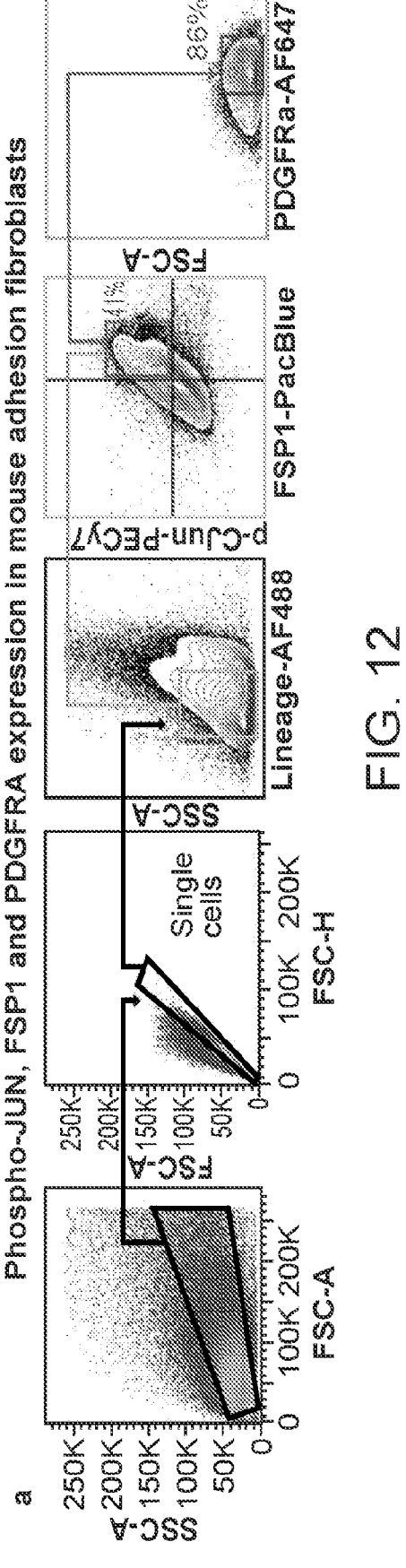
FIG. 12. Phospho-JUN, FSP1, and PDGFRA expression in mouse adhesion fibroblasts. a, Representative flow cytometry plots showing analysis of mouse adhesion fibroblasts for expression of phospho-JUN, FSP1 and PDGFRA. Percentages of cells noted in corresponding colors in figure. n=3.

JUN promotes abdominal adhesion formation and upregulates adhesion fibroblast PDGFRA expression. JUN is a member of the Activator Protein 1 (AP-1) transcription factor complex, which has conserved function in mice and humans. To explore if JUN promotes abdominal adhesion formation, we examined JUN expression in an established model for mouse adhesions. This surgical model relies on abrasive injury to both the visceral and parietal peritoneum and results in the formation of dense adhesions, which are maintained over the life span of the mice (FIG. 10a-b). We found that JUN expression is upregulated in adhesion tissue (FIG. 11a—left panels) compared with control peritoneum in wild-type mice (FIG. 11a—right panels). Using a flp-in tetO c-jun (JUN) mouse, JUN expression results in significantly increased adhesion formation (FIG. 1a-b) compared with wild-type mice (FIG. 1a-b, FIG. 10a-b). JUN produces downstream signaling through several known fibrosis-related pathways, including VEGF, FGFR, PDGFR, and TGFBR. To explore JUN signaling in the context of adhesions, we isolated mouse adhesion fibroblasts via fluorescence activated cell sorting (FACS) using an unbiased approach involving lineage-labeling of non-fibroblast cells. We screened the isolated fibroblasts for expression of fibrosis-relevant markers, and found that PDGFRA, along with activated-fibroblast markers including a-smooth muscle actin (ASMA), vimentin (VIM), and collagen 1 (COL1), are strongly expressed by mouse adhesion fibroblasts (FIG. 11b—quantitation at right). PDGFRA is a transmembrane receptor tyrosine kinase and fibroblast marker in the dermis, and is a known promotor of systemic fibrosis. To validate PDGFRA expression in adhesion-forming fibroblasts, we created adhesions in PDGFRAGFP mice (FIG. 1c). JUN expression is also expressed in abdominal adhesions in these tissues (FIG. 11c). Fluorescent imaging of uninjured bowel and abdominal wall shows PDGFRA-expressing cells scattered throughout both structures in a pattern typical for tissue-resident fibroblasts (FIG. 1d). Seven days after surgery, PDGFRA-expressing cells are numerous along the adhesion interface (FIG. 1e—top panel). At post-operative day (POD) 14, PDGFRA-expressing cells increase in the adhesion interface (FIG. 1e—middle and bottom panels, FIG. 1f), suggesting that this cell population is a primary contributor to adhesions. Mouse adhesion fibroblasts also express fibroblast specific protein-1 (FSP1) (FIG. 11b), which labels fibroblasts in lung and liver fibrosis. FSP1 expression upregulates JAK2/STAT5 signaling in adventitial fibroblasts. We found that FSP1 expression correlated with JUN expression (mean 76% of JUN+ fibroblasts, SD 2.9) (FIG. 12a, FIG. 11d—top row). PDGFRA expression captures the majority of the JUN+ adhesion fibroblasts (mean 90.6% of phospho-JUN+/FSP1+ cells, SD 2.1) (FIG. 1g—left panels, FIG. 12a, FIG. 11d—top row), although there are also minor populations of fibroblasts that express PDGFRA and JUN independently (FIG. 1g—right panels), indicating heterogeneity among the fibroblasts responsible for adhesions. ASMA expression, known to identify activated fibroblasts, is similar to PDGFRA expression (FIG. 11d—second row). We explored expression of other fibrosis-associated fibroblast markers including podoplanin (PDPN) and CD10, which were found to be relatively less expressed in mouse adhesions (FIG. 11d—bottom rows).

Figure 13:
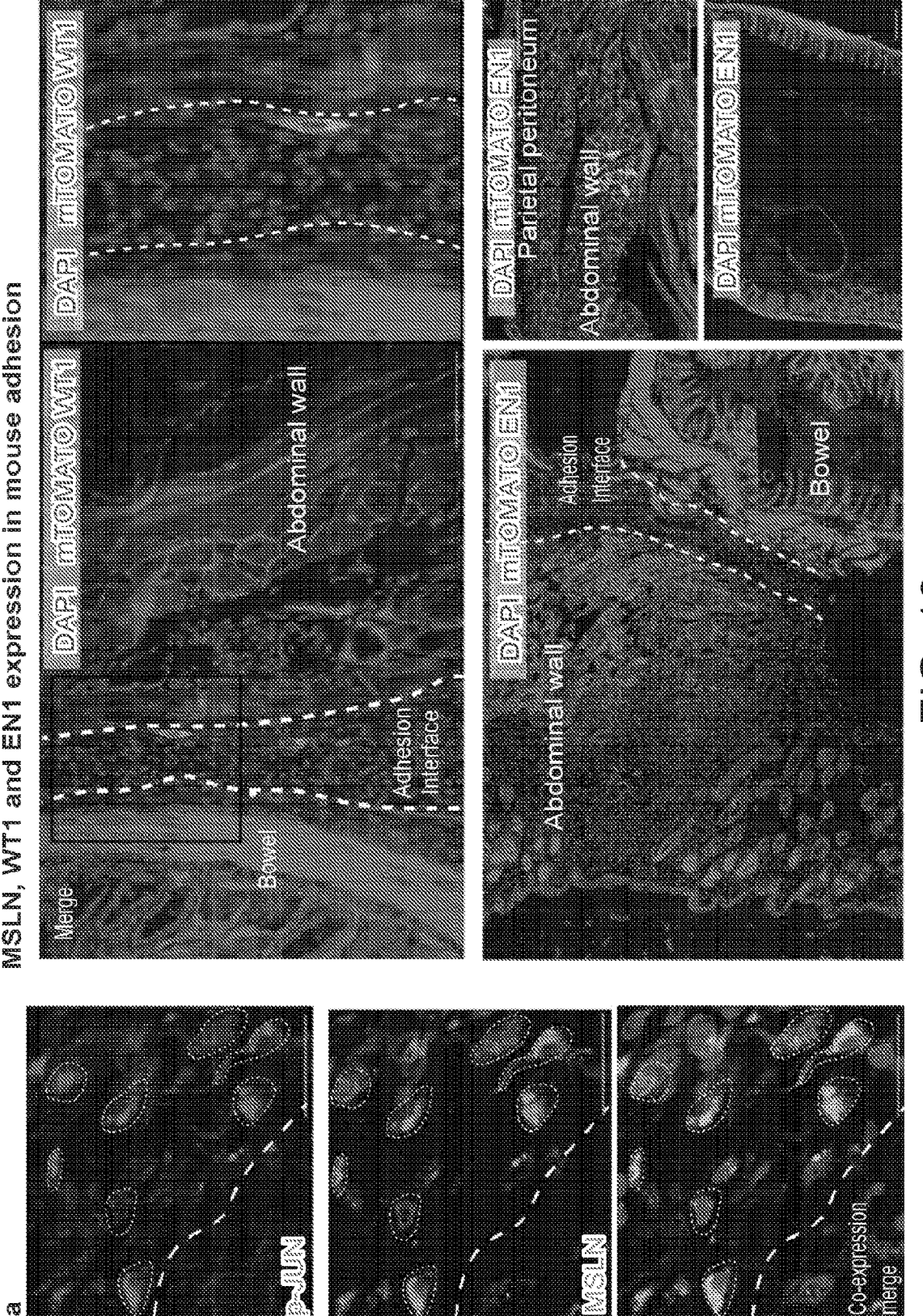
FIG. 13. MSLN, WT1 and EN1 expression in mouse adhesions. a, Images of representative mouse adhesion tissue with immunofluorescent staining for phospho-JUN and MSLN. Adhesion interfaces outlined with thick white dotted lines, antibody markers indicated at bottom left of images, co-expressing cells highlighted with thin white dotted lines. n=3. Scale bars, 25 μm. b, Images of representative ischemic button peritoneal fibrosis mouse model and abdominal adhesion tissue with immunofluorescent staining for JUN (left panels) and MSLN (right panels) with corresponding trichrome staining (far left panels). Black dotted lines indicate adhesion interface in trichrome images, white dotted lines indicate adhesion interface in immunofluorescent images. Conditions labelled at left and above images. n=3. Scale bars indicated on merge images, 100 μm. c, Fluorescent imaging data from representative samples from WT1Cre::ROSA26mTmG mice shows that WT1-expressing fibroblasts (green) very rarely contribute to adhesion formation (top panels, zoom of box as indicated on adhesion interface at right. EN1-lineage fibroblasts appear minimally present in the parietal peritoneum (middle right panel), are not found in the bowel wall (bottom right panel), and do not contribute to adhesions (bottom left panel). White dotted lines indicate adhesion interface, structures as labeled on figure. n=3. Scale bars, 100 μm.
Figure 13:
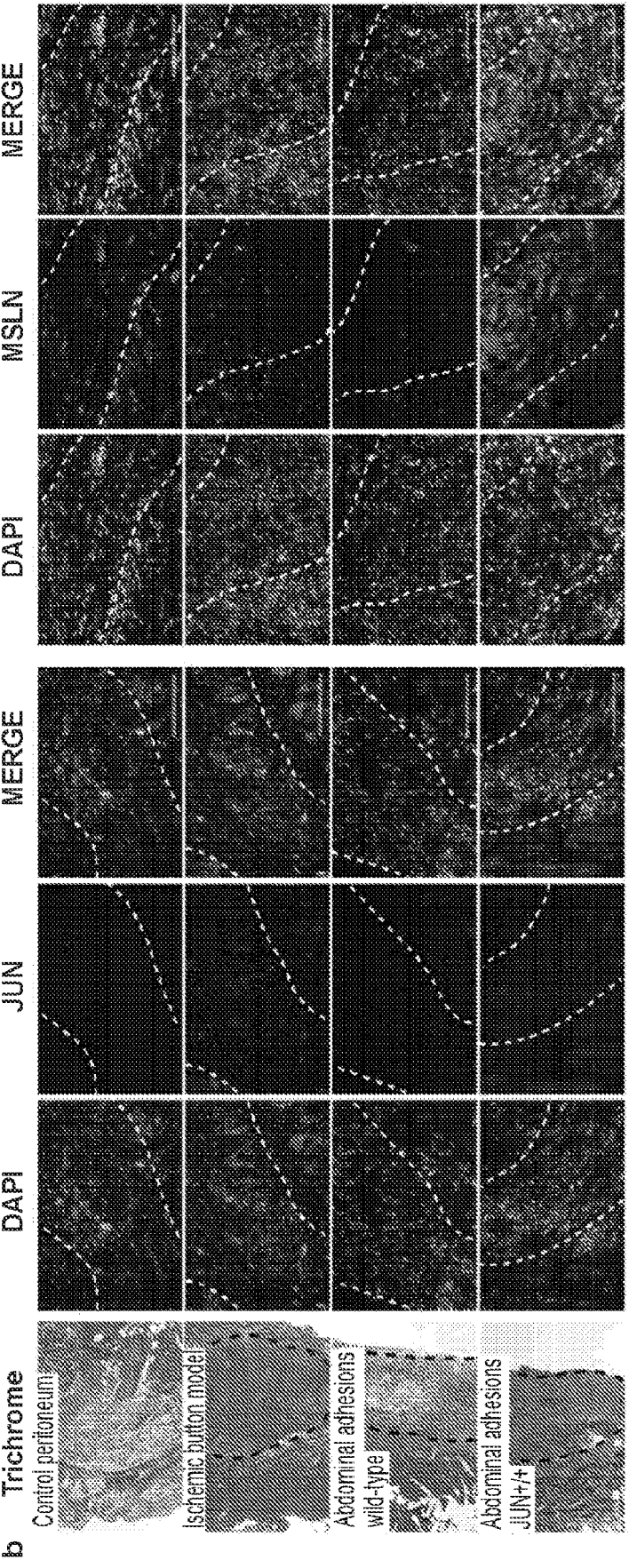

Adhesion fibroblasts can be characterized by expression of JUN, PDGFRA, ASMA, and to a lesser extent, FSP1, in mice. IL6, STAT3, and STAT5 are also expressed in adhesion tissue. IL6 is a known mediator of inflammation and fibrosis in the liver. STAT5 expression is central to myelo- and lymphoproliferative disease and is upregulated in other fibrotic pathologies including bleomycin-induced pulmonary fibrosis. Following peritoneal injury with vessel damage in the context of abdominal surgery or intra-abdominal infection, platelets are recruited to the site and immediately release acute phase factors such as IL6 and PDGF. We hypothesize that this results in the preliminary activation of JUN, which can then auto-amplify, signal via STAT3 and STAT5, and stimulate fibroblast production of IL6 and related factors, ultimately driving a chronic fibrotic state in these cells. We found that in our model of abdominal adhesions, mesothelin (MSLN) was expressed by a portion of the JUN+ fibroblast population (FIG. 13$a$). This is consistent with a "hypoxic button" model of parietal peritoneal fibrosis, which found MSLN to be strongly expressed in the parietal peritoneum. As such, we wanted to determine if JUN expression might also be upregulated in that model.

Using the hypoxic button model, we found that JUN expression is strongly induced and correlates with prominent MSLN expression, suggesting that JUN may also be responsible for fibrosis in that context (FIG. 13$b$). Previous research exploring ischemic fibrosis in the parietal peritoneum suggested elevated expression of Wilms tumor antigen 1 (WT1). We found that this protein does not contribute significantly to adhesion tissue using our model in endogenous WT1-expressing mice (WT1$^{Cre}$::ROSA$^{mTmG}$) (FIG. 13$c$—top panels). Similarly, Engrailed-1 (EN1)-lineage fibroblasts, which are the predominant scar forming fibroblast in the dorsal dermis of skin, are only rarely present in the parietal peritoneum using endogenous EN1-expressing mice (EN1$_{Cre}$::ROSA$_{mTmG}$), are not found in the visceral peritoneum, and do not contribute to adhesions (FIG. 13$c$—bottom panels).

Figure 2:
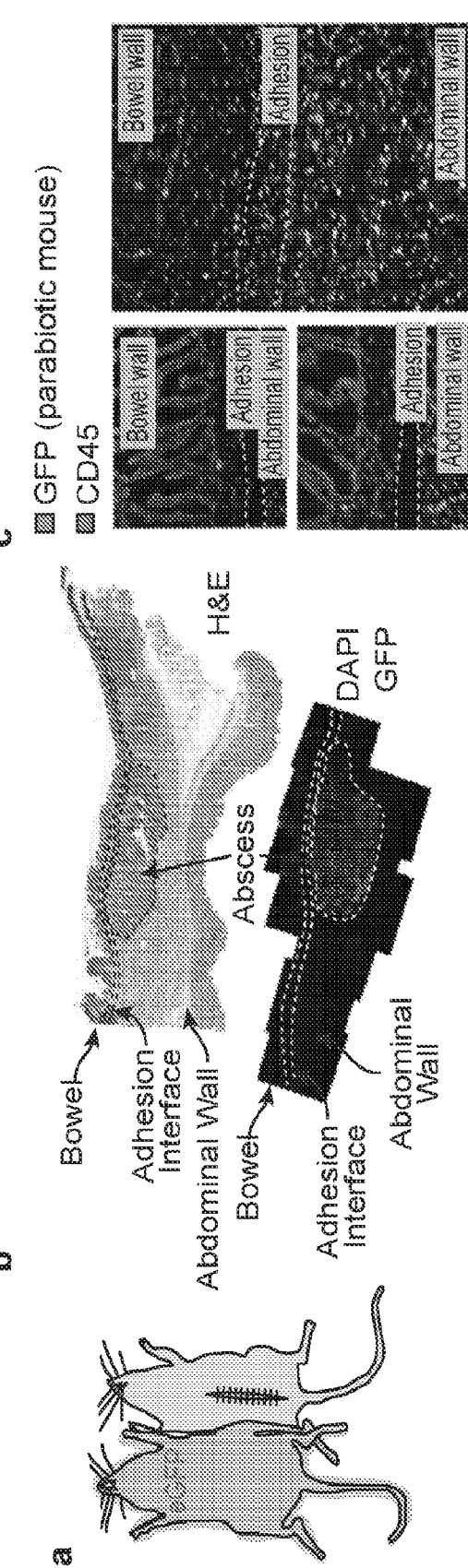
FIG. 2. Abdominal adhesions are formed by local fibroblasts that proliferate clonally a, Parabiosis schematic. b, H&E and IF data showing the presence of an abscess identified along the abdominal wall adjacent to the adhesion interface in a mouse parabiont, which is strongly GFP+ secondary to the presence of circulating immune cells in the abscess. c, No GFP+ cells were identified in the adhesion interface. Green (GFP) represents circulating cells, purple (CD45) stains for immune cells. n=5. Scale bars, 50 μm. d, Schematic of the Actin$^{CreER}$::Rainbow mouse construct (top panel), schematic showing. Actin$^{CreER}$::Rainbow mice locally induced with activated tamoxifen liposomes at time of adhesion formation, using a published protocol36 (second panel), Actin$_{CreER}$::Rainbow mouse uninjured control (third panel) and adhesion tissue harvested at POD14 (bottom panel). Clonal proliferation of fibroblasts are visualized along the adhesion interface. Representative samples, structures as labelled in figures, white dotted lines outline adhesion, white asterisk marks adhesion interface, confocal imaging. n=5. Scale bars, 25 μm. e, Schematic of the PDGFRA$^{CreER}$::Rainbow mouse construct (top panel), confocal imaging of representative PDGFRA$_{CreER}$::Rainbow mouse adhesion samples showing cellular clonality in the adhesion interface at POD 7 (top panels, Imaris rendering at right), and POD 14 (bottom panels, Imaris rendering at right). Structures as labelled in figures, thick white dotted lines outline adhesion interface, thin white dotted lines outline individual clones, confocal imaging. n=5. Scale bars, 50 μm.
Figure 2:
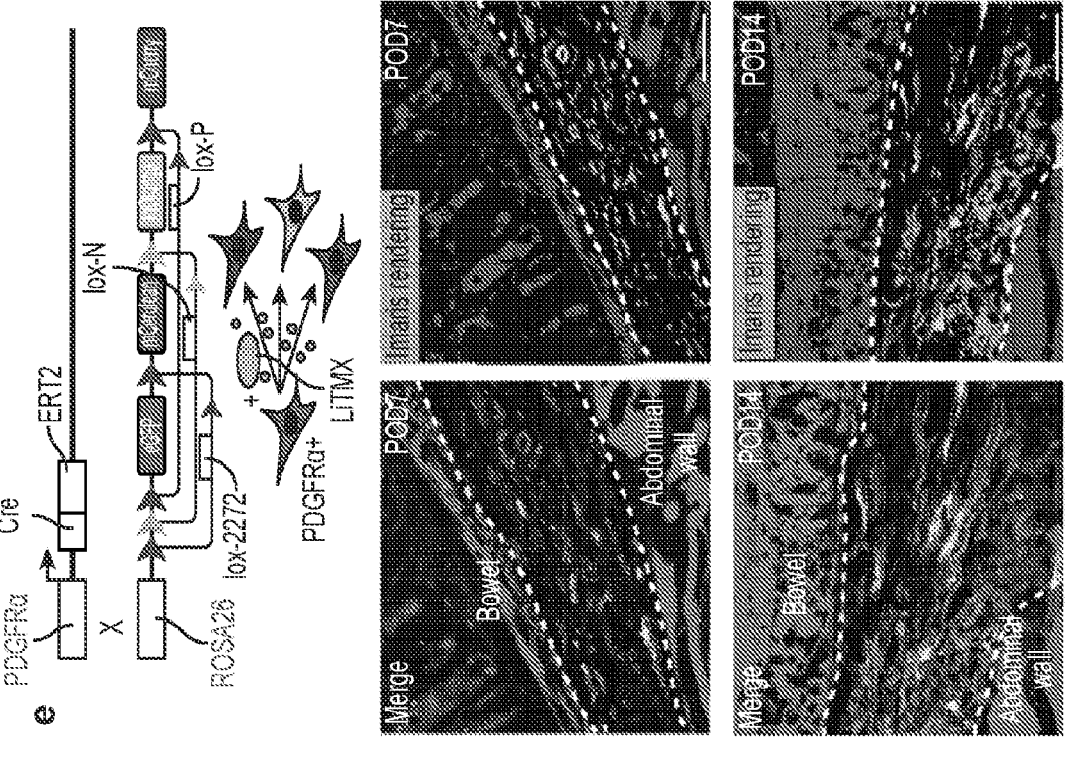
Figure 2:
Figure 2:
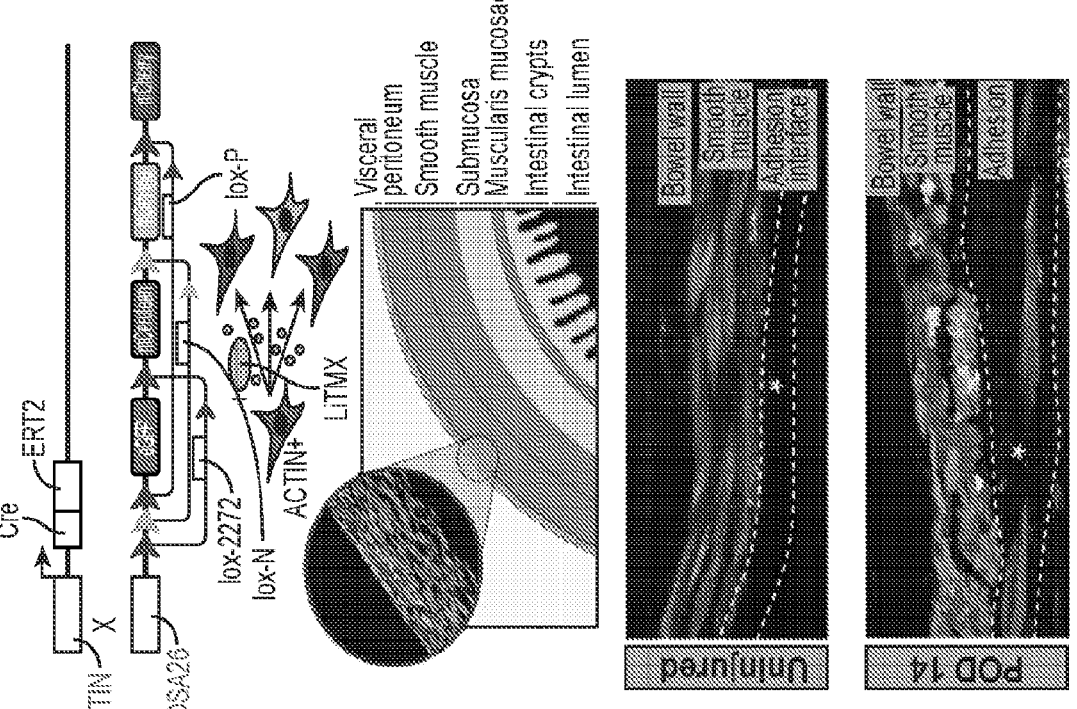

Abdominal adhesions are formed by local fibroblasts that proliferate clonally We hypothesized that there are two possible sources for adhesion-forming cells: local tissue resident cells activated in the context of abdominal surgery, or systemic circulating cells recruited to the site following injury. To investigate this, we created adhesions in wild-type mice parabiosed to eGFP (ACTIN$^{GFP}$) mice (FIG. 2$a$—left panel). At POD 14, we found histologically that there was no significant contribution from circulating mesenchymal cells (GFP+) to the adhesion interface (FIG. 2$c$), while a dense contribution of GFP+ cells was seen in an abscess in the abdominal wall which formed nearby the adhesion interface in one of the samples, further validating our model (FIG. 2$b$). These data indicate that the major source of adhesion-forming cells is local tissue.

Our previous work has demonstrated poly-clonal proliferation of tissue-resident cells involved in wound healing, suggesting the presence of local progenitor-type cells that are activated in response to injury. To determine whether adhesions are formed by poly-clonal proliferation of local cells, we created abdominal adhesions in Rainbow mice (ACTIN$^{CreER}$::ROSA26$^{VT2/GK3}$) (FIG. 2$d$—top panel). The Rainbow mouse expresses an inducible fluorescent reporter. After induction, cells expressing the Cre driver of interest express one of four colors (eGFP, mCerulean, mCherry, mOrange) and all subsequent progeny cells express the same color as the initial parent cell.

We induced the peritoneum of ACTIN$^{CreER}$::ROSA26$^{VT2/}$$_{GK3}$ mice during adhesion formation (FIG. 2$d$—second panel) using locally-applied 4-hydroxytamoxifen liposomes, which permits precise labelling of tissue-resident cells. Compared with uninjured peritoneum (FIG. 2$d$—third panel), clonal expansion of Rainbow cells was observed extending along the adhesion interface (FIG. 2$d$—bottom panel) at POD 14. We confirmed the identity of the clonal cells as adhesion-forming fibroblasts by inducing adhesions in Rainbow mice using an inducible PDGFRA$_{CreER}$ driver (PDGFRA$_{CreER}$::ROSA26$_{VT2/GK3}$) (FIG. 2$e$—top panel). Clonal proliferation of PDGFRA+ Rainbow fibroblasts is seen along the adhesion interface at POD 7 (FIG. 2$e$—middle panels), and these clones expand at POD 14 (FIG. 2$e$—bottom panels). These data show that adhesions arise from tissue-resident, progenitor-type fibroblasts that proliferate clonally in response to injury.

Figure 3:
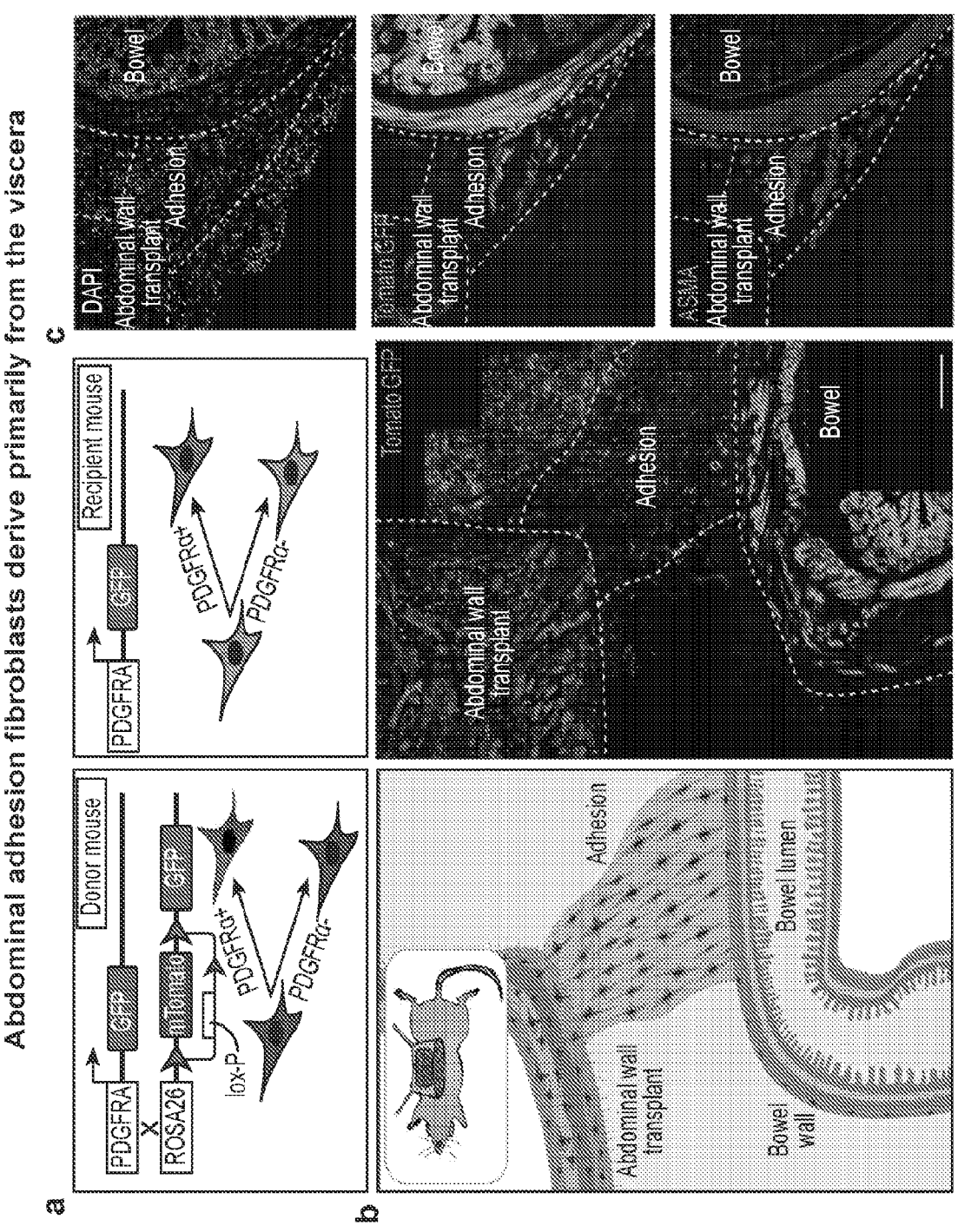
FIG. 3. Abdominal adhesion fibroblasts derive primarily from the viscera a, Schematics of the PDGFRA$^{GFP}$::Rosa$^{mTmG}$ mouse "donor" model (left panel) and PDGFRA$^{GFP}$ "recipient" model (right panel). b, Schematic (left panel) for abdominal wall transplant model using abdominal wall from PDGFRA$^{GFP}$::Rosa$^{mTmG}$ mice, transplanted into PDGFRA$^{GFP}$ mice, followed by adhesions surgery. Confocal imaging of representative mouse adhesion tissue (right panel) shows a prominence of GFP+ cells within the adhesion interface, relative to GFP-mTomato+ cells, harvested at POD 14. White dotted lines mark structures as labelled in images, confocal imaging. n=5. Scale bar, 100 μm. c, Confocal imaging of the abdominal wall transplant model representative tissue shows PDGFRA/ASMA co-expression (PDGFRA labelled with GFP using the mTmG mouse model, IF staining for ASMA) among the cells migrating from the visceral peritoneum into the adhesion interface. White dotted lines mark structures as labelled in images, confocal imaging. n=5. Scale bars, 100 μm.
Figure 14:
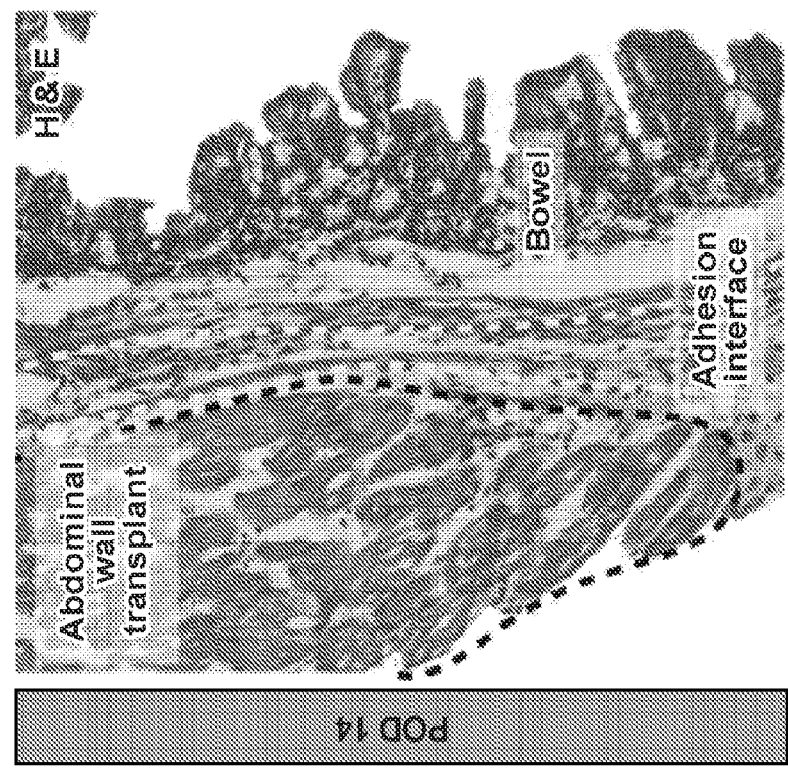
FIG. 14. Abdominal wall transplant model. a, Gross (left panel, yellow dotted lines outline abdominal wall transplant) and histologic (right panel, H&E, yellow dotted line outlines adhesion interface) images of abdominal wall transplant model. Structures as labelled in figure. n=5.
Figure 14:
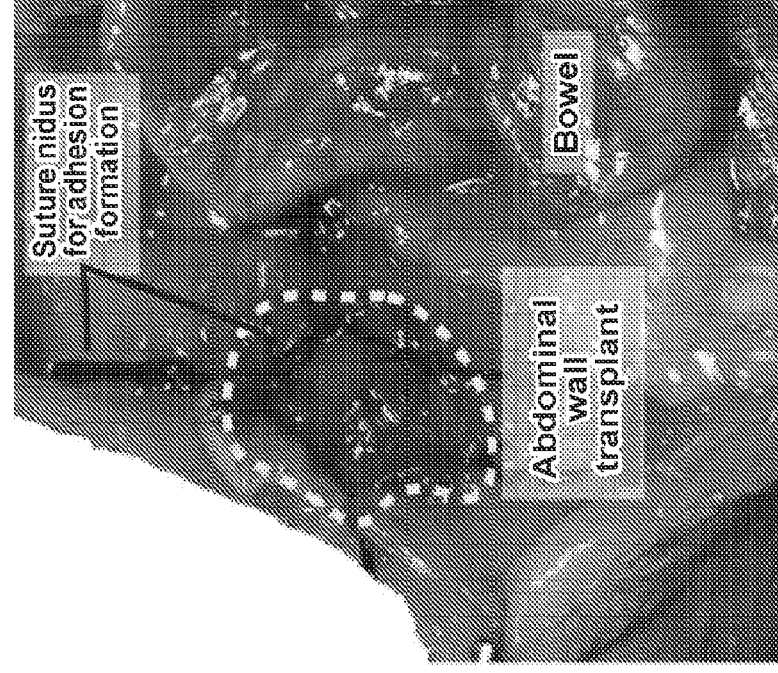

Abdominal adhesion fibroblasts derive primarily from the viscera Clinically, adhesion formation is most pronounced after open laparotomy during which the bowel is manipulated, rather than following laparoscopy (which often only injures the parietal peritoneum). This supports the idea that the visceral (bowel wall) peritoneum might be the primary contributor to adhesion formation. To determine whether cells from the visceral or parietal (abdominal wall) peritoneum are more active in adhesion formation, we designed an abdominal wall transplant procedure. The abdominal wall (full thickness muscular layer and parietal peritoneum) of PDGFRA$^{GFP}$::Rosa$^{mTmG}$ mice, in which all cells express membrane (m) Tomato, and PDGFRA+ cells express both m-Tomato and GFP (FIG. 3$a$—left panel), was excised and rapidly transplanted to the abdominal wall of PDGFRA$^{GFP}$ mice, in which PDGFRA+ cells express GFP (FIG. 3$a$—right panel, FIG. 14$a$—left panel). Adhesions were then created between the native bowel and the transplanted wall (FIG. 3$b$—left panel, FIG. 14$a$—right panel). At POD 14, the vast majority of fibroblasts in the adhesion interface were GFP+, derived from the visceral rather than parietal peritoneum (FIG. 3$b$—right panel). ASMA expression was found to correlate closely with PDGFRA (GFP) expression in this context (FIG. 3$c$). In summary, abdominal adhesions are derived primarily from the visceral peritoneum, supporting the well-known clinical observation.

Figure 4:
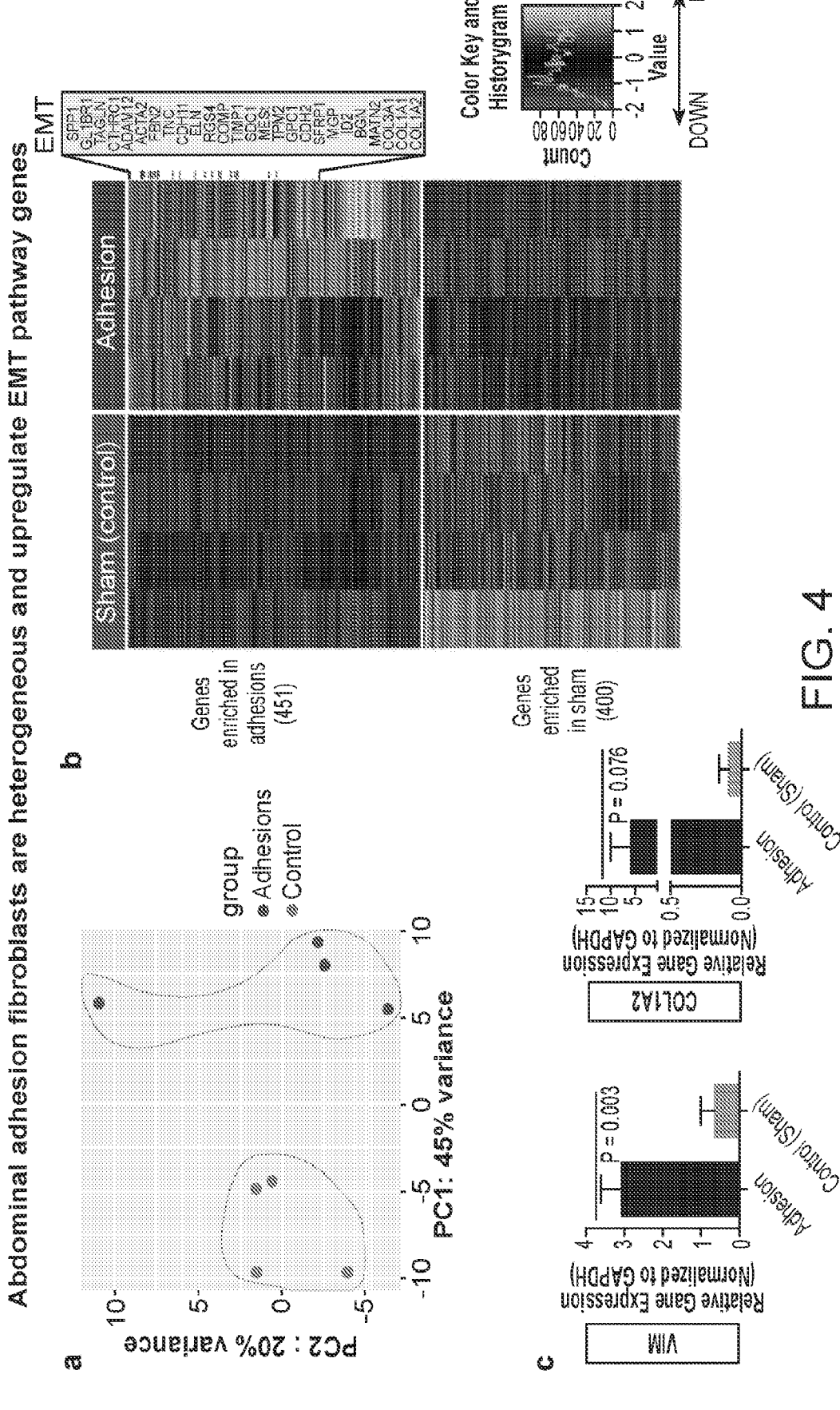
FIG. 4. Abdominal adhesion fibroblasts are heterogeneous and upregulate EMT pathway genes a, Principal component analysis (PCA) plot comparing bulk RNA-seq gene expression for adhesion (n=4) and control peritoneum (n=4) FACS-isolated mouse fibroblasts. Colors as labelled, variances noted on plot. b, Heatmap of mouse adhesion-forming fibroblast bulk RNA-seq data shows significant differential gene expression between adhesion and control peritoneum (sham surgery) cohorts. Upregulated EMT pathway genes noted at right. Gene enrichment as noted in figure, color key and histogram at far right. c, Quantitation of qPCR for vimentin (VIM) and collagen 1a2 (COL1A2) shows upregulation of gene expression in the context of mouse abdominal adhesions. Data and error bars represent means±SD; P values noted in figure, unpaired two-tailed t test. n=3 biological replicates per condition. d, Uniform manifold approximation and projection (UMAP) plot showing single cell (sc) RNA-seq data from mouse adhesion fibroblasts FACS-isolated using an unbiased, lineage-negative sort strategy at POD 2 (n=4) and POD 7 (n=4) following adhesion induction. Three unique clusters of fibroblasts are identified. Colors as labelled in the figure panel. e, UMAP plot showing distribution of mouse scRNA-seq fibroblasts in terms of harvest timepoint relative to the clusters in panel d. Cells isolated at both timepoints are represented in all clusters. Colors as labelled in the figure panel. f, Pseudotime analysis (Monocle 2) of mouse scRNA-seq data: Pseudotime analysis (left panel), representation of scRNA-seq clusters across the pseudotime analysis shows a clear progression from cluster 1 to clusters 0 and 2 (middle panel) and relative to timepoints, the cells follow a logical time progression that mirrors the pseudotime with the largest representation of POD 2 cells in cluster 1 and more POD 7 cells in clusters 0 and 2 (right panel). Arrows indicated direction of pseudotime progression. g, Violin plots showing expression of STAT5 and ASMA relative within the scRNA-seq data. Colors and numbering on x axis match cluster colors assigned in panel d. h, Additional violin plots showing expression of JUN, STAT3, FSP1, IL6, MCP1, and PDGFRA relative to the to the scRNA-seq data clusters seen in panel d. Colors and numbering on x axis match cluster colors assigned in panel d.
Figure 15:
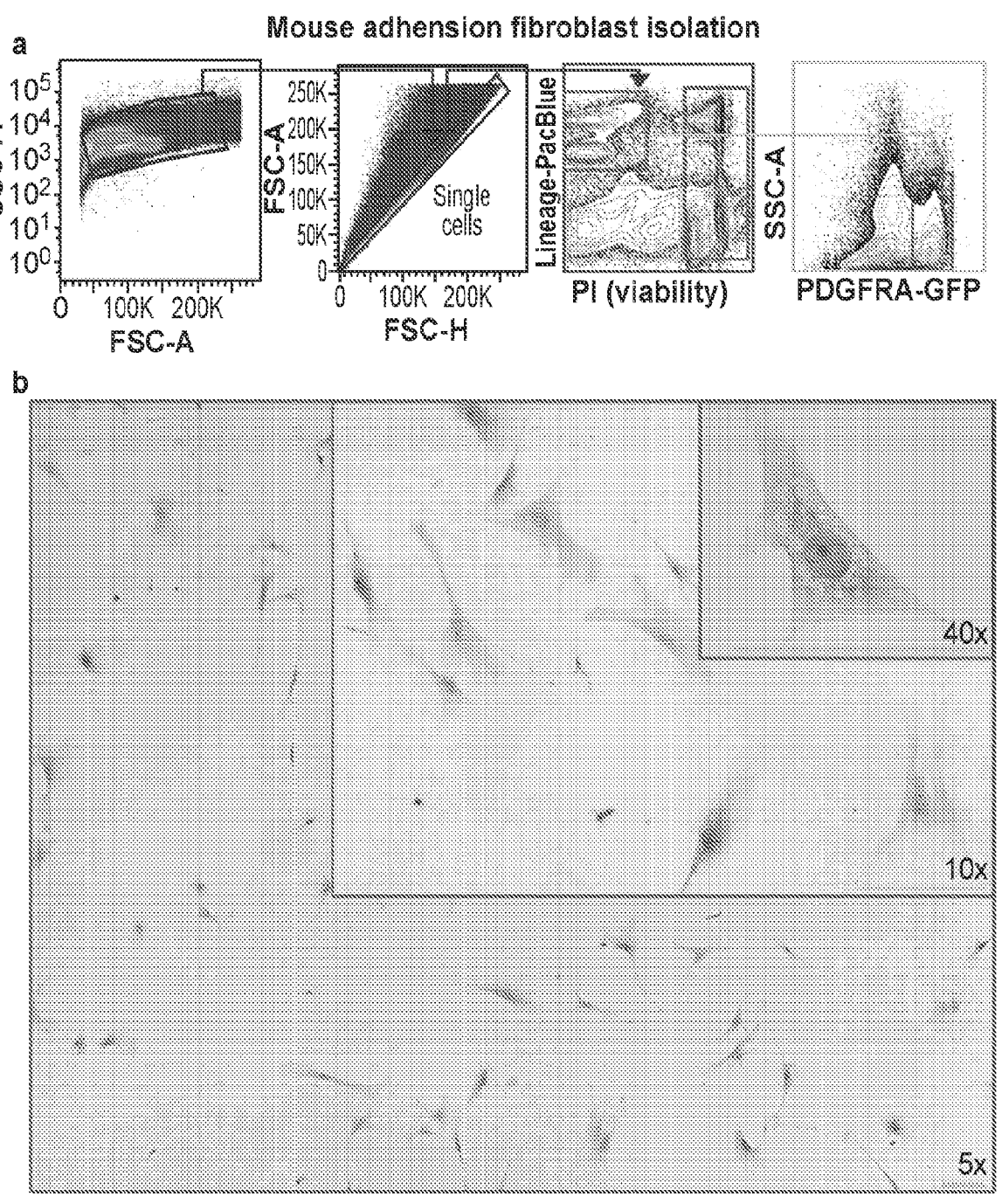
FIG. 15. Mouse adhesion fibroblast isolation. a, FACS isolation strategy for mouse abdominal adhesion fibroblasts, example of representative gating. n>10. b, Eosin stained FACS-isolated mouse adhesion fibroblasts. Zoom noted at right bottom of images. Scale bars, 25 μm.

Abdominal adhesion fibroblasts are heterogeneous and upregulate EMT pathway genes Next, we examined FACS-isolated mouse adhesion fibroblast gene expression using bulk RNAseq (FIG. 15$a$-$b$). Principal component analysis (PCA) showed clear separation between adhesion and control (sham-surgery) transcriptomes (FIG. 4$a$). We then compared gene expression profiles of adhesion and control specimens. Using DESeq2, we identified 451 genes that were significantly enriched in mouse adhesion fibroblasts and 400 that were significantly enriched in sham-surgery control cells (false discover rate [FDR], <0.01; FIG. 4$b$, Table 1). Genes upregulated in mouse adhesion fibroblasts are known to be involved in fibroblast activation and fibrosis, including ACTA2 (ASMA), tenascin C (TNC), and COL1A1, COL1A2, and COL3A1.

Figure 16:
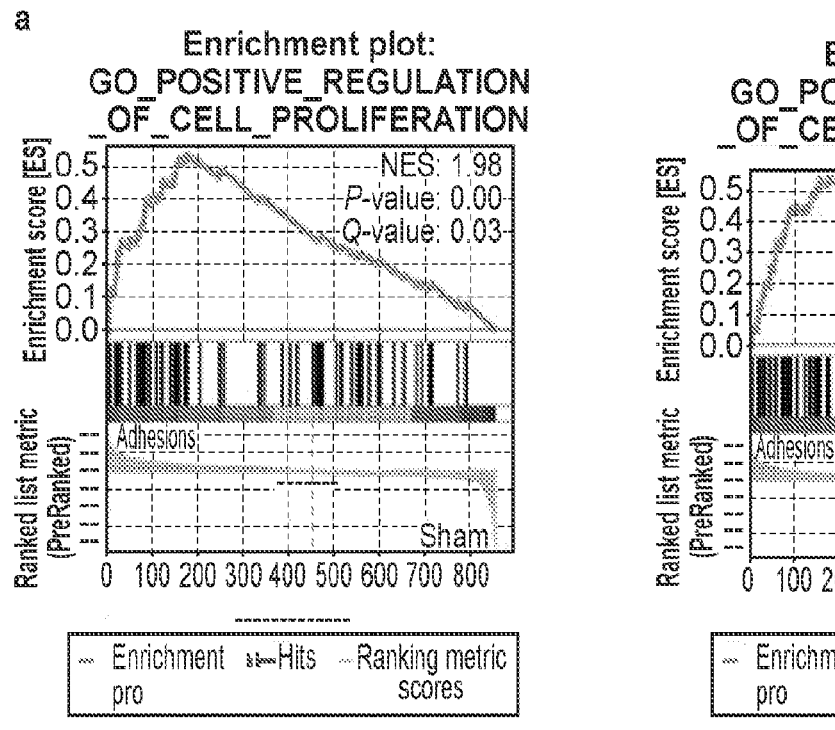
FIG. 16. Mouse adhesion fibroblast RNA-seq GSEA and GO analysis. a, Gene Set Enrichment Analysis (GSEA) of mouse adhesion fibroblast bulk RNA-seq data shows enrichment of 'Cell Proliferation', 'Cell Differentiation', 'Epithelial Mesenchymal Transition (EMT)' and 'Regulation of Response to Wounding' pathways. NES, P and Q values noted in figure panels. b, Gene Ontology (GO) term analysis for mouse RNA-seq dataset. Terms and statistics as noted in figure panels.
Figure 16:
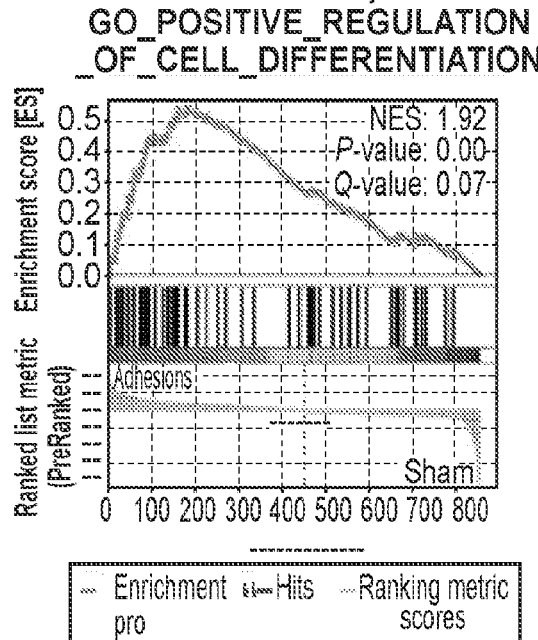
Figure 16:
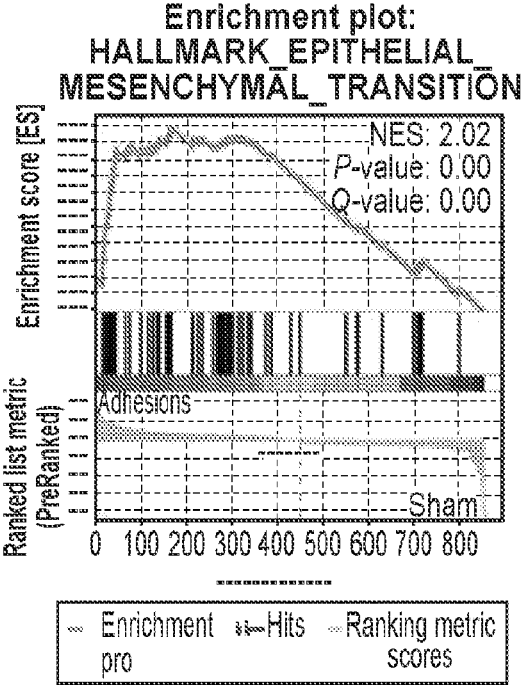
Figure 16:
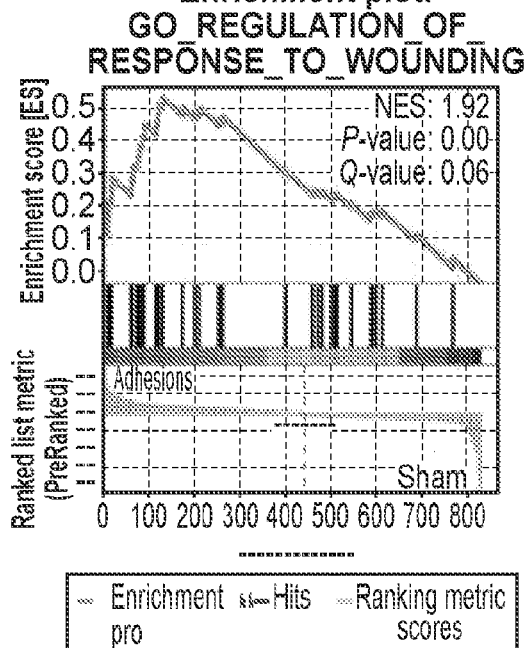
Figure 16:
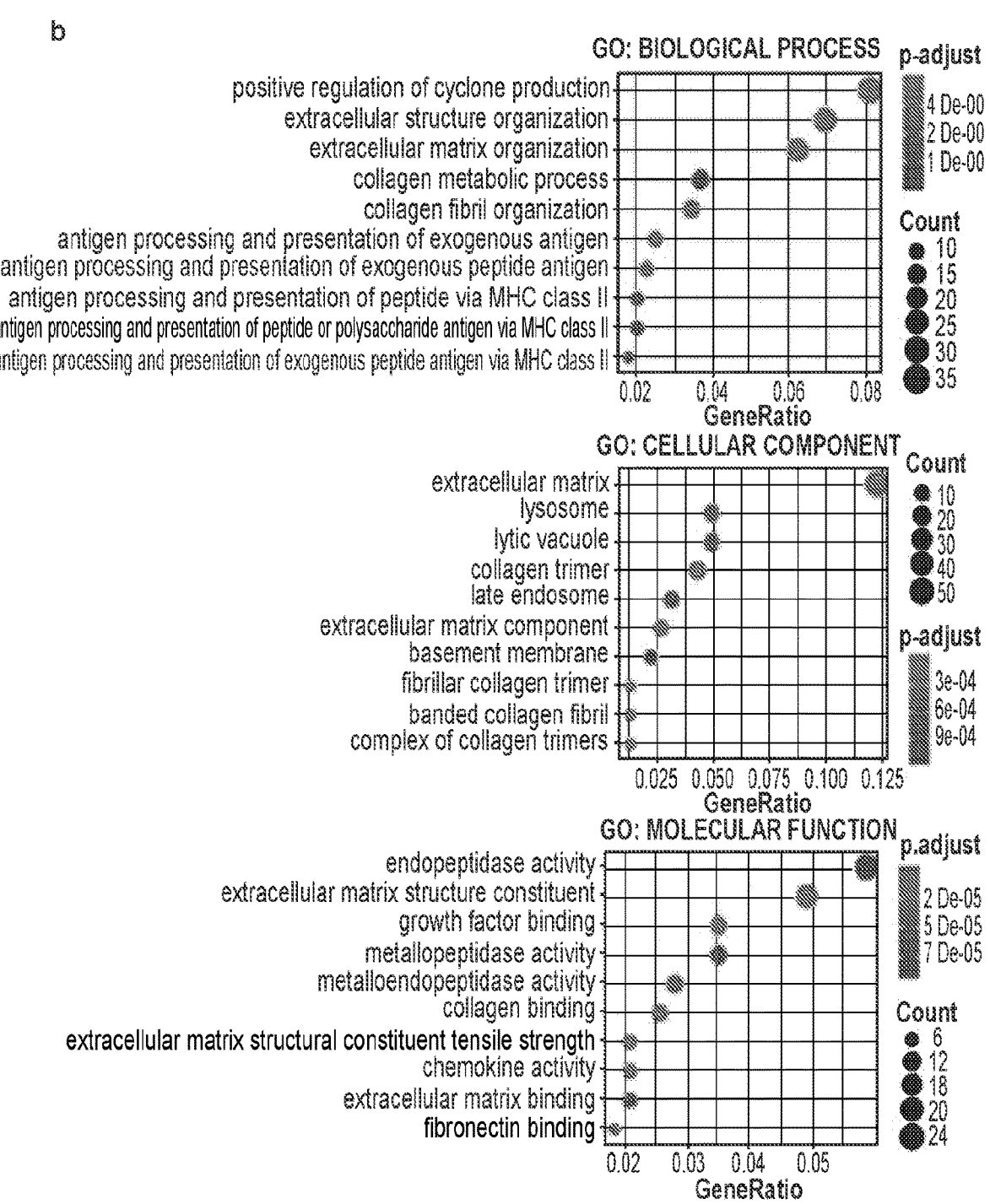

We next performed gene set enrichment analysis (GSEA) using the Molecular Signatures Database (MSigDb) to identify expression programs associated with mouse adhesion fibroblasts. One of the most significantly enriched molecular signatures in mouse adhesion fibroblasts was the epithelial-mesenchymal transition (EMT) pathway (FIG. 16$a$). EMT is associated with cell proliferation in the setting of neoplasia as well as tissue fibrosis in a variety of organ systems including hepatic fibrosis. Specific genes of interest in this pathway relating to organ fibrosis include osteopontin (SPP1), periostin (POSTN), TIMP-1, cartilage oligomeric matrix protein/thrombospondin-5 (COMP), TNC, and N-cadherin (CDH2, CD325) (FIG. 4$b$). SPP1 is an established JUN target gene and has specifically been associated with JUN-mediated hepatic fibrosis. COMP, a non-collagen ECM protein, and TNC are both upregulated in the context of pulmonary fibrosis, which JUN signaling also mediates. JUN is an important transcription factor in cardiac fibrosis, in which COMP is upregulated. COMP is also known to be highly induced in skin fibrosis and specifically involved in collagen secretion. As such, these upregulated EMT-pathway genes represent likely targets by which JUN+/PDGFRA+ fibroblasts induce adhesions.

Other fibrosis-associated gene sets enriched in mouse adhesion fibroblasts include 'Regulation of Response to Wound Healing', 'Positive Regulation of Cell Proliferation', and 'Positive Regulation of Cell Differentiation' (FIG. 16*a*). Furthermore, hypergeometric test of gene ontology (GO) terms revealed enrichment of cytokine production regulation, extracellular matrix (ECM) organization, collagen fibril organization, endopeptidase activity, ECM structural constituents, growth factor binding, and metallopeptidase activity in mouse adhesion fibroblasts (FIG. 16*b*). qPCR assay confirmed upregulation of pro-fibrotic genes in adhesion forming fibroblasts including VIM and COL1A2 (FIG. 4*c*).

Figure 17:
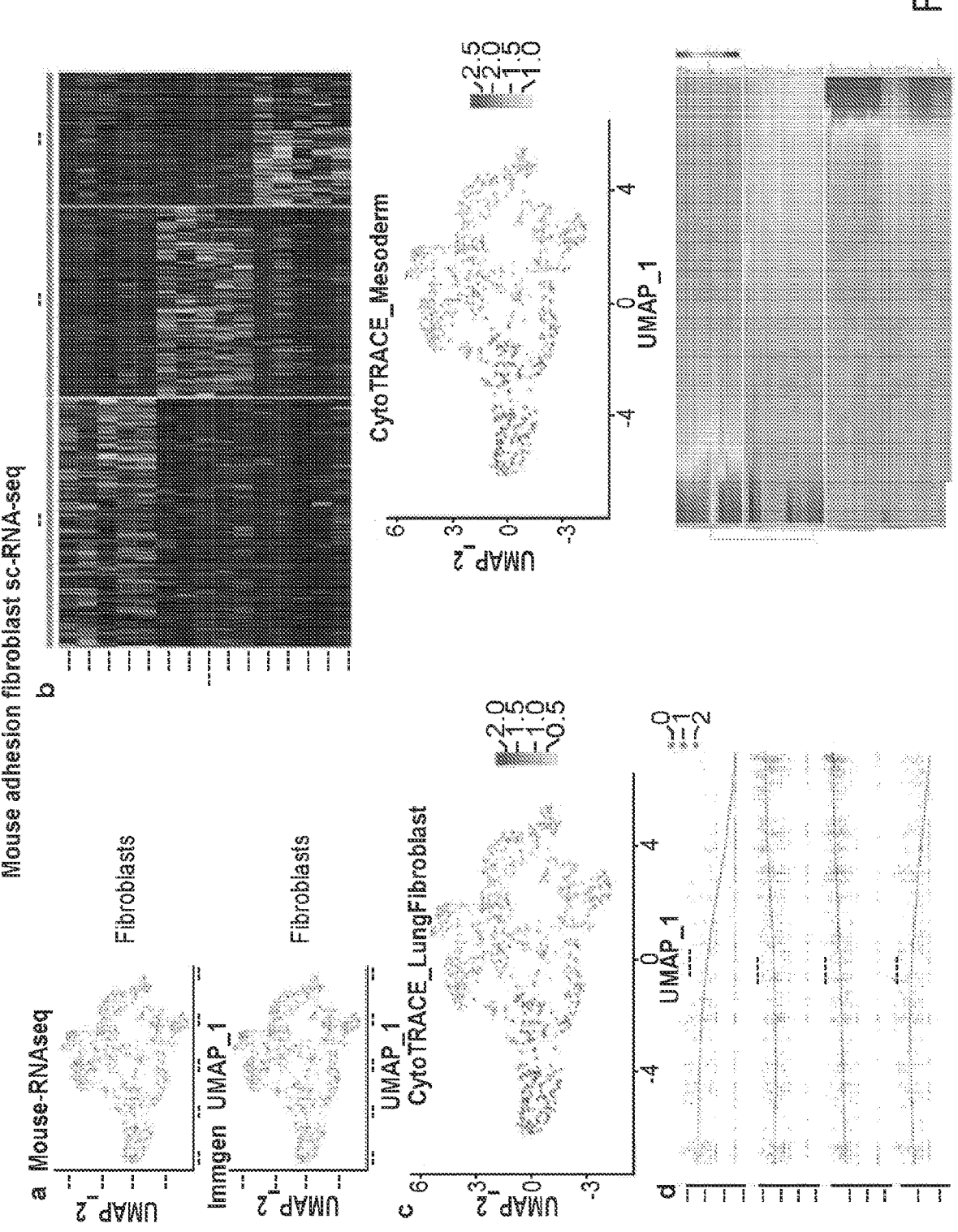
FIG. 17. Mouse adhesion fibroblast sc-RNA-seq. a, Mouse-RNAseq and Immgen objective analyses identify cell types (fibroblasts) represented in mouse adhesion fibroblast scRNA-seq data. Cell types as labelled by colors. b, Heatmap showing differential gene expression patterns based on clusters (FIG. 4*d*). Colors and numbers represent clusters along top of panel, most differentially expressed genes labelled at left. c, CytoTRACE analysis of mouse scRNA-seq data using lung fibroblasts (left panel) and mesoderm (right panel) datasets for reference. d, Pseudotime (Monocle 2) trajectories plot for mouse scRNA-seq data (left panel, for the following genes, from top to bottom: ASMA, JUN, PDGFRA, FSP1, colors indicate clusters from FIG. 4*d*) and heatmap (right panel, clusters from FIG. 4*d* noted on left, most significant genes displayed along right axis). e, Mouse scRNA-seq data UMAP feature plots for the following genes, from top to bottom and right to left: JUN, ASMA, STAT3, PDGFRA, IL6, FSP1. Cluster 1 highlighted in grey.
Figure 17:
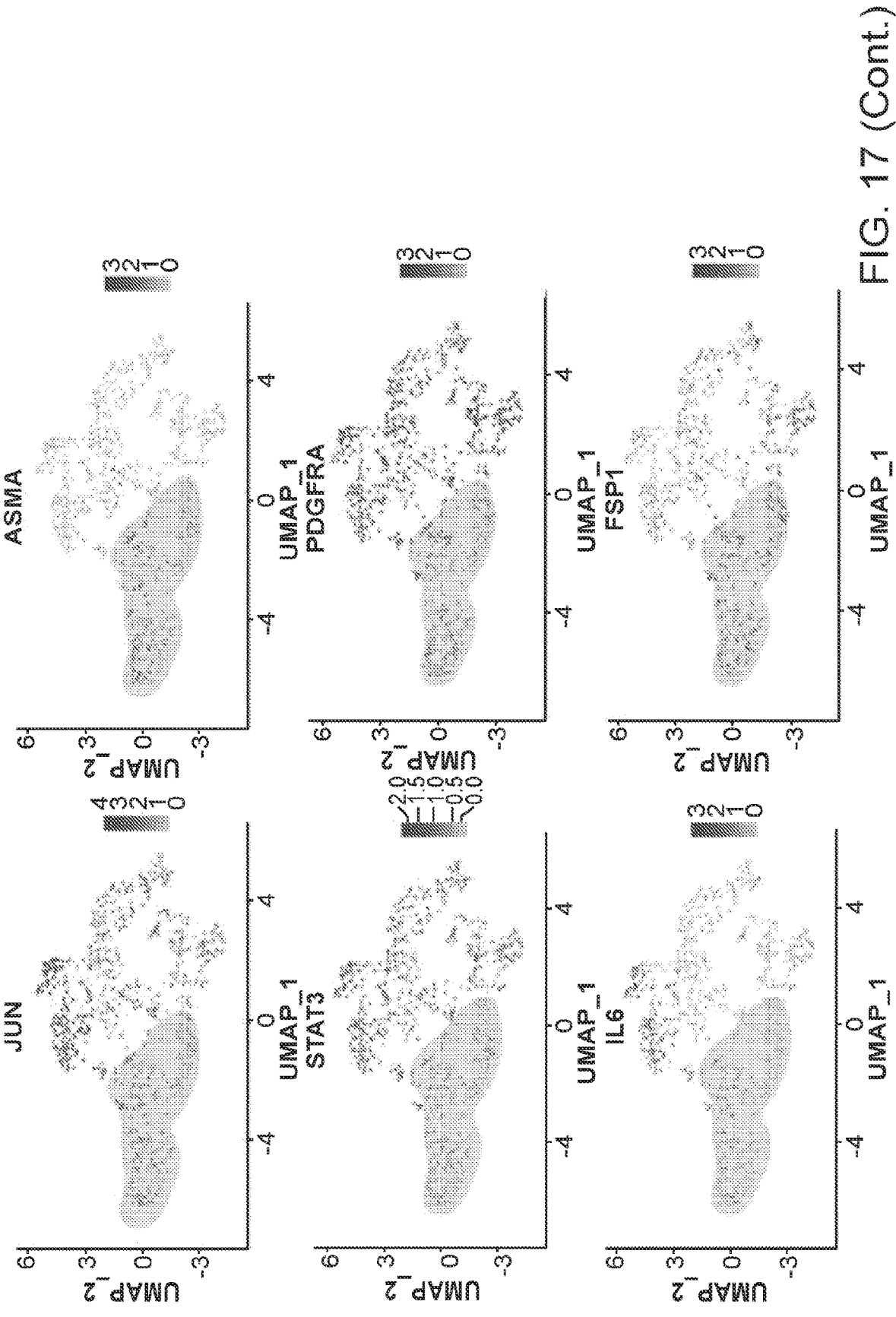

To explore fibroblast heterogeneity in the context of abdominal adhesions, we FACS-isolated mouse adhesion fibroblasts using the aforementioned, unbiased, lineage-negative based sorting strategy and conducted single cell (sc) RNA-seq. Adhesion fibroblasts from each of two time-points (POD 2 and POD 7) were analyzed using the 10× Genomics platform. Our findings demonstrate three unique clusters among pooled fibroblasts (FIG. 4*d*), with heterogeneous gene expression observed among fibroblasts from each timepoint (FIG. 4*e*, FIG. 17*a-b*). The heterogeneity appears greater among the fibroblasts from POD 2 compared to POD 7 (FIG. 4*e*).

Figure 9:
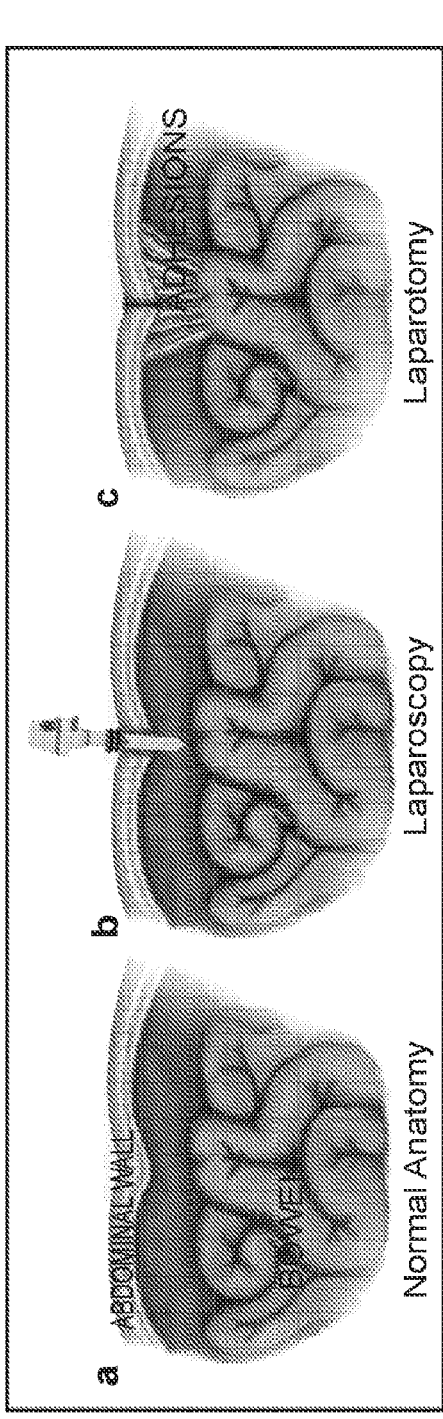
FIG. 9. Surgical schematic showing adhesions forming primarily after open laparotomy. a, Schematic of uninjured abdominal anatomy. b, Schematic of laparoscopic abdominal surgical intervention; adhesions rarely form following isolated parietal peritoneal injury. c, Schematic showing the abdomen following open laparotomy; abdominal adhesions have formed tethering a loop of bowel (visceral peritoneum) to the parietal peritoneum.
Figure 18:
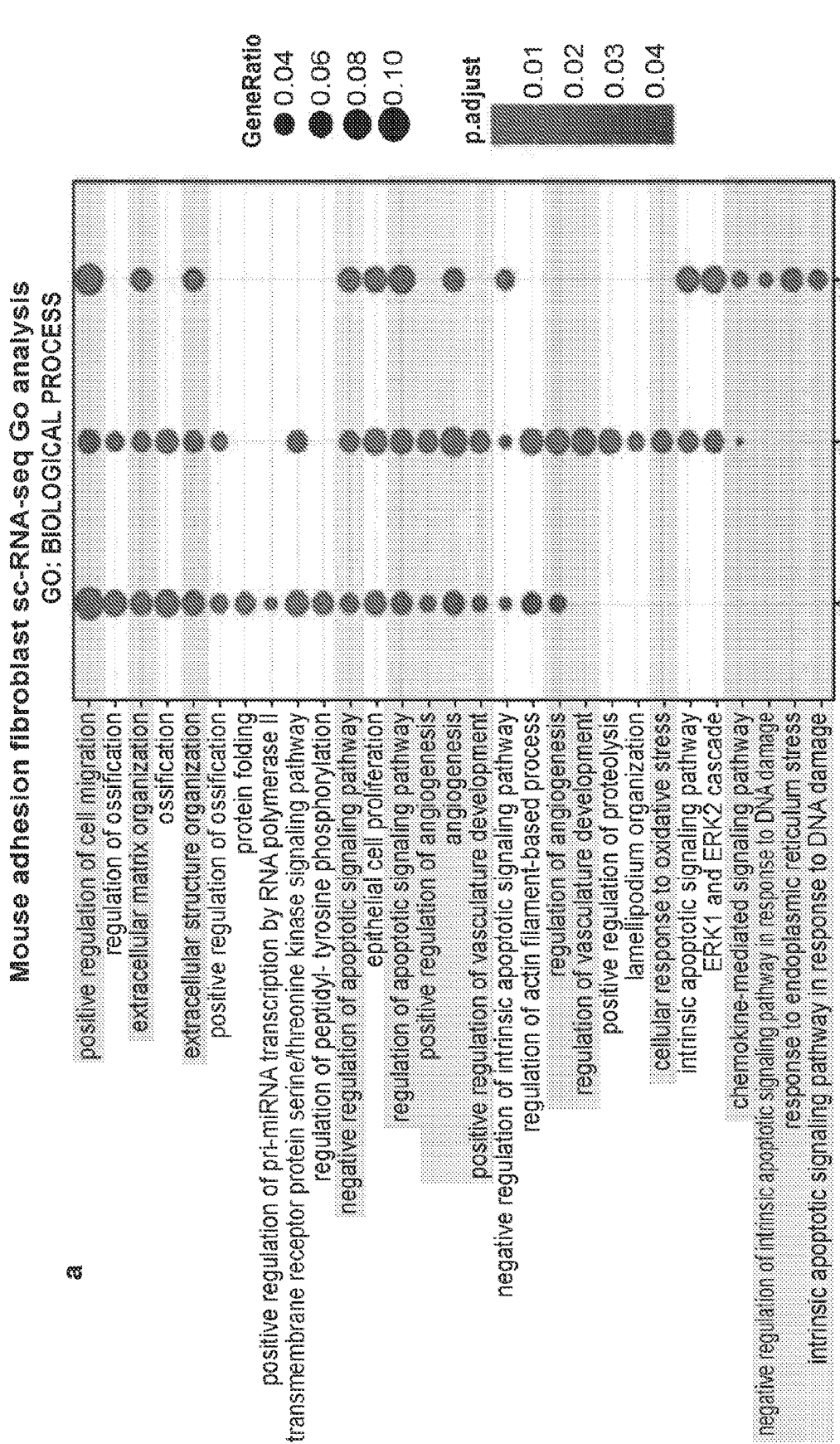
FIG. 18. Mouse adhesion fibroblast sc-RNA-seq GO analysis. a-b, GO term analysis for mouse sc-RNA-seq dataset. Terms and statistics as noted in figure panels. Colors used to highlight specific processes and components correlate with cluster colors used in FIG. 4*d*.
Figure 18:
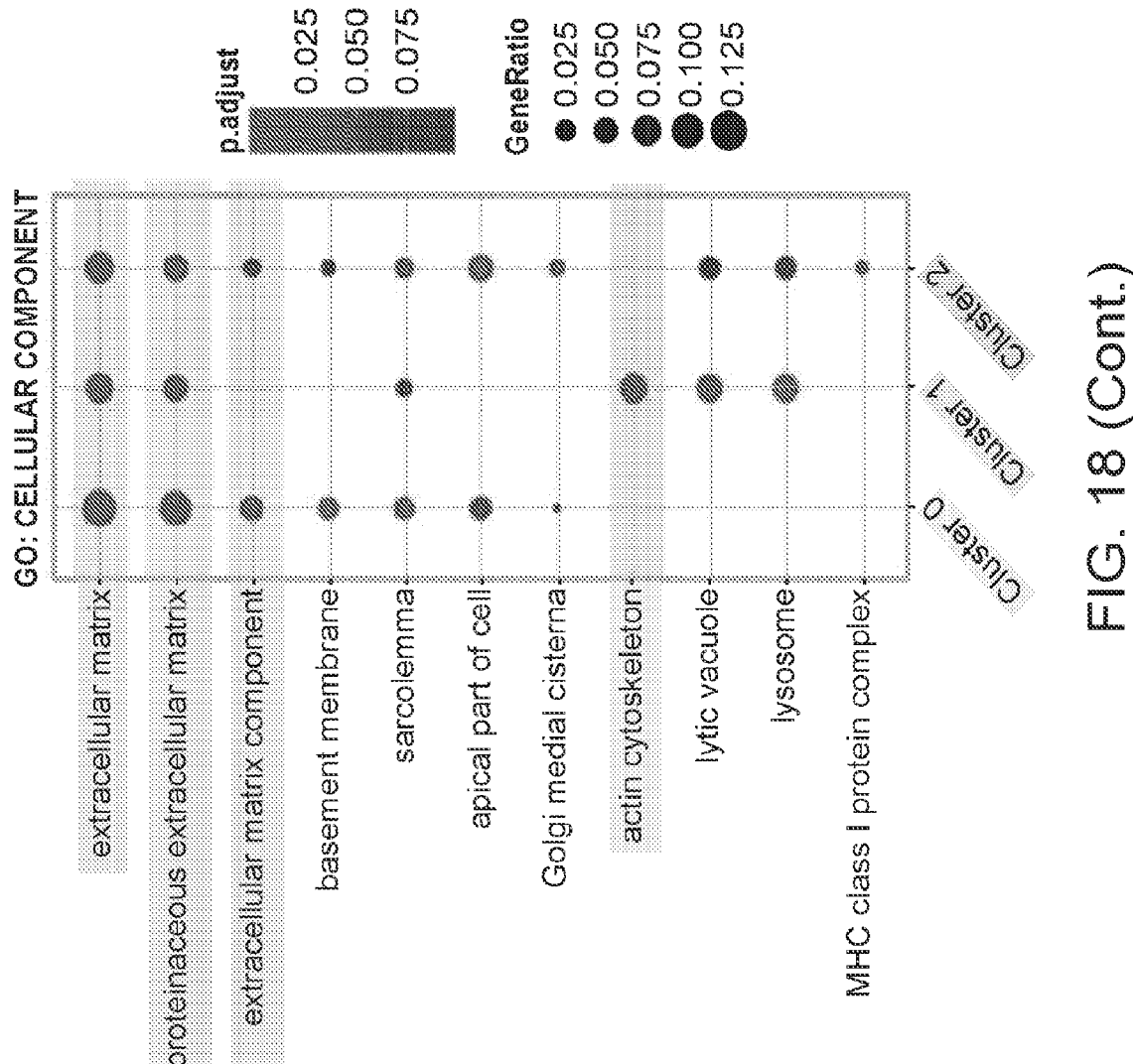

Next, we performed differentiation analysis using CytoTRACE, which is a novel tool that catalogues cells based on developmental potential in the context of transcriptional diversity. Using mouse lung fibroblasts and human mesoderm datasets for reference, this computational tool identified a clear lineage trajectory stemming from cluster 1—represented primarily by POD 2 adhesion fibroblasts (FIG. 17*c*). Next, we applied pseudotime analysis to further characterize the comparative properties of the identified fibroblasts subpopulations.$_{30}$ In line with the CytoTRACE results, we observe a clear pseudotime trajectory from cluster 1 with significant differences observed between the timepoints evaluated—POD 2 versus POD 7—in the mouse abdominal adhesion formation process (FIG. 4*f*). We explored the specific gene expression changes involved with this trajectory and found that JUN is activated early at POD 2 (cluster 1) and expression is maintained throughout, suggesting that there may be a persistent, JUN+, profibrotic state obtained for adhesion fibroblasts once activated (FIG. 4*h*, FIG. 17*d*9 *e*). STAT5 and ASMA are expressed primarily in cluster 1 in parallel with JUN activation (FIG. 4*g*). STAT3, FSP1, and MCP1, are strongly expressed by fibroblasts in all clusters, particularly cluster 1, supporting these as prominent factors in the signaling pathways by which JUN signaling promotes fibrosis (FIG. 4*h*, FIG. 17*d-e*). Interestingly, PDGFRA expression appears activated alongside JUN by cells in cluster 1 and shows progressively increasing expression through clusters 0 and 2, supporting our protein findings implicating a role for PDGFRA+ fibroblasts in adhesion progression (FIG. 4*h*, FIG. 17*d-e*). Gene Ontology (GO) enrichment analysis of the mouse scRNA-seq data revealed enrichment of acute phase factors primarily in cluster 1 such as cellular response to oxidative stress, cell migration, as well as angiogenesis and vascular development. All clusters show enrichment for extracellular matrix organization, but this is highest in cluster 0, whereas cluster 2 shows most enrichment for chemokine-mediated signaling and regulation of apoptotic signaling (FIG. 18*a-b*). Taken together these analyses characterize the properties of the putative subpopulations identified on single-cell gene expression analysis and support our conclusion that JUN is an early instigator of abdominal adhesion formation that signals through several impactful pro-fibrotic pathways.

Figure 5:
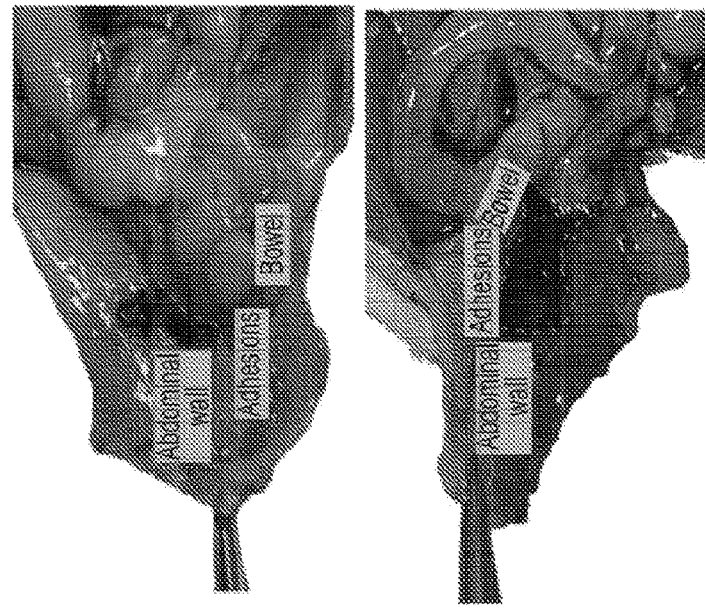
FIG. 5. Functional modulation of JUN signaling regulates adhesion formation a, Schematic illustrating the targeting construct used in the doxycycline (dox)-inducible JUN mouse model. In this construct, rtTA is expressed at the endogenous ROSA26 promotor. With dox induction, rtTA undergoes nuclear translocation to activate the Tet-responsive element (minCMV-tet(o)) driving expression of JUN. SA=splice acceptor, pA=poly(A) sequence. b, Representative phospho-flow cytometry analysis for phosphorylated (phospho-) JUN (left and middle panels), and phospho-STAT5 (right panel) expression in abdominal adhesion fibroblasts isolated from JUN mice 24 hours after adhesion surgery (with local induction with doxycycline at the time of adhesion formation) compared with vehicle control. n=3. c, Immunofluorescent assessment of phospho-JUN and phospho-STAT5 co-expression in mouse abdominal adhesion tissue. Thick white dotted line indicates edge of adhesions interface, coexpressing cells highlighted with thin white dotted lines. n=3. Scale bars, 25 μm. d, Quantitation of phospho-flow cytometry analysis showing a significant decrease in phospho-JUN (top panel) and phospho-STAT5 (bottom panel) expression with application of JUN inhibitor versus vehicle control in JUN mice at 24 hours. n=6. e, Representative gross images of mouse adhesions at POD 3 treated with (vehicle, DMSO) control (left panels) versus JUN-inhibitor (right panels). Adhesion interface highlighted in green, structures as indicated in figures, black sutures (circled with blue dotted line) visible on inhibitor specimens are nidus for adhesion formation (these are not visible on control specimens as they are covered with bowel that is adhesed to the abdominal sidewall). f, Gross assessment (using an adhesion severity grading score established by Tsai et al. 2018) of adhesion severity following in vivo inhibition of JUN using JUN inhibitor (T-5224) versus vehicle control in JUN (JUN expression induced with doxycycline in all JUN mice used) and wild-type mice at POD3. Data and error bars represent mean±SD. *P=0.01, P=0.0001, *P=0.01, **P=0.03, *P=0.0001, ****P=0.0001, unpaired two-tailed t test.
Figure 5:
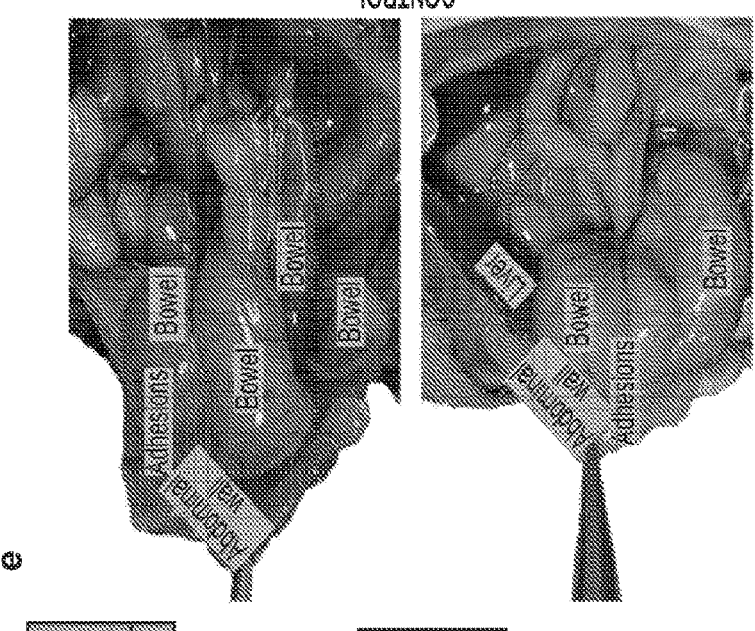
Figure 19:
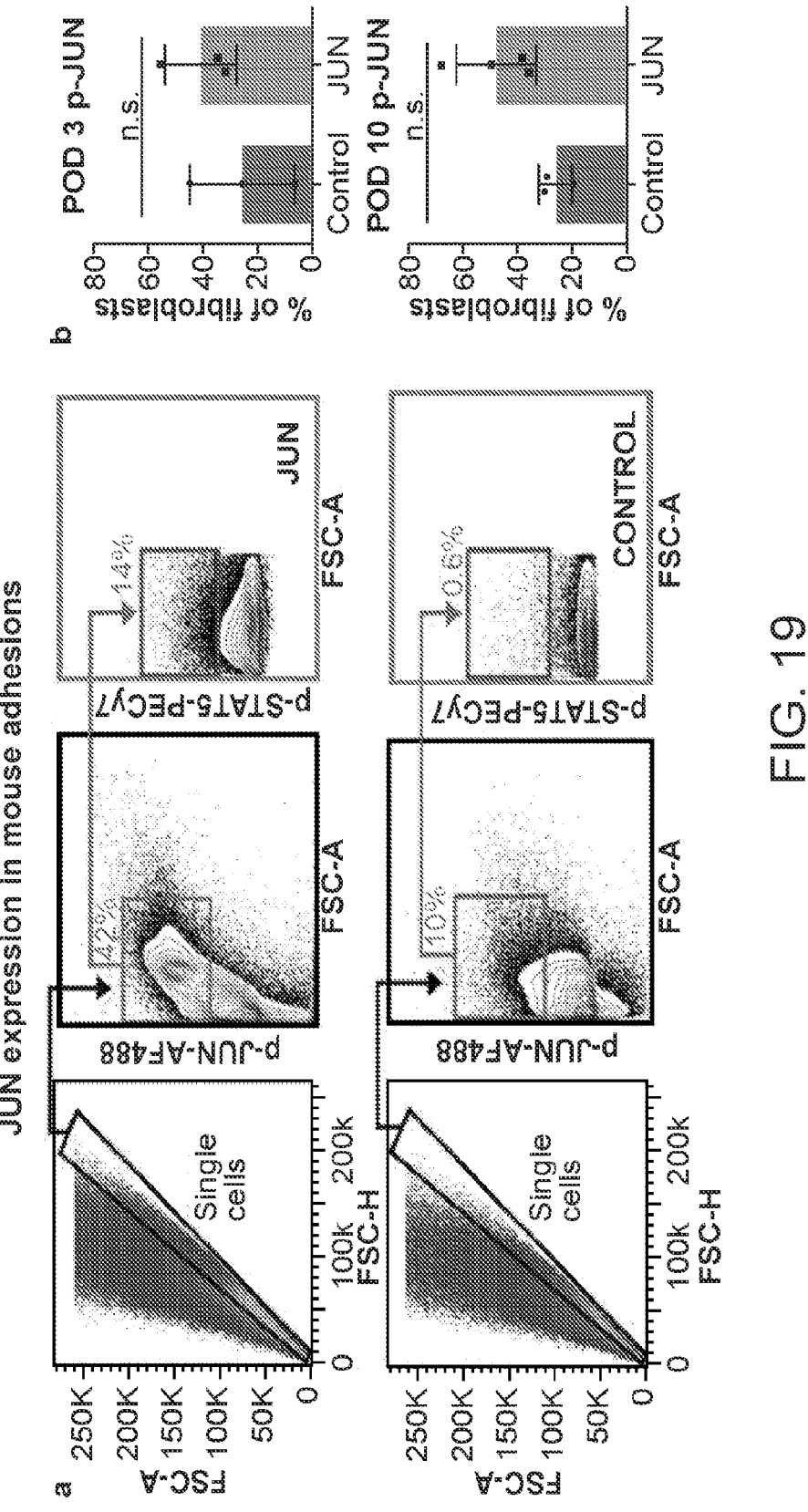
FIG. 19. JUN expression in mouse adhesions. a, Representative phospho-flow cytometry analysis for phospho(p)-JUN and p-STAT5 expression in abdominal adhesion fibroblasts isolated from JUN mice induced locally with doxycycline at the time of adhesion formation (top panel) compared with vehicle control (bottom panel) at 24 hours after surgery. Quantification in FIG. 5. n=3. b, Quantification of phospho-JUN upregulation in abdominal adhesion tissue isolated from JUN mice induced locally with doxycycline at the time of adhesion formation compared with vehicle control, at POD3 and POD10. n.s.=not significant. n=3. Data and error bars represent means±SD. unpaired two-tailed t test.
Figure 20:
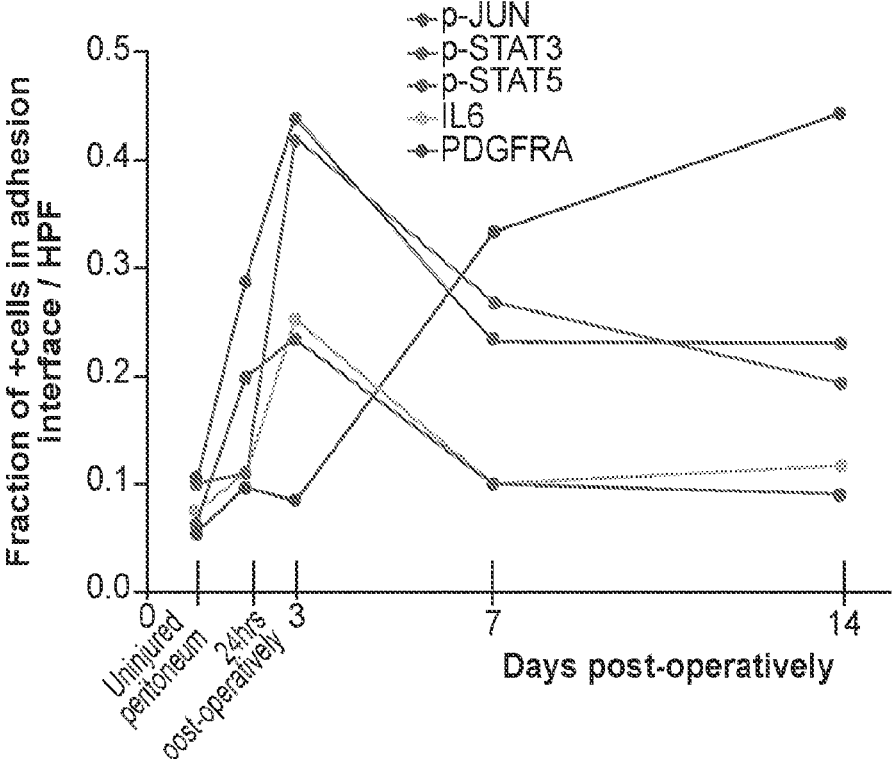
FIG. 20. Mouse abdominal adhesion tissues express JUN early and related pathways are activated. a, Quantitation (top panel, individual data points represent means) and representative immunofluorescent images (bottom panel) of tissue expression of p-JUN and related proteins (p-STAT3, p-STAT5, IL6, PDGFRA) in mouse abdominal adhesions at 24 hours, 3, 7, and 14 days post-operatively (post-op), compared with uninjured peritoneum control (left most panels). All protein expression in terms of immunofluorescent staining aside from PDGFRA, which is measured using the PDGFRAGFP mouse model. n=3. b, Individual data-points for data summarized in a, top panel. Data and error bars represent means±SD.
Figure 20:
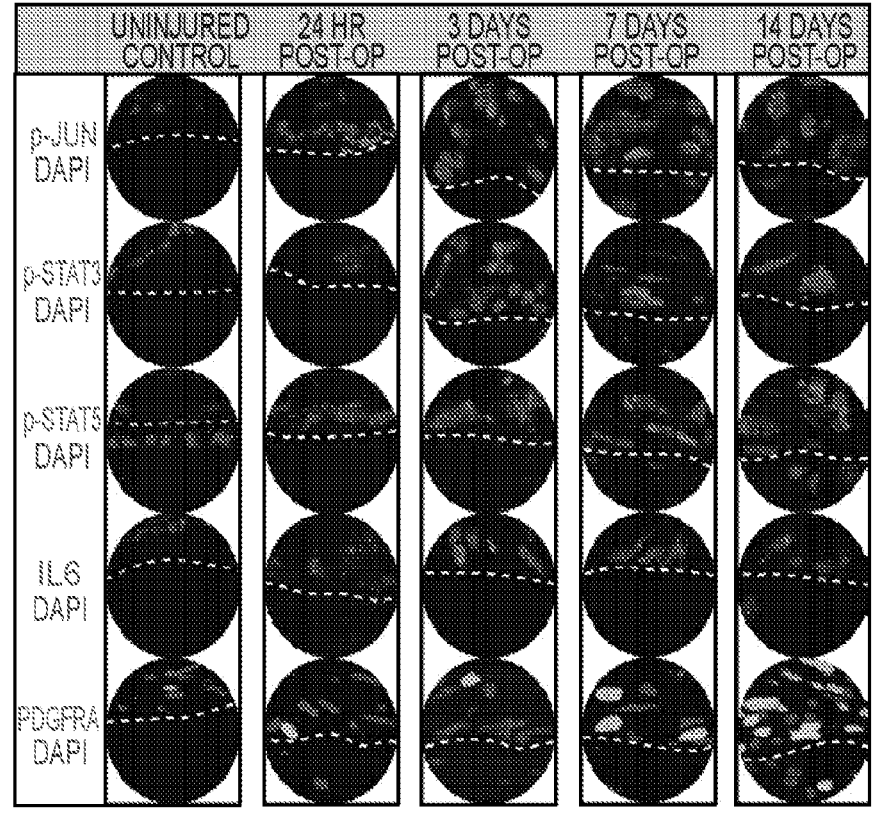
Figure 20:
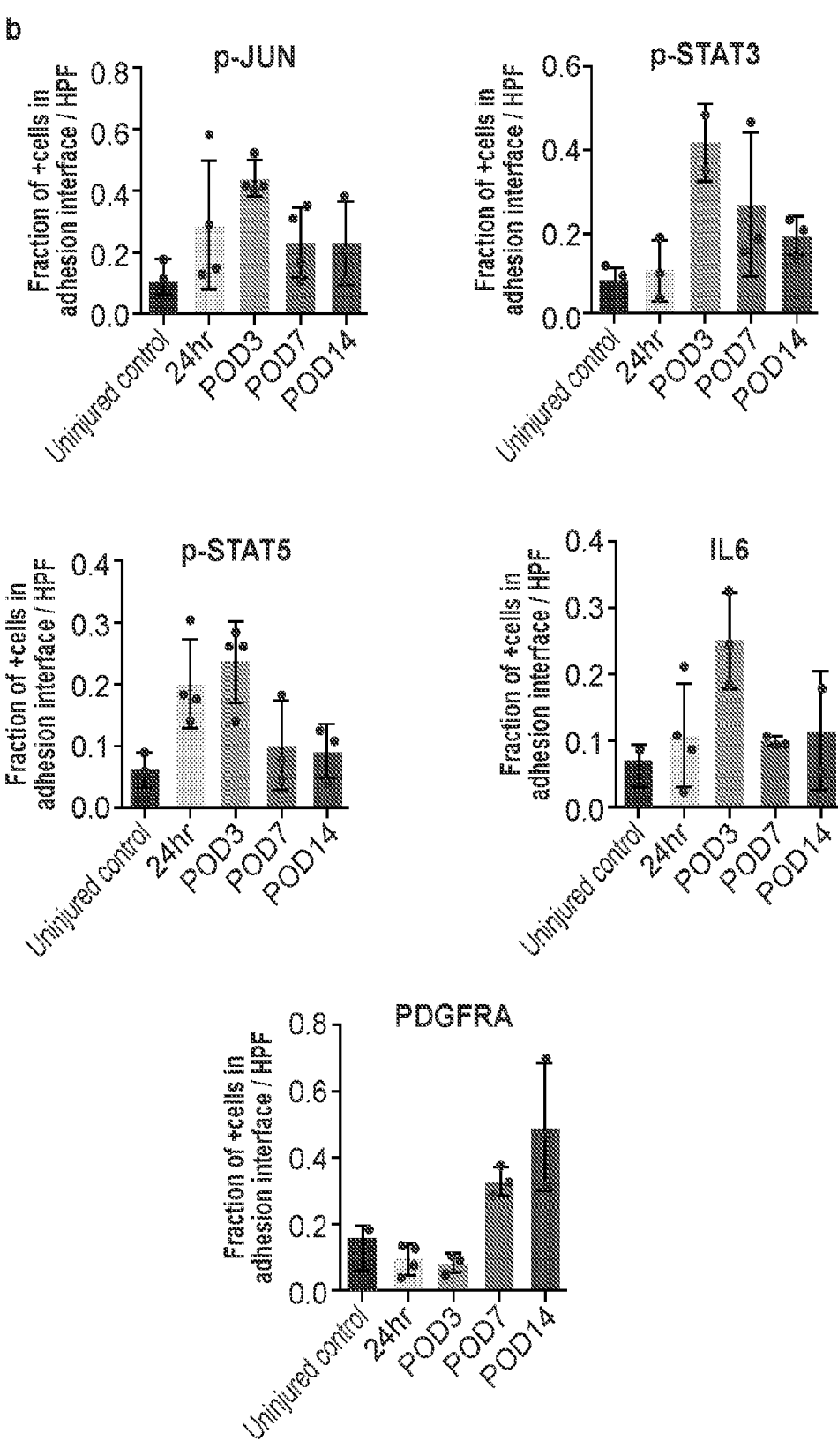
Figure 21:
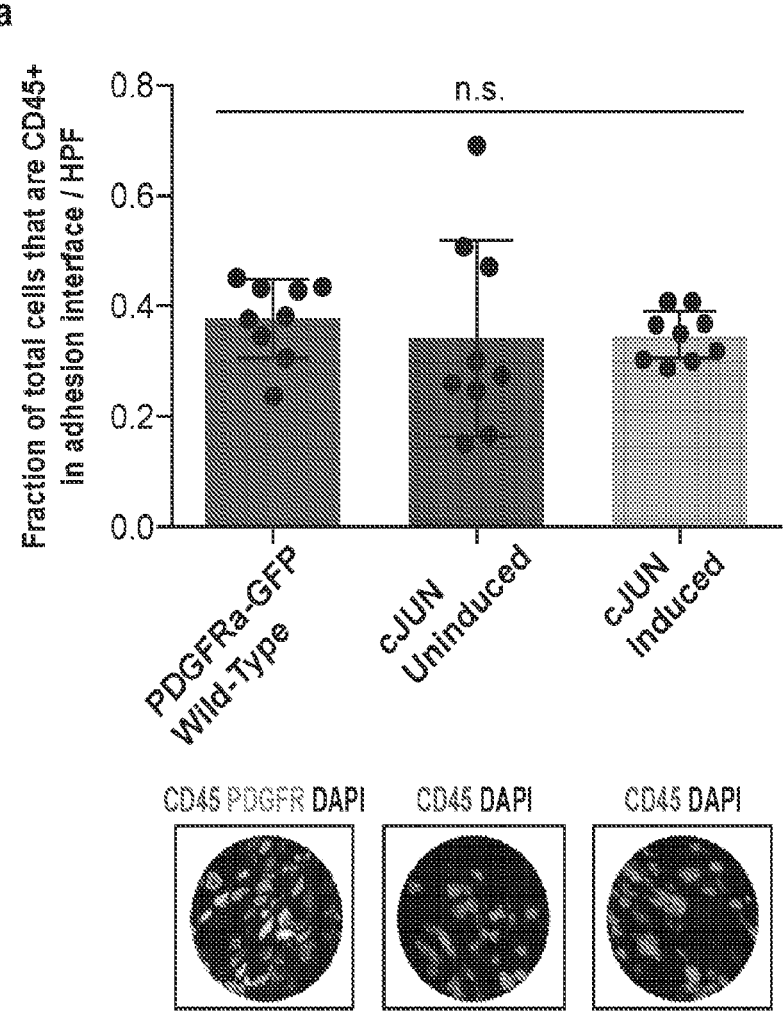
FIG. 21. JUN expression does not affect the number of CD45+ cells in the abdominal adhesion interface. a, Quantitation of CD45 expression in abdominal adhesion tissue samples from PDGFRAGFP (wild-type) mice (left panels), JUN mice—uninduced (middle panels), JUN mice—induced with doxycycline at the time of adhesion surgery (right panels). n=3. Data and error bars represent means±SD. n.s.=not significant. unpaired two-tailed t test.

JUN in an early promotor of abdominal adhesion fibrosis These results support that JUN activation might promote profibrotic pathway signaling in adhesions. To functionally validate this hypothesis, we conducted adhesion surgery on JUN mice (FIG. 5*a*), induced with doxycycline administered locally at the time of operation. As early as 24-hrs post-operatively, adhesion fibroblasts from induced JUN mice expressed significantly increased levels of phosphorylated (phospho-) JUN compared with vehicle control (FIG. 5*b*—left and middle panels, FIG. 19*a*). Phospho-JUN+ adhesion fibroblasts from induced JUN mice also expressed significantly increased phospho-STAT5 compared with control (FIG. 5*b*—right panel, FIG. 19*a*), indicating this as a signaling pathway through which JUN promotes fibrosis. Co-expression of phospho-JUN and phospho-STAT5 were confirmed histologically (FIG. 5*c*). JUN expression remains elevated in adhesion tissues from JUN mice at POD 3 and 10 (FIG. 19*b*). These findings were further validated at the tissue level. Immunofluorescent staining of mouse adhesion specimens over time shows that JUN expression is activated very early following injury (surgery), followed closely by increases in STAT3 and STAT5 expression (similar to our transcript level findings), as well as IL6, and then PDGFRA expression is activated with JUN and increases more gradually over time (FIG. 20*a-b*). While JUN signaling appears to have a dramatic effect on the recruitment and activities of fibroblasts in the context of abdominal adhesions, although JUN is expressed by other cells (for example, immune cells), JUN expression does not affect the number of CD45+ cells in the adhesion interface (comparing tissues from PDGFRA-GFP (wild-type) and JUN (induced and control) mice, FIG. 21*a*).

Figure 6:
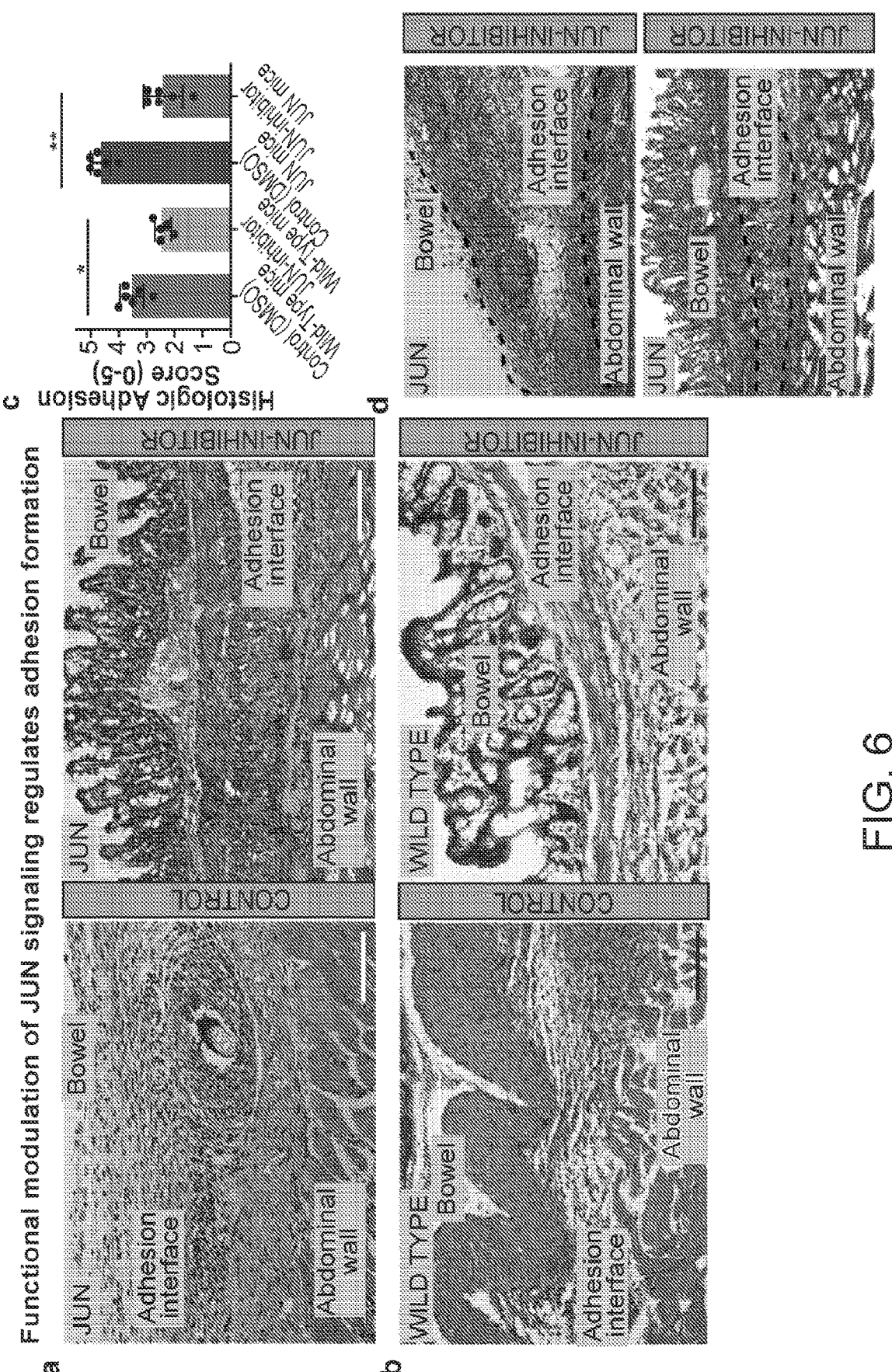
FIG. 6. Functional modulation of JUN signaling regulates adhesion formation a-b, Representative H&E sections for vehicle control (left panels) and JUN-inhibitor treated (right panels), in JUN (JUN expression induced with doxycycline in all JUN mice used) (a) and wildtype (b) mice. Adhesion interfaces outlined with green dotted lines. Structures as labelled in figure. Scale bars, 100 μm. c, Histologic scoring (as used in FIG. 1b) of adhesion tissue following in vivo inhibition of JUN using JUN inhibitor versus vehicle control in JUN (JUN expression induced with doxycycline in all JUN mice used) and wild-type mice. d, Representative images of trichrome staining of JUN mouse vehicle control (top panel) and JUN-inhibitor treated adhesion specimen (bottom panel). JUN expression induced with doxycycline in all JUN mice used. Adhesion interface outlined with black dotted lines. Structures as labelled in figure. n=5. Conditions and structures at noted in figure panels. Scale bars, 100 μm. e, Representative figures showing IF staining for phospho-JUN and PDGFRA in adhesion tissue following in vivo inhibition of JUN (using JUN inhibitor, T-5224) in JUN (JUN expression induced with doxycycline in all JUN mice used) mice. Conditions and structures at noted in figure. Scale bars, 50 μm. f, Quantification of p-JUN+ cells in i. HPF=high power field. n=3. Data and error bars represent mean±SD. *P=0.0002, P=0.0001, *P=0.0001, unpaired two-tailed t test.
Figure 6:
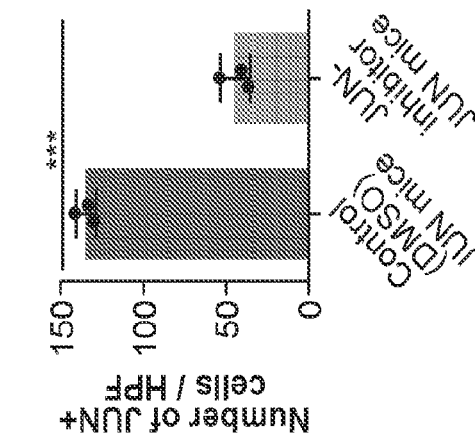
Figure 6:
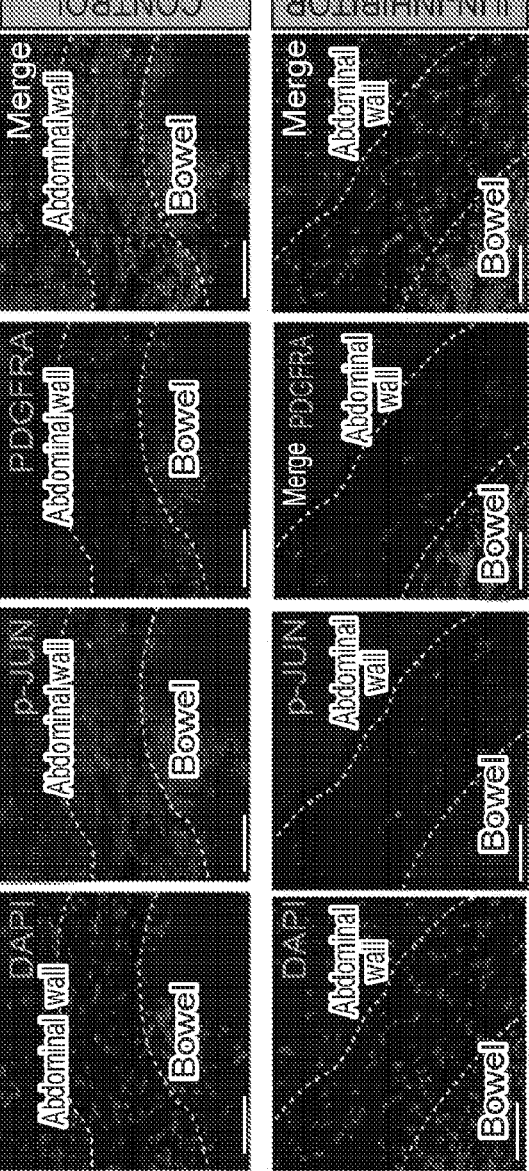
Figure 22:
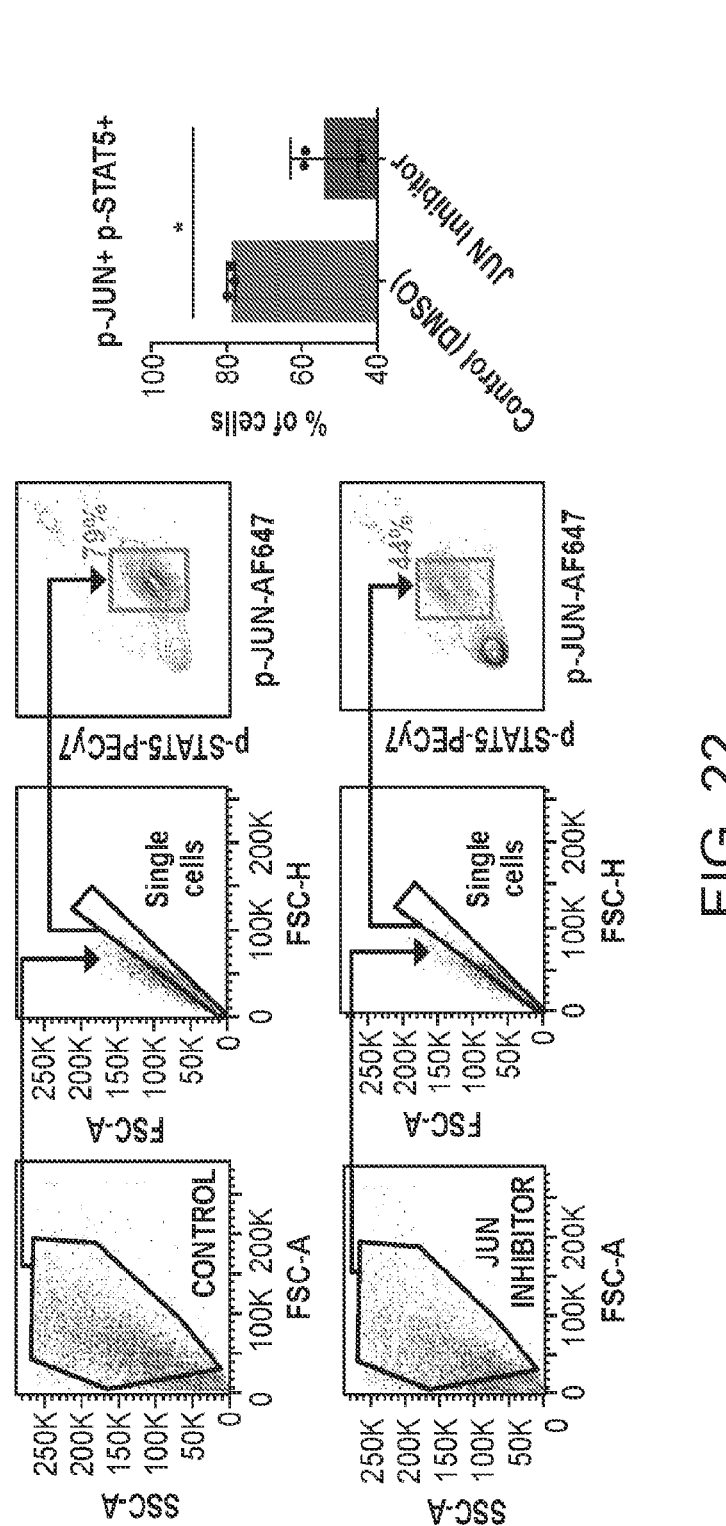
FIG. 22. T-5224 suppresses JUN and STAT5 expression in mouse fibroblasts in vitro and in vivo. a, Representative phospho-flow cytometry analysis for phospho-JUN and phospho-STAT5 expression in mouse adhesion fibroblasts treated with JUN inhibitor in vitro versus vehicle control, quantitation (right panel). n=3. b, Representative phospho-flow cytometry analysis for phospho-JUN and phospho-STAT5 expression in JUN mouse adhesions treated locally with JUN inhibitor in vivo versus vehicle control. Quantitation in FIG. 5. n=6. Data and error bars represent means±SD. *P=0.008, unpaired two-tailed t test.
Figure 22:
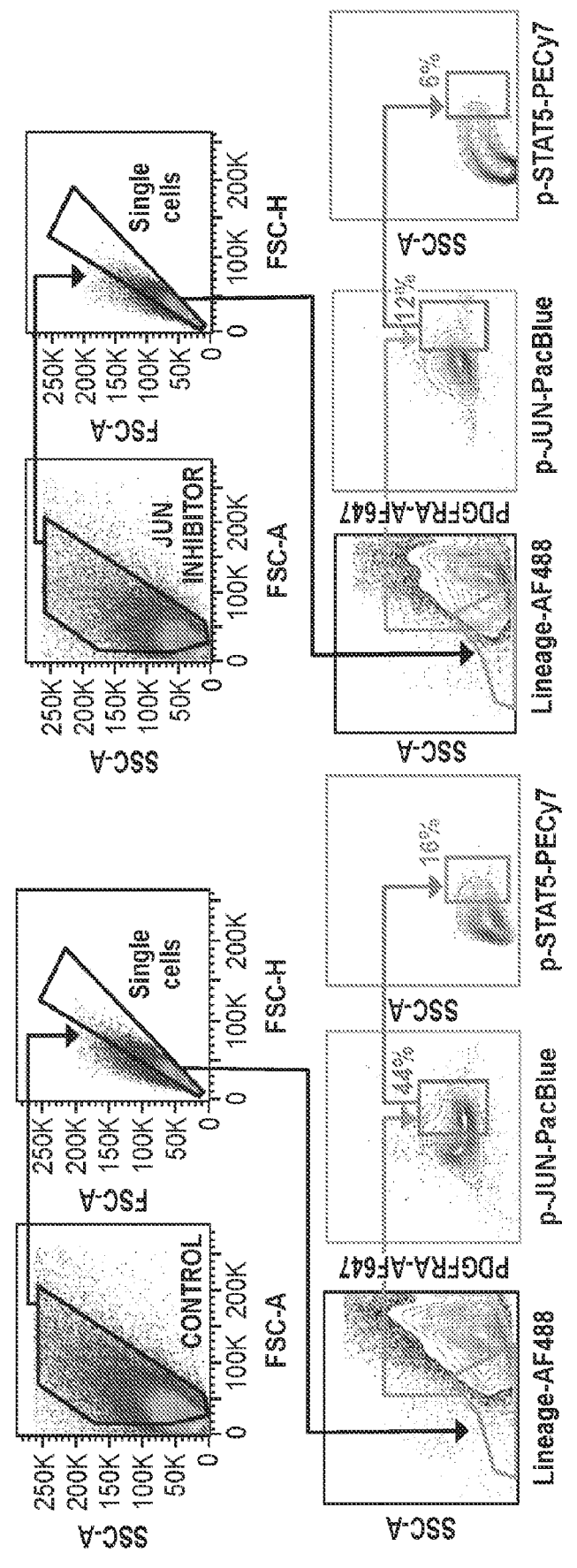

Functional modulation of JUN signaling regulates adhesion formation Given these findings, we wondered if functional modulation of JUN signaling may affect adhesion formation. T-5224 is a selective, small molecule AP-1 inhibitor. When JUN signaling in mouse adhesion fibroblasts was suppressed using T-5224, phospho-JUN and phospho-STAT5 expression were significantly reduced in vitro using freshly isolated mouse adhesion fibroblasts (FIG. 22*a*). When this inhibitor was applied intra-abdominally in vivo (in wild-type and JUN mice), phospho-JUN and phospho-STAT5 expression were significantly decreased (FIG. 5*d*, FIG. 22*b*). Grossly, we saw a dramatic decrease in adhesion formation with application of this JUN inhibitor (FIG. 5*e-f*). Histologically, the adhesions were significantly thinner and less fibrotic with JUN inhibition (FIG. 6*a-d*). Co-suppression of JUN and PDGFRA were confirmed in this model, and decreased JUN expression with JUN inhibitor application was significant at the tissue level (FIG. 6*e-f*).

Figure 7:
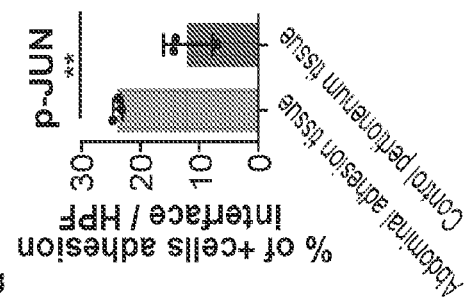
FIG. 7. Human tissue recapitulates adhesion biology and gene expression a, Human abdominal adhesion tissue histology (H&E—left, trichrome—middle, picrosirius red—right). Adhesion interface bounded by yellow dotted lines and labeled. n=5. Scale bars, 100 μm. b, On unbiased-FACS analysis, PDGFRA expression is significantly upregulated in human abdominal adhesion fibroblasts, compared with control peritoneum. CD26 expression is also upregulated, although not significantly. Conditions as labelled in figure. n=5. c, Representative IF staining of human abdominal adhesion tissue for JUN and PDGFRA, right panel is zoom of indicated region in white. Adhesion interface outlined with thick white dotted lines (left panel), co-localization of PDGFRA and JUN expression highlighted with thin white dotted lines (right panel). n=3. Scale bars, 50 μm. d, Quantitation of p-JUN+ cells in human abdominal adhesion tissue pictured in panel c, compared with human control peritoneum tissue. n=3. e, Representative IF staining of human abdominal adhesion tissue shows co-localization of PDGFRA with collagen 1 (COL1) and collagen 3 (COL3). Adhesion interface outlined with white dotted lines. Structures as labelled in figure. n=5. Scale bar, 50 μm; 10× zoom at right. f. Quantitation of cytokine production (including IL6, MCP-1, PDGF-AA, and IL8) by fluorescent assessment of the cell supernatant from primary human abdominal adhesion fibroblasts in vitro, measured 24 and 48 hours after isolation. Values normalized to cell-free media for each cytokine assessed. MFI=Median Fluorescence Intensity. n=3. Conditions as labelled in figure. g, PCA plot of human bulk RNA-seq data shows distinct clustering of human fibroblast specimens FACS-isolated from human abdominal adhesion (n=6) and control peritoneal tissues (n=3) (colors as indicated, variances noted on plot). h, Heatmap of human adhesion-forming fibroblasts shows significant differential gene expression between conditions. Highly expressed EMT and JUN kinase GSEA pathway genes highlighted in yellow and blue panels, respectively, at right. Color key and histogram at far right. *P=0.02, **P=0.0078, unpaired two-tailed t test.
Figure 7:
Figure 7:
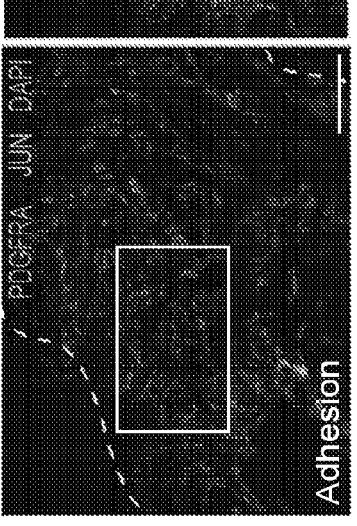
Figure 7:
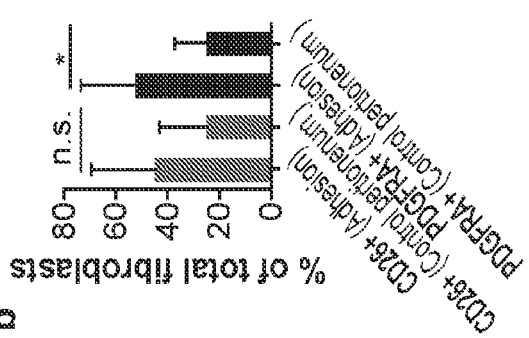
Figure 7:
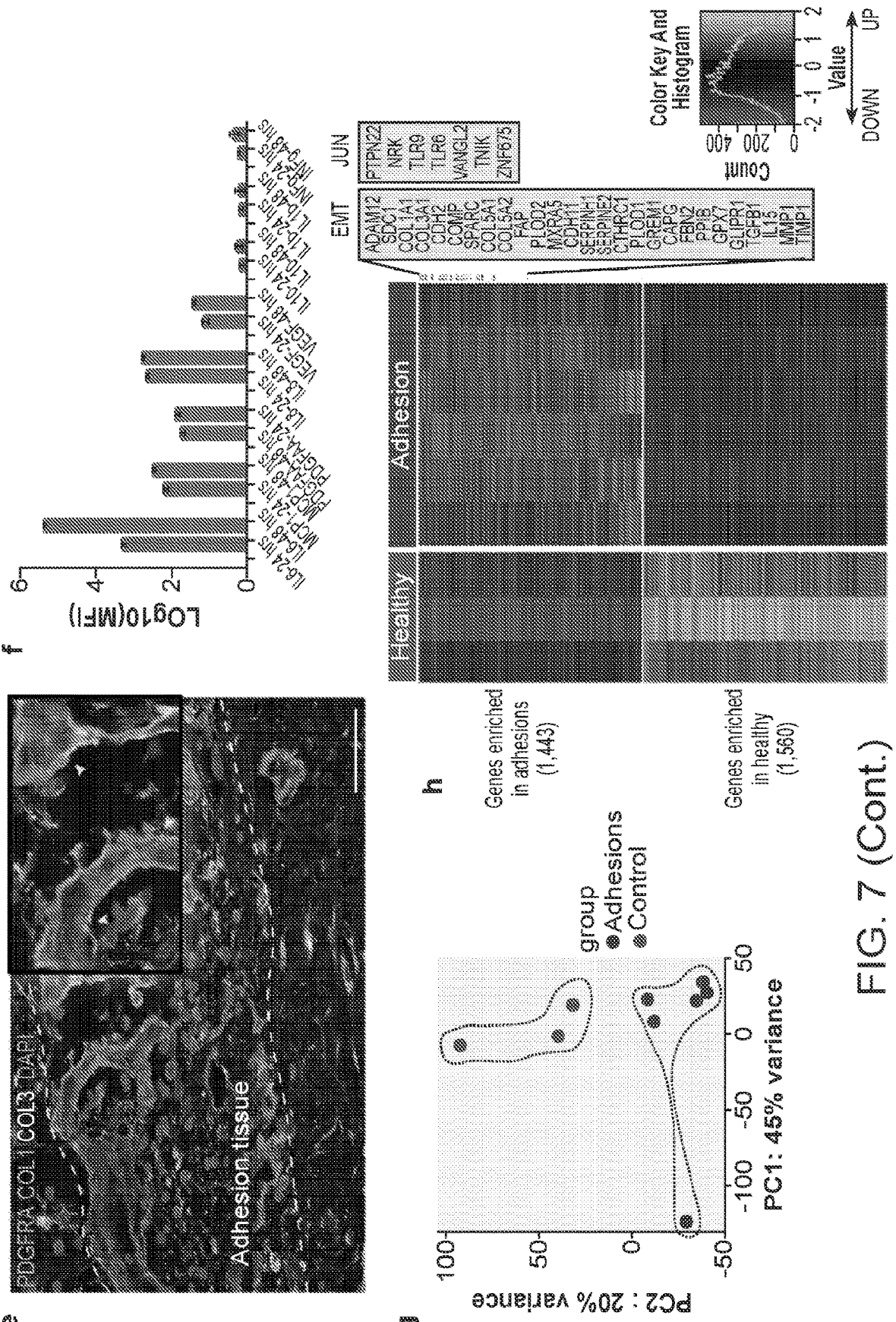
Figure 23:
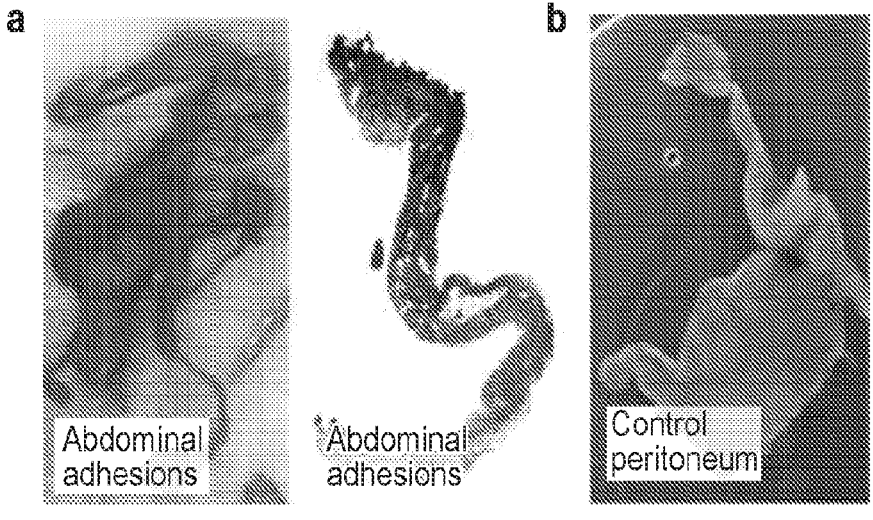
FIG. 23. Images of human abdominal adhesions specimens. a, Gross image of human abdominal adhesion tissue (left panel), stitched histologic image of human abdominal adhesion tissue stained with trichrome (right panel). n=21. b, Gross image of control human peritoneum tissue. n=10.

Human tissue recapitulates adhesion biology and gene expression Next, we explored these results in human abdominal adhesions. We collected 24 adhesion tissue specimens from patients with a history of one or more prior abdominal surgical procedure(s) (FIG. 23*a*) and 10 control peritoneum specimens from patients who had not undergone prior surgery (FIG. 23*b*). Human adhesions histologically resemble mouse adhesions on H&E (FIG. 7a—left panel). Trichrome staining shows prominent collagen throughout the adhesions (FIG. 7a—middle panel, FIG. 23a), and picrosirius red staining shows mature collagen fibers with primarily linear organization (FIG. 7a—right panel). JUN is expressed in human adhesion tissue, similar to what is seen in mouse tissue (FIG. 7c-d).

Figure 24:
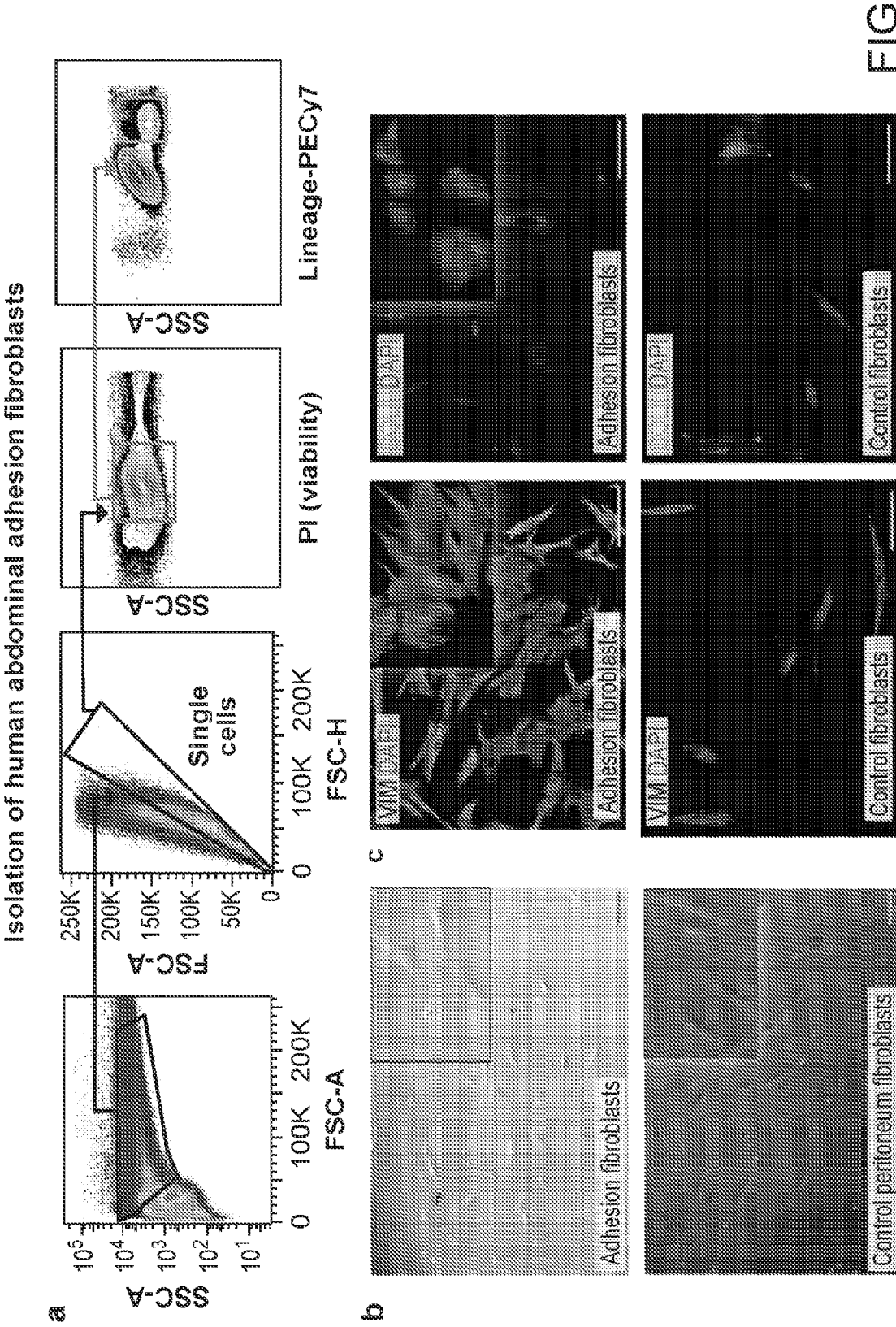
FIG. 24. Isolation of human abdominal adhesion fibroblasts a, Representative plots illustrating unbiased FACS isolation strategy for sorting human abdominal adhesion fibroblasts. b, In vitro imaging of FACS-isolated human fibroblasts from abdominal adhesions (left panel) (n=6) and control peritoneum (right panel) (n=3). Insets, zooms at right top; scale bars, 25 μm. c, FACS-isolated human abdominal adhesion fibroblasts (top panels, n=3) and human control peritoneal fibroblasts (bottom panels, n=3) staining for vimentin (VIM) and Collagen 1 (COL1) on immunocytochemistry. Insets, zooms at right top; scale bars, 25 μm.
Figure 25:
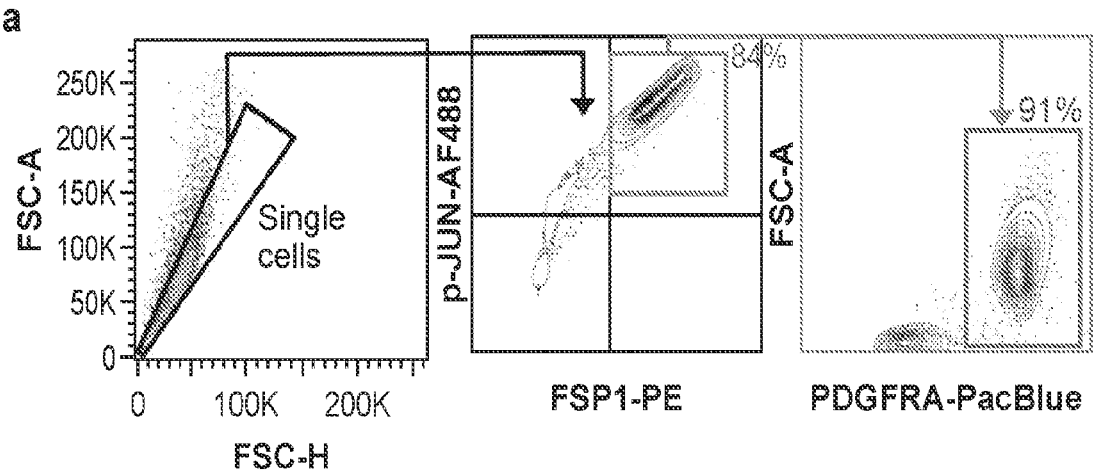
FIG. 25. Characterization of human abdominal adhesion fibroblast markers. a, Representative plots showing unbiased phospho-flow cytometry analysis of human adhesion fibroblasts for expression of phospho(p)-JUN, FSP1, and PDG-FRA (percentages of cells noted in corresponding color next to gates). b, Immunofluorescent staining of human abdominal adhesion tissue for phospho-JUN and FSP1 (top panels), phospho-JUN and MSLN (middle panels), ASMA and PDG-FRA (bottom panels). Adhesion tissue outlined with thick white lines, co-expressing cells highlighted with thin white lines, antibodies noted in top left corner of each panel, merge panels at far right. Scale bars, 50 μm. n=3.
Figure 25:
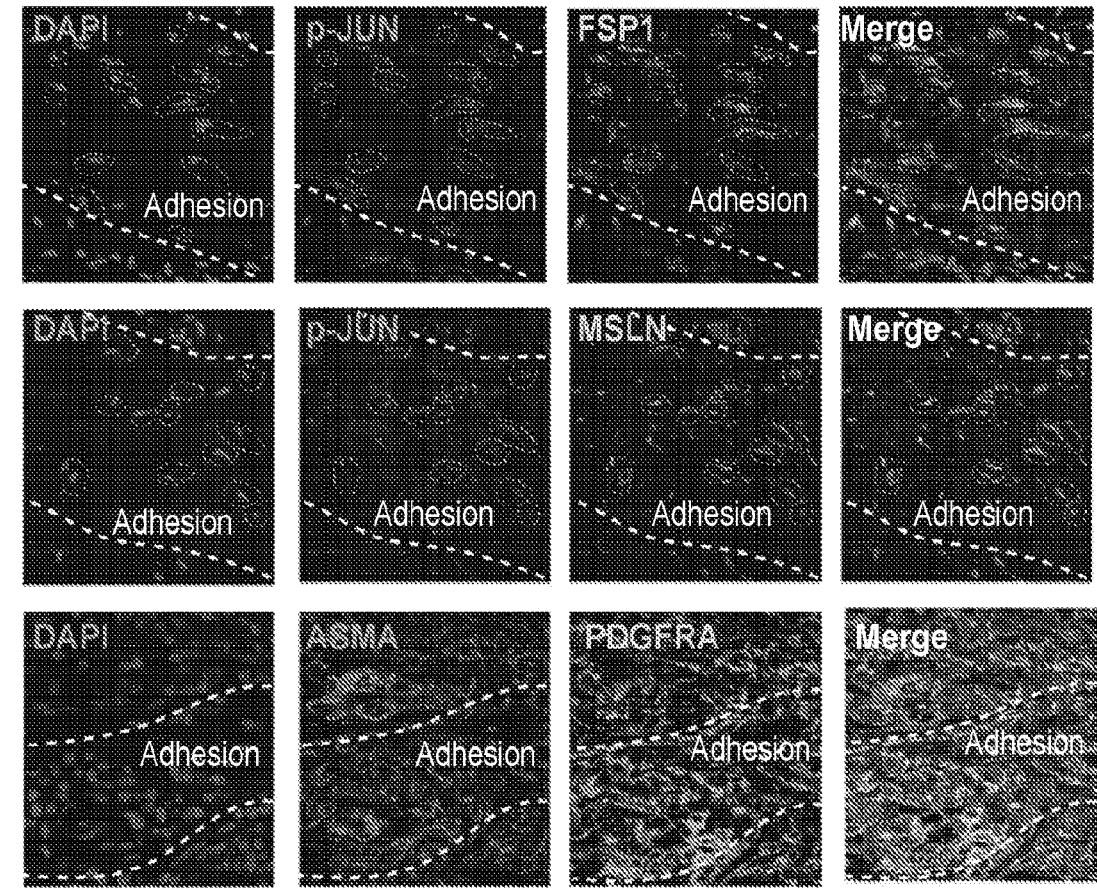

We FACS-isolated fibroblasts from human adhesion and control tissues using the aforementioned unbiased, lineage-based approach (FIG. 24a-b). Human adhesion fibroblasts strongly express VIM and COL1 on immunocytochemistry evaluation compared with control (FIG. 24c). Similar to mice, we found that the vast majority (mean 84.8%, SD 7.1) of JUN+ human adhesion fibroblasts expressed FSP1 (FIG. 25a-b—top panels). The vast majority of phospho-JUN+/FSP1+ also expressed PDGFRA (91%, SD 1.2) (FIG. 25a). Although, similar to the results in mice, there was a small population of PDGFRA+ fibroblasts that did not express JUN, indicating heterogeneity within the human adhesion fibroblast population. A minor portion of JUN+ fibroblasts also expressed MSLN, similar to mice (FIG. 25b—middle panels). We confirmed PDGFRA expression in human adhesion fibroblasts (FIG. 7b-c). PDGFRA-expression also co-localizes with ASMA (FIG. 25b—bottom panels). As such, as in mice, human adhesion fibroblasts can be identified by expression of JUN, PDGFRA, ASMA, and FSP1. At the tissue level, PDGFRA-expression co-localizes with COL1 and COL3 expression, showing that PDGFRA+ fibroblasts are directly involved in extracellular matrix production during adhesion formation (FIG. 7e).

We also analyzed the supernatant from freshly-isolated human abdominal adhesion fibroblasts in terms of cytokine production and found that adhesion fibroblasts primarily secrete IL6, MCP1, PDGF-AA, and also IL8 (FIG. 7f). This assay validates that while IL6 is initially secreted by a variety of cell types in the acute phase response to injury when adhesions first form, adhesion fibroblasts produce their own IL6 as part of a profound, chronic, profibrotic state. IL6 is a direct pathway signaling factor downstream from JUN, and PDGF-AA binds to fibroblast PDGFRA receptors stimulating cell proliferation, gene expression, and ECM production. MCP1 is also known to be secreted by fibroblasts in the context of fibrosis. Next, we explored human adhesion (Patients #7, 10, 15, 19, 21, and 23) versus control fibroblast gene expression using bulk RNA-seq. PCA shows separate clustering of adhesion and control (uninjured peritoneum) transcriptomes, with 65% of the variance explained by the first two components (FIG. 7g).

Figure 26:
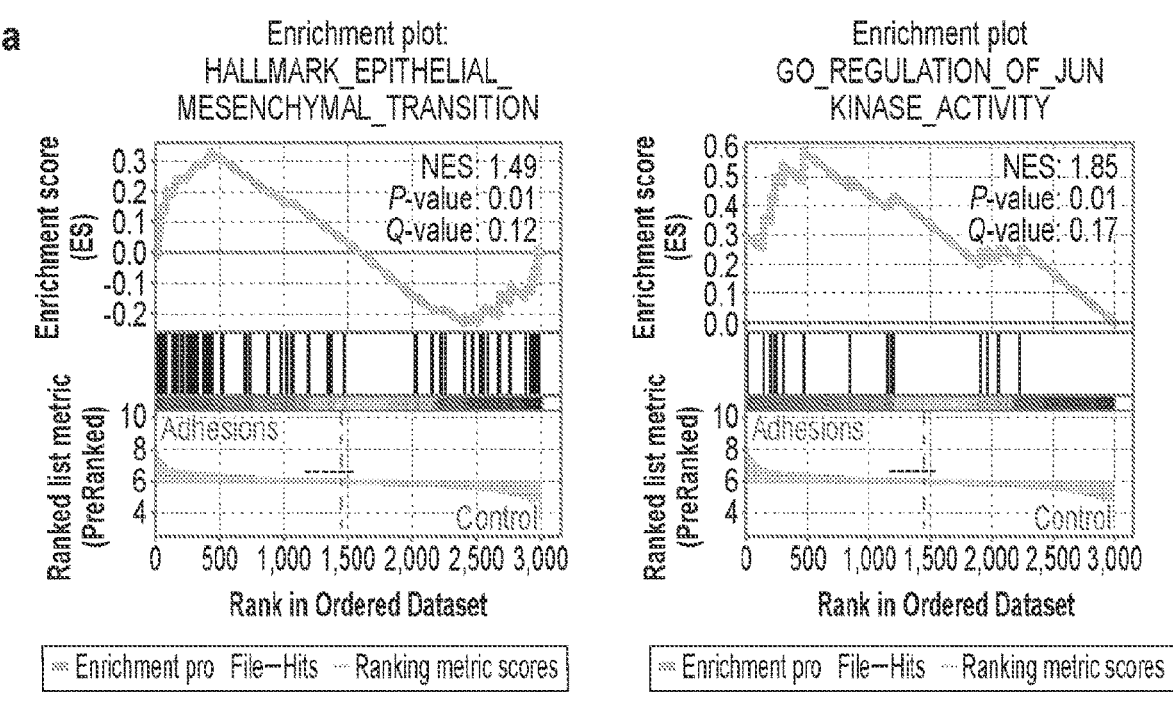
FIG. 26. Human adhesion fibroblast RNA-seq GSEA and GO analysis. a, GSEA of human adhesion fibroblast bulk RNA-seq data shows enrichment of 'EMT', 'JUN Kinase Activity', 'Extracellular Matrix Structural Constituent' and 'Collagen Trimer' pathways. NES, P and Q values noted in figure panels. b, Gene Ontology (GO) term analysis for human bulk RNA-seq dataset. Terms and statistics as noted in figure panels.
Figure 26:
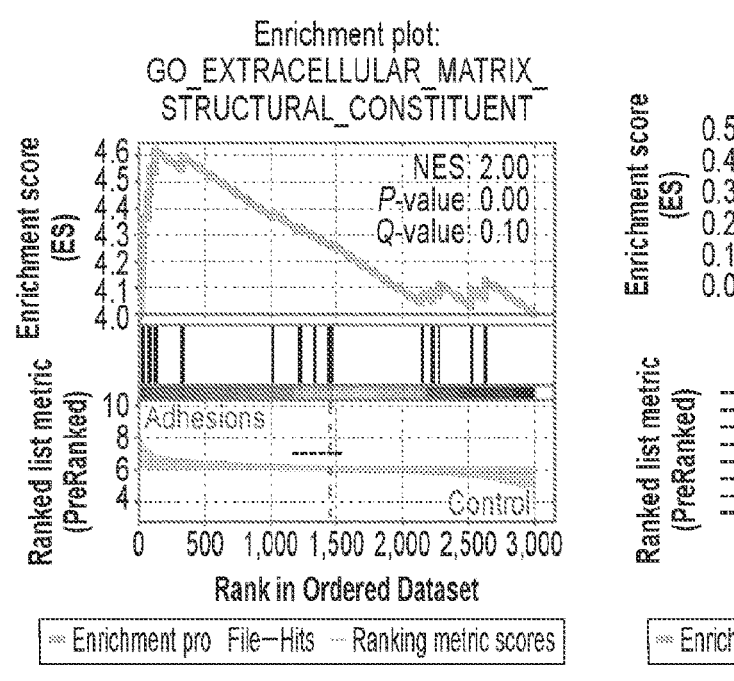
Figure 26:
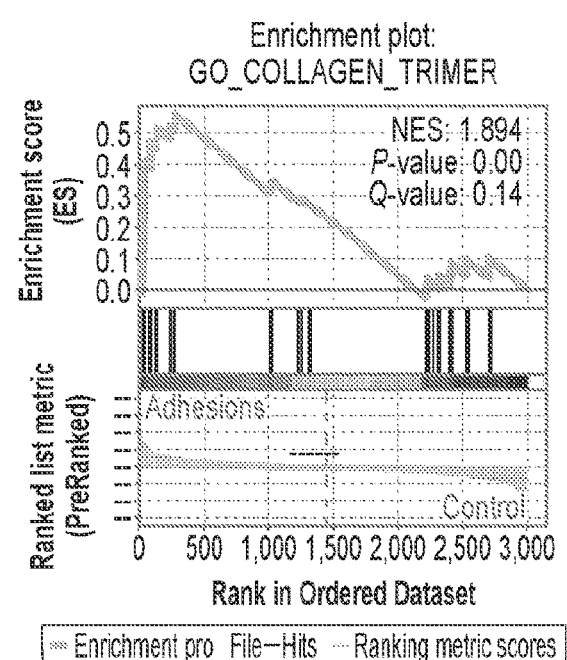
Figure 26:
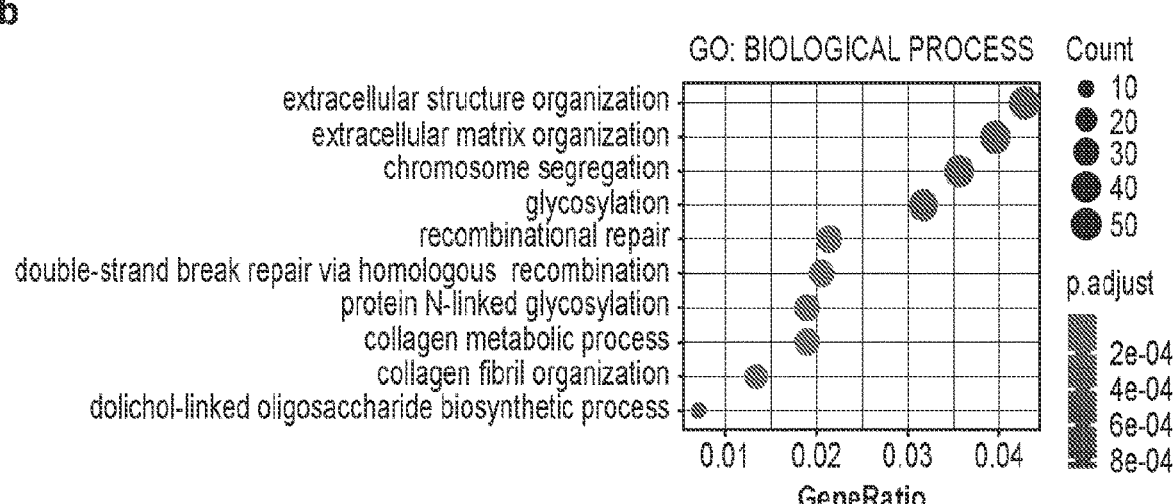

We then compared gene expression profiles of adhesion and control specimens. We identified 1443 genes that were significantly enriched in human adhesion fibroblasts and 1560 genes that were significantly enriched in control cells (FDR<0.01; FIG. 7h). On GSEA, one of the most significantly enriched molecular signatures in human adhesion fibroblasts was the EMT pathway, similar to mouse fibroblasts (FIG. 26a). Many of the genes noted in this pathway are associated with tissue fibrosis and were also found to be upregulated in our mouse RNA-seq data including COMP, TIMP-1, COL1A1, and COL3A1. The JUN kinase (JNK) pathway was also significantly enriched in human adhesion fibroblasts (FIG. 7f, FIG. 26a). Other significant gene sets associated with human adhesion fibroblasts include 'Extracellular Matrix Structural Constituent' and 'Collagen Trimer' (FIG. 26a). Furthermore, GO terms revealed enrichment of extracellular structure and matrix organization, several chromosomal processes, as well as collagen metabolism and fibril organization (FIG. 26b).

Figure 27:
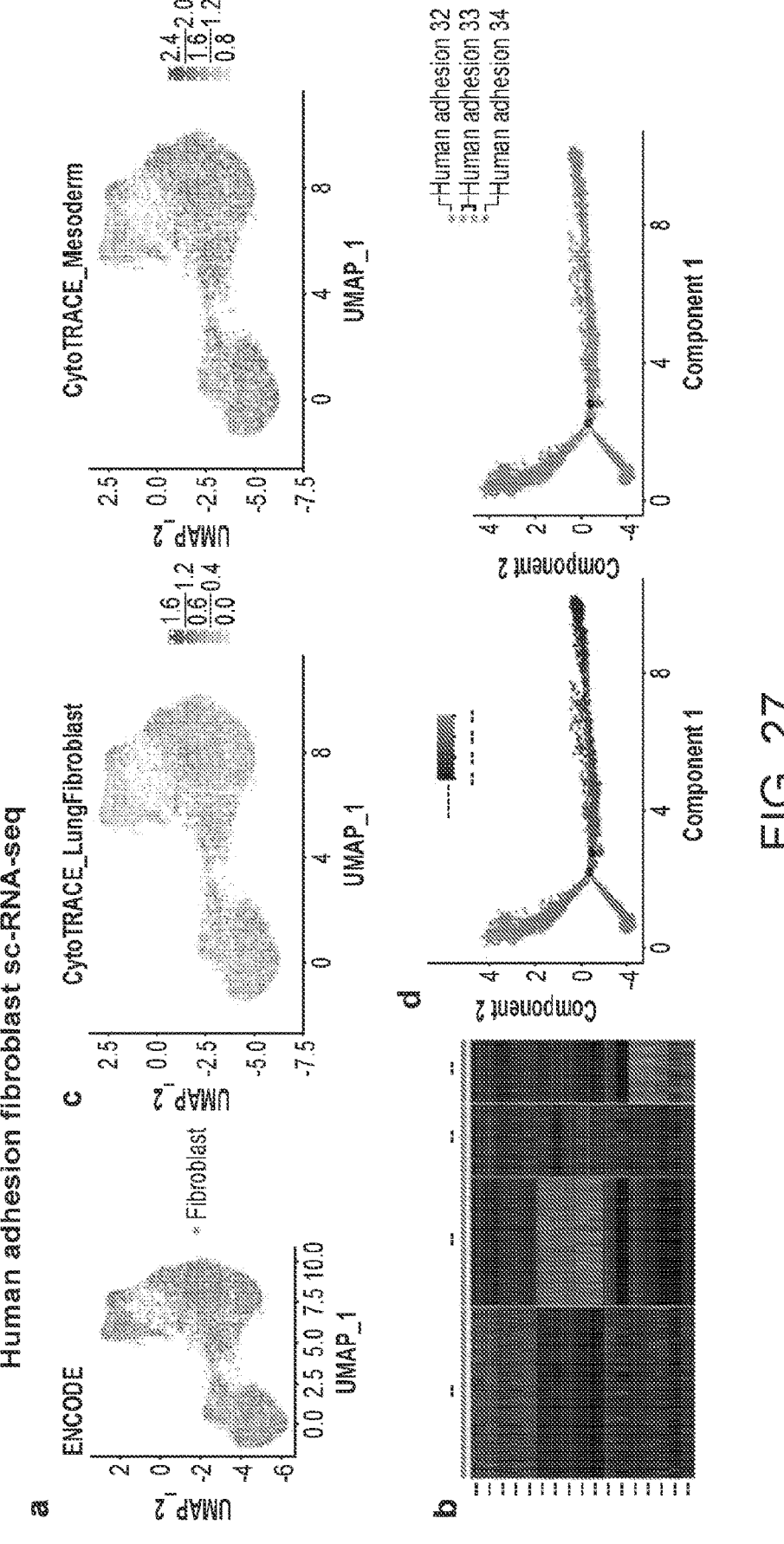
FIG. 27. Human adhesion fibroblast sc-RNA-seq a, ENCODE objective analysis to identify cell types (fibroblasts) represented in human adhesion fibroblast sc-RNA-seq data (FIG. 8*a*). Cell types as labelled by colors. b, Heatmap showing differential gene expression patterns based on clusters (FIG. 8*a*). Colors and numbers represent clusters along top of panel, most differentially expressed genes labelled at left. c, CytoTRACE analysis of human scRNA-seq data using lung fibroblasts (left panel) and mesoderm (right panel) datasets for reference. d, Pseudotime plots for human scRNA-seq data—pseudotime (left panel) and clusters (from FIG. 8*a*, right panel).

Human abdominal adhesion fibroblasts display heterogeneity and JUN dependence To explore heterogeneity among human adhesion fibroblasts at the transcriptional level, we isolated fibroblasts from three surgical patients and conducted sc-RNA-seq using the 10× Genomics platform. Cells from individual patient specimens were labelled with hash-tag oligos in order to explore any differences that might be seen between fibroblasts isolated from adhesions from different patients. The sequencing data show 4 distinct clusters of human adhesion fibroblasts based on gene expression (FIG. 8a, FIG. 27a), with considerable heterogeneity noted among all fibroblasts (FIG. 27b). This heterogeneity is not attributable to differences between individual patient specimens (FIG. 8b); in fact, cells from the 3 patient specimens analyzed are represented relatively evenly across the four clusters, suggesting that there is a common/shared adhesions gene expression phenotype across different patients (irrespective of differences in gender or reason for surgery, for example).

We also conducted CytoTRACE analysis on the human adhesion fibroblast sc-RNA-seq data, as with our mouse dataset above. Unlike in our murine RNA-seq analysis, a clear pattern of differentiation was not identified in these human fibroblasts, suggesting that the cells we evaluated from human adhesion specimens existed in an established, profibrotic steady state. This is supported by the diverse phenotypic nature of these samples, which were collected from independent patients many months after abdominal surgery (range: 9-19 months post-operative). The difference in time after surgery between patients did not appear to be a driver of transcriptional clustering, further supporting the concept of a common, chronic fibrosis state (FIG. 27c). We also applied pseudotime analysis to compare the properties of the identified fibroblasts subpopulations (FIG. 27d—left panel). Two branch points were identified (FIG. 8c), with representation of all specimens in all transcriptionally-defined clusters (FIG. 27d—right panel), again suggesting that the differences in time after surgery between patients (range 9-19 months after initial surgery) was not a significant driver of subsequent meta-state distribution.

These data support the conclusion that adhesion fibroblasts maintain a chronic, fibrosis state indefinitely following activation. This is in line with the clinical observation that abdominal adhesions persist indefinitely in patients. Next we explored the expression of specific genes in relation to the clustering of our human adhesion fibroblast sc-RNA-seq data. JUN and STAT3 are expressed throughout all clusters and by all patients. FSP1 is strongly expressed by nearly all cells assessed, while ASMA expression is found throughout but highest in clusters 1 and 2, and PDGFRA expression is highest in clusters 0 and 3 (Supplemental FIG. 20a). GO enrichment analysis of these human adhesion fibroblast scRNA-seq clusters revealed less enrichment of components involved in acute phase processes compared with our mouse data, and instead demonstrated comparative enrichment of oxidative phosphorylation and ATP metabolism. Such processes suggest that maintenance of the adhesion fibroblast profibrotic state may be associated with alterations in local metabolic programming.

Figure 28:
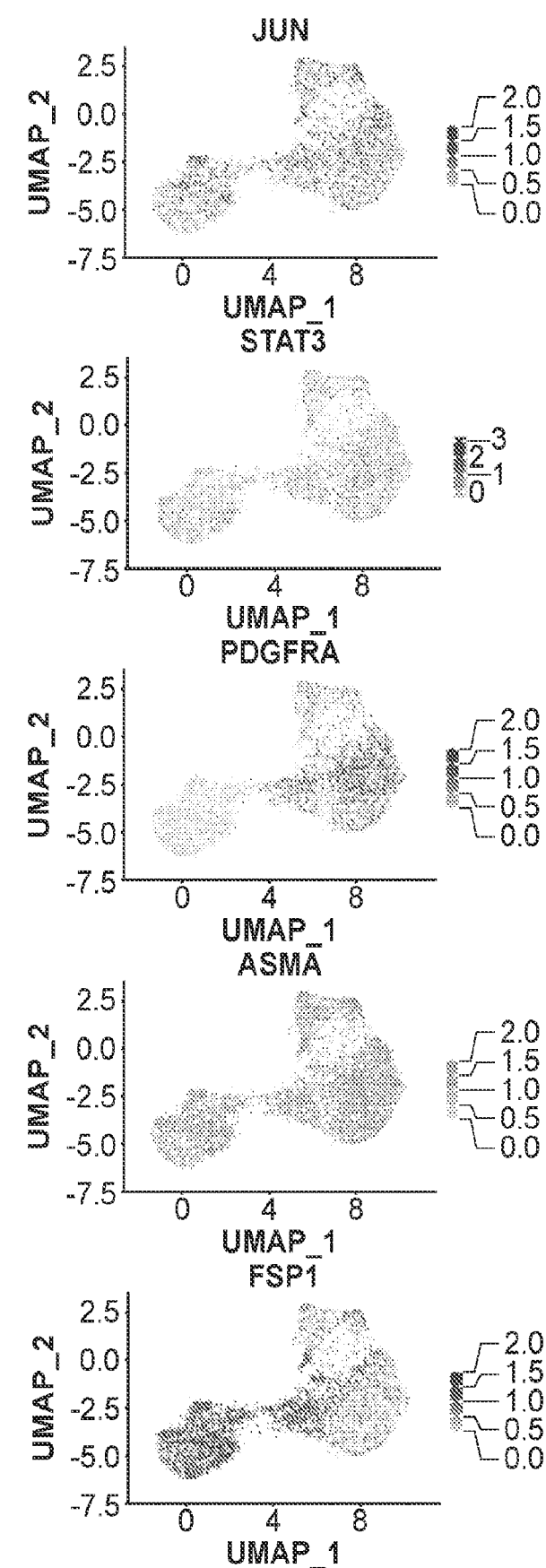
FIG. 28. Human adhesion fibroblast sc-RNA-seq feature plots and GO analysis. a, Human scRNA-seq data UMAP feature plots for the following genes, from top to bottom: JUN, ASMA, STAT3, PDGFRA, and FSP1. b, GO term analysis for human sc-RNA-seq dataset. Terms and statistics as noted in figure panels. Colors used to highlight specific processes and components correlate with cluster colors used in FIG. 8*a*.

Focal adhesion and cell substrate junction processes are also differentially enriched among all clusters, suggesting that the altered tissue mechanics found in fibrosis such as adhesions likely play a persistent role in meta-state regulation. Extracellular matrix and components are also strongly enriched throughout all clusters consistent with the fibrotic phenotype observed. Wnt pathway signaling is also enriched particularly in cluster 1 (FIG. 28b); JUN is a known transcription factor partner in non-canonical Wnt pathway signaling. Taken together these data support JUN as a primary mediator of fibrosis—which occurs through several downstream pathways—in abdominal adhesions in humans.

Figure 8:
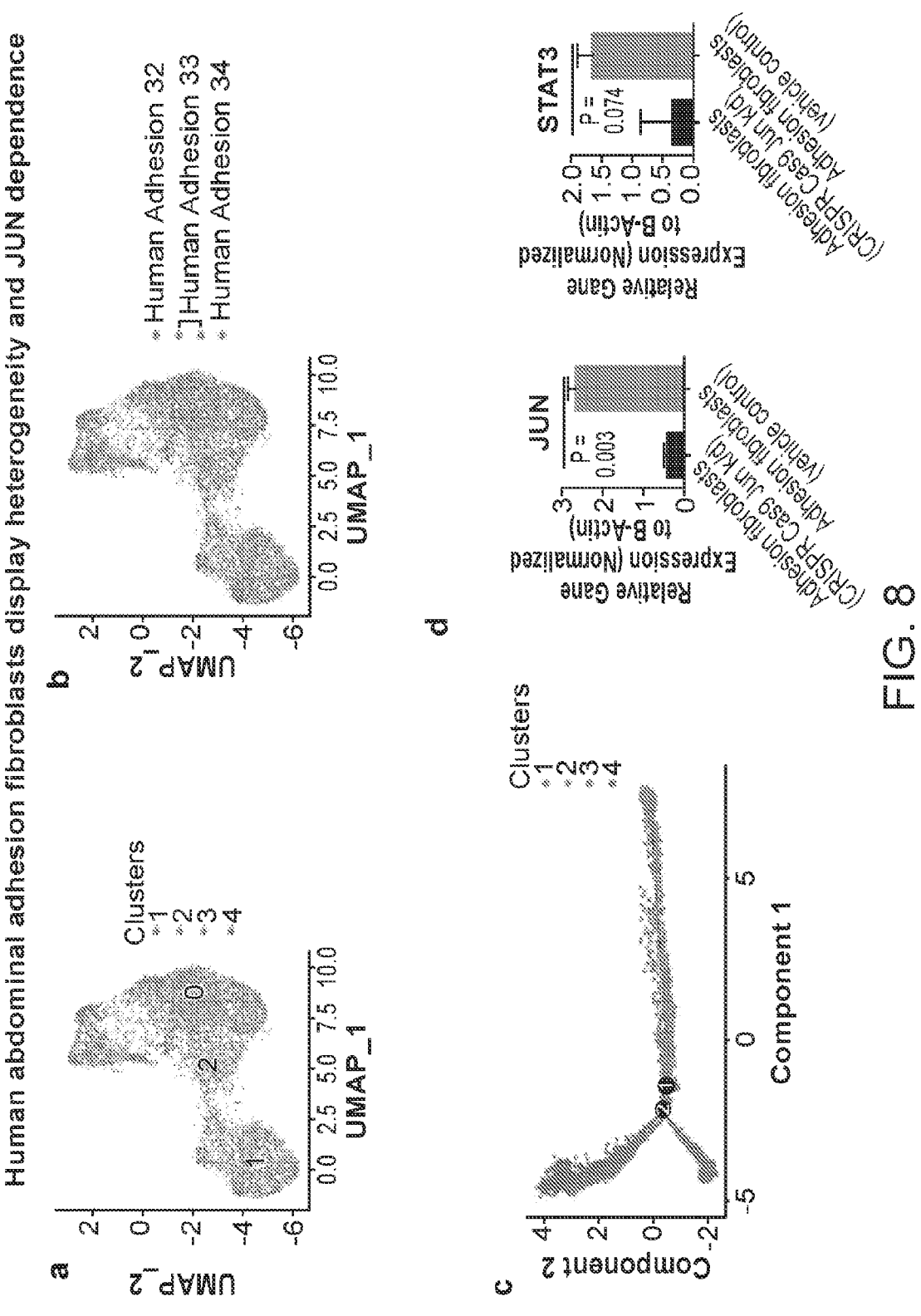
FIG. 8. Human abdominal adhesion fibroblasts display heterogeneity and JUN dependence a, Uniform manifold approximation and projection (UMAP) plots showing single cell (sc)RNA-seq data from human adhesion fibroblasts FACS-isolated using an unbiased, lineage-negative sort strategy from three unique human specimens. Four unique clusters are identified. b, UMAP plot showing representation of individual patient samples across the cluster presented in 1. Human hash-tag labels indicated at right, 2 hash-tag antibodies were used for patient 33 as an internal control, as noted in the figure panel legend. c, Pseudotime analysis of human abdominal adhesion fibroblast scRNA-seq data. Colors match cluster colors assigned in panel a. d, Quantitation of qPCR analysis for JUN, STAT5, STAT3, and SPP1 of vehicle control versus JUN CRISPR Cas9 knock-down human abdominal adhesions fibroblasts. P values noted in figure. n=6. e, Quantitation of Ki67 expression using ICC of primary human abdominal adhesions fibroblasts treated with CRISPR Cas9 JUN knockdown compared with vehicle control. f, Quantitation of Collagen Type I expression using ICC of primary human abdominal adhesions fibroblasts treated with virally-mediated JUN overexpression, vehicle control, or CRISPR Cas9 JUN knockdown. g, Schematic (based on published KEGG pathways) displays proposed JUN-relevant signaling pathways identified in this study. The left panel shows the acute phase response following tissue injury by which JUN is initially activated. The right panel shows the chronic profibrotic state that is established in adhesion fibroblasts. Blue circle highlights AP-1, red indicates the role of JUN inhibitor. Colors as labelled in the figure. ECM=extracellular matrix. Data and error bars represent means±SD. HPF=high power field. A.U.=arbitrary units. *P=0.04, P=0.03, *P=0.03, unpaired two-tailed t test.
Figure 29:
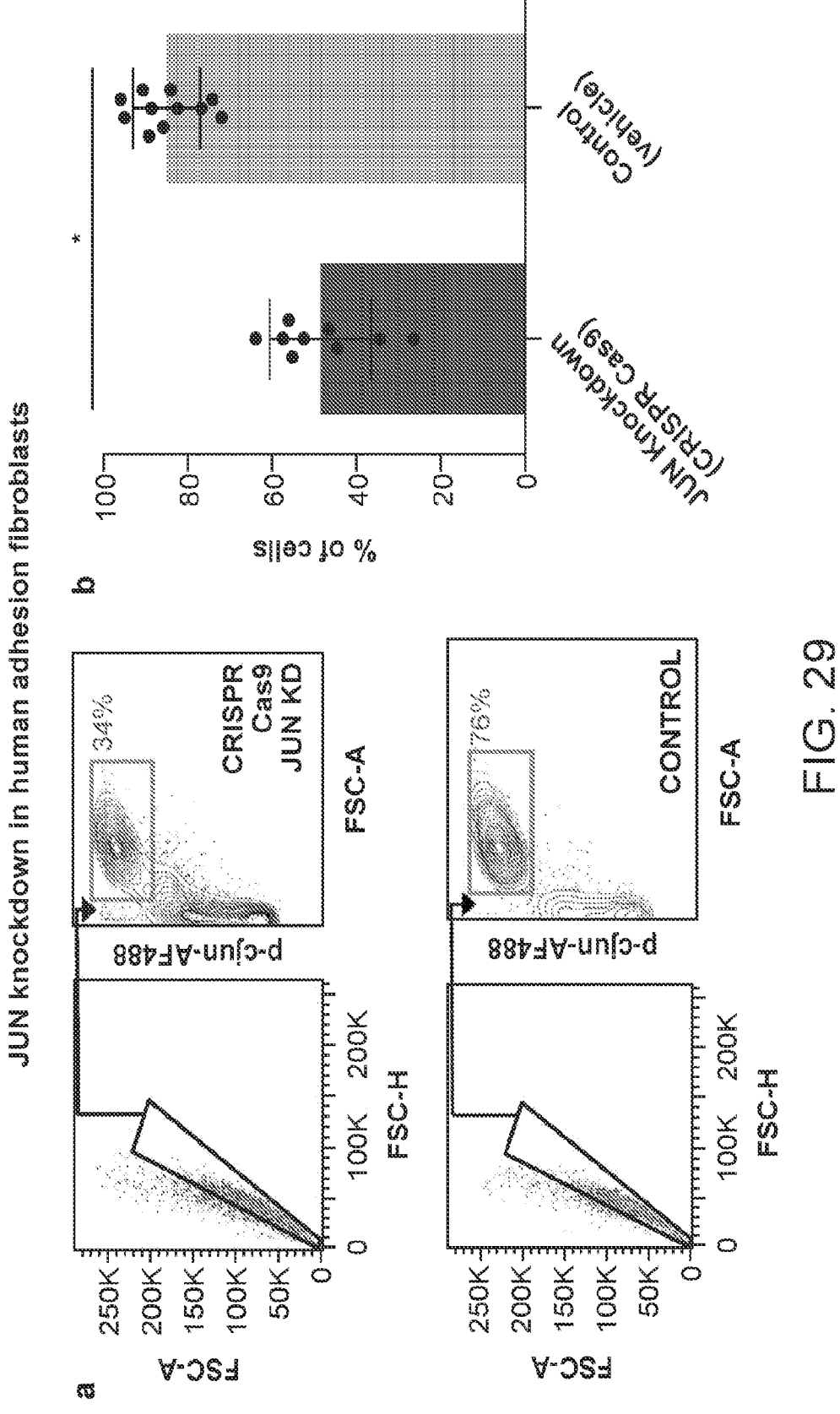
FIG. 29. JUN knockdown in human adhesion fibroblasts. a, Representative phospho-flow cytometry analysis of human abdominal adhesion cells shows knock down of phospho-JUN expression with CRISPR Cas9 (top panels) compared with vehicle control abdominal adhesion cells (bottom panels). Conditions as noted in figure, percentages of cells noted in corresponding color next to gates. b, Quantitation of phospho-flow cytometry analysis of phospho-JUN expression in human adhesion fibroblast samples treated with CRISPR Cas9 to knock-down JUN or vehicle control. n=12. Data and error bars represent means±SD. *P=0.0001, unpaired two-tailed t test.
Figure 30:
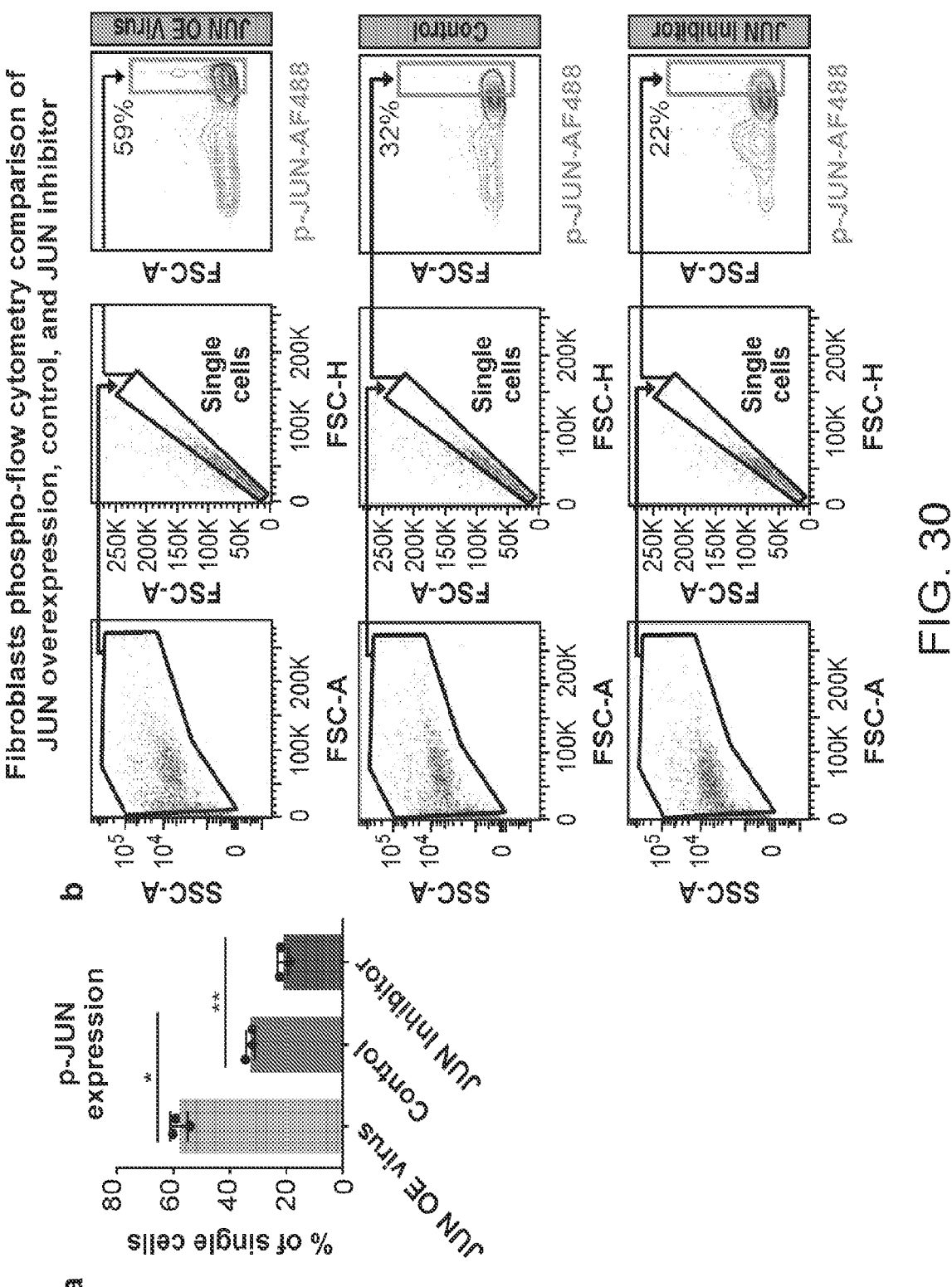
FIG. 30. Fibroblast phospho-flow cytometry comparison JUN overexpression, control, and JUN inhibitor a, Quantitation of phospho-flow cytometry analysis showing % p-JUN+ of total single cells of NIH 3T3 cells treated with the following conditions: virally-mediated JUN overexpression, vehicle control, and JUN inhibitor. n=3. b, Representative phospho-flow cytometry plots for data quantitated in a. Conditions as labelled in figure panel. Data and error bars represent means±SD. *P=0.0002, **P=0.001, unpaired two-tailed t test.

To functionally validate the role of JUN in human adhesion formation, CRISPR Cas9 was used to knock-down JUN expression in freshly-isolated human abdominal adhesion fibroblasts. Knockdown was confirmed at the protein level (FIG. 29a-b). qPCR assay of JUN knockdown fibroblasts showed a decrease is expression of profibrotic genes including JUN, STAT3, STAT5, and SPP1 (FIG. 8d). At the protein level, we found that CRISPR Cas9 JUN knockdown results in a significant decrease in human adhesion fibroblast proliferation (assessed via Ki67 immunofluorescence) compared with control—freshly isolated adhesion fibroblasts (FIG. 8e). To further validate these results, we applied virally-mediated JUN overexpression to primary human adhesion fibroblasts. This causes significant upregulation of p-JUN expression compared with control or JUN inhibitor (validated in a fibroblast cell line, FIG. 30a-b). Compared alongside vehicle control primary human adhesion fibroblasts and those treated with CRISPR Cas9 JUN knockdown, collagen expression at the protein level was significantly elevated with JUN overexpression in primary human abdominal adhesions fibroblasts compared with control or CRISPR Cas9 JUN knock-down (FIG. 8f). These human data are consistent with our mouse data, supporting that JUN is a key initiating factor for adhesion formation in human tissue.

Taken together, these data support JUN as a transcriptional master regulator of fibroblasts. Mechanical injury in the form of abdominal surgery or intra-abdominal infection insights a local wound healing response that involves platelet aggregation at the site and associated PDGF and IL6 release. These factors initially precipitate JUN expression (FIG. 8g—left panel). Once induced, JUN signaling auto-amplifies, acting as a profibrotic transcription factor via several downstream signaling responses including JAK-STAT and EMT pathways. These fibroblasts take over production of IL6 and related factors resulting in a chronic, high-JUN, profibrotic state through which adhesions are maintained indefinitely (FIG. 8g—right panel). Suppression of JUN pathway signaling is sufficient to block this process and dramatically decrease adhesion formation.

In summary, abdominal adhesions constitute a major medical problem for millions of patients for which effective therapeutic options are needed. In this study, we systemically explored abdominal adhesion biology in vivo in parallel in mice and humans at the tissue, transcriptomic, and protein level. We found that JUN expression is an early promotor of abdominal adhesions, which upregulates signaling of several pathways known to result in fibrosis including JAK/STAT, EMT, as well as PDGFRA expression. In both mice and human tissue, we elucidated the identity of adhesion fibroblasts, which can be isolated based on expression of JUN, PDGFRA, ASMA, and FSP1. Adhesions are formed by local fibroblasts and proliferate clonally following injury, suggesting that this clinical phenomenon involves progenitor-type cell activation. We developed a novel model for abdominal wall transplantation and show that the adhesion fibroblast population derives primarily from the visceral peritoneum, confirming our observation in clinical surgery that adhesions are most prominent after open abdominal surgery with manipulation of the bowel (rather than laparoscopy in which frequently only the parietal peritoneum is affected).

In both mouse and human RNA-seq data, epithelial-mesenchymal transition (EMT) and JUN pathway signaling are significantly upregulated at the transcriptional level. On single-cell RNAseq, adhesion fibroblasts from both mice and humans are heterogeneous, with three transcriptionally distinct fibroblast clusters in the mouse data and four in humans. On pseudotime analysis, validated at the protein level, JUN is expressed early in mouse tissues and maintained over time. In human adhesion fibroblasts harvested many months after surgery, JUN expression is ubiquitous and maintained indefinitely. Functionally, AP-1 (JUN) inhibition significantly suppressed adhesion formation in vivo in mice, and profibrotic gene and protein expression, as well as proliferation, in human adhesion fibroblasts in vitro. As such, treatment with the inhibitor shows potential toward clinically minimizing adhesion formation.

Methods

Animals. The following mouse strains were purchased from Jackson Laboratories: Black/6 (C57BL/6J), ROSA26mTmG (B6.129(Cg)-Gt(ROSA)26Sortm4(ACTB-tdTomato,-EGFP)Luo/J),37 PDGFRaGFP (B6.129S4-Pdgfratmi 1 EGFPSor/J), PDGFR α CreERT2 (B6N. Cg-Tg(Pdgfracre/ERT)467 Dbe/J), eGFP (C57BL/6J-Tg(CAG-EGFP)10sb/J), EN1Cre (Eni-tm2(cre)Wrst/J), Wt1CreERT2 (Wt1-tm2(cre/ERT2)Wtp/J), and ACTINCreERT2 mice (Tg (CAG-cre/Esr1)5Amc/J). Rainbow mice (ROSA26VT2/GK3) were provided as a gift from the Weissman Laboratory, Stanford University School of Medicine. JUN mice (flp-in tetO-c-JUN) were provided by the Wernig Laboratory, Stanford University School of Medicine. Mice were housed at the Stanford University Comparative Medicine Pavilion (CMP) and Research Animal Facility (RAF). The facilities provided light- & temperature-regulated housing for all animals. Mice were given rodent chow and water ad libitum. A minimum sample size of three animals was used for all experiments (exact numbers for experiments are provided in the figure legends). 10-week-old mice with appropriate genotypes for a given experiment were randomly allocated to the various experimental conditions. Healthy litter mates were used as controls. All experiments were carried out in accordance with the Stanford University Animal Care and Use Committee standards of care.

Mouse Model for Adhesions. A similar model for abdominal adhesion formation has been described previously by our laboratory. In brief, mice were anesthetized with inhaled isoflurane (Henry Schein Animal Health,) at a concentration of 1-2% in oxygen at 3 L/min. Ophthalmic ointment (Puralube petrolatum, Dechra Veterinary Products) was applied to the cornea to prevent desiccation. Buprenorphine (Buprenex, Reckitt Benckiser Pharmaceuticals Inc.) was administered subcutaneously prior to the surgery at a dose of 0.1 mg/kg. The mice were placed in the supine position on a clean operating surface. A heating pad was used beneath the surgical field to keep the animals warm throughout the procedure. The abdomens were shaved, and the skin of the abdomen was sterilized with three applications of betadine followed by 70% ethanol. During the procedure, the respiratory rate of the animals was monitored, and the isoflurane was titrated accordingly. A vertical midline skin incision was made in the abdomen with sharp scissors. The underlying abdominal wall was then opened vertically. The cecum was located and exteriorized. The cecal wall was abraded gently with 150-grit sandpaper. The parietal peritoneum along the abdominal wall was similarly abraded with sandpaper and three, single, interrupted, 4-0, silk sutures were placed into the right abdominal sidewall, which served as a nidus for adhesion formation. The cecum was then placed anatomically adjacent to the right abdominal wall. The abdomen was briefly irrigated with warmed, sterile, normal saline. The irrigant was removed by blotting with a gauze sponge. The abdominal wall incision was closed with running 6-0 Monocryl suture, and the skin incision was closed with 6-0 nylon, horizontal mattress sutures. The animals were monitored during recovery from anesthesia. Additional buprenorphine was given every 6-12 hours as needed for pain. For sham surgery, animals were treated in an identical manner; however, incisions were closed without manipulation of abdominal organs.

Liposomal Tamoxifen Induction. Activated 4-hydroxytamoxifen liposomes (LiTMX) were prepared as described by Ransom et al., 2018. LiTMX were applied locally to the visceral and parietal peritoneum at the site of interest for induction of Cre Recombinase at the time of adhesion surgery. The adhesion procedure was conducted otherwise as described above.

Abdominal Wall Transplant. A 1×1 cm section of abdominal wall (full thickness muscular layer and parietal peritoneum) was harvested from PDGFRA$^{GFP}$::RosamTmG mice under surgical conditions. The same size section of abdominal wall was excised from PDGFRA$^{GFP}$ mice. The PDGFRA$^{GFP}$::RosamTmG transplants were rapidly transplanted and sutured into place in the PDGFRA$^{GFP}$ mice using 4-0 silk interrupted sutures. Adhesions were created as previously described and harvested at post-operative day (POD).

In Vivo JUN Induction and Suppression. Doxycycline (2 mg/mL) or T-5224 (Cayman Chem, 10 uM) resuspended in DMSO were applied locally to adhesion sites at the time of adhesion surgery for JUN induction (in JUN mice) or suppression (in JUN and WT mice), respectively. Vehicle only was used for control.

Parabiosis Model. Parabiotic mouse pairs were created as previously published. Briefly, both age- and sex-matched wild-type (WT, C57BL/6;) and eGFP-labeled mice (C57BL/6-Tg(CAGEGFP)10sb/J) were housed together for two weeks prior to parabiosis surgery. Mice were anesthetized; the sides of the mice were shaved and cleaned with betadyne and 70% ethanol as previously described. An incision was made from base of the right foreleg to the base of the right hind leg on WT mice and an identical incision was made on the left leg of the eGFP mice. The skin was sutured together. Peripheral blood chimerism was determined two weeks later via flow cytometry. Adhesion surgeries were then performed on the WT mice.

Tissue Processing and Histology. Mouse and human adhesion and control tissues were fixed in 4% paraformaldehyde (Electron Microscopy Sciences) for 20 hours at 4° C. and embedded into paraffin per standard protocols. For cryopreservation, specimens were placed in 30% sucrose (Sigma) until saturation at 4° C. following fixation, followed by OCT until saturation at 4° C., and then embedded in OCT. Representative tissue specimens were stained with hematoxylin and eosin (H&E, Sigma-Aldrich), Picrosirius Red Stain (Abcam), or Masson's trichrome (Sigma-Aldrich) per manufacturer's protocols.

Gross and Histologic Scoring of Adhesion Tissue. Both gross and histologic scoring systems were used to evaluate extent of adhesion formation in mice. Scoring of adhesion tissue from gross images was achieved using the adhesion scoring system previously described by Tsai et al. The histologic scoring system used was adapted from Tsai et al. and Linksy et al. and applied to H&E-stained specimens. In brief, a histologic adhesion score of 0 was assigned to histological specimens with no apparent adhesion between peritoneal surfaces. A score of 1 indicated 'stringlike' adhesions or <10% of contact with adherent tissue. A score of 2 indicated non-continuous adhesions, thicker than strings with <25% contact with adherent tissue. A score of 3 indicated non-continuous but dense adhesion with <50% contact with adherent tissue. A score of 4 included specimens with continuous adhesion with multiple (<75%) points of contact with adherent tissue. A score of 5 was characterized by dense (100%), continuous contact with adherent tissue.

Cell Culture. Fibroblasts was resuspended in media (DMEM supplemented with 10% FBS) and seeded into a plate (Falcon) coated with EmbryoMaxA ultrapure water with 0.1% gelatin (Millipore). All cells were maintained under sterile conditions in a humidified incubator under 5% $CO_2$ at 37° C. A phase-contrast microscope (Leica) was used to image cells.

Immunocytochemistry (ICC). Coverslips were coated with 1% Embryomax gelatin (EMD Millipore). Adhesion and control fibroblasts were seeded onto the coverslips. Once stuck, the cells were fixed, permeabilized with 0.5% Triton-X-100 (Sigma), and then incubated with 1× Powerblock (Biogenex). The cells were then stained with primary antibody at 4° C. overnight. The following day, the cells were washed with 0.1% Tween-20 (PBST; Sigma Aldrich), then stained with secondary antibody, and incubated at room temperature for 1 hour. The slides were then mounted using Prolong Gold Antifade Mountant with DAPI (Life Technologies).

Immunofluorescence (IF). Cryopreserved specimens were cryosectioned onto Superfrost Plus microscope slides (FisherSci). The sections were permeabilized with 0.5% Triton-X-100, and then incubated with 1× Powerblock (Biogenex). Primary antibodies were applied to tissue specimens for 1 hour at room temperature, and then rinsed repeatedly. Secondary antibodies were applied for one hour at room temperature. The antibody incubation and washing steps were repeated if multiple proteins were stained for in one specimen section. Slides were then mounted using Prolong Gold Antifade Mountant with DAPI. Antibodies used for IF included: Anti-phospho-JUN (Cell Signaling, S63 (54B3), lot: 7), anti-JUN (Abcam, ab31419, lot: GR306615-18), anti-aSMA (Abcam, ab32575, lot: GR282976-32), anti-FSP-1/S100A4 (Abcam, ab41532 lot: GR3176834-1), anti-COL3 (Abcam, ab7778, lot: GR3234897-1), anti-COL1 (Abcam, ab34710, lot: GR3244041-2), anti-MSLN (ABBiotec, 250519, lot: 15102712), anti-CD26 (Abcam, ab28340, lot: GR311941-9), anti-vimentin (Abcam, ab11256, lot: GR236597-5), anti-phospho-FAK (Thermo Fisher, 799255, lot: RG240925A), anti-PDPN (Invitrogen, MA5-29742, lot: UB2724771), anti-CD10 (Abcam, ab227640, lot: GR3227478-1), anti-CD31 (Abcam, ab28364, lot: GR3247742-7), anti-CD45 (Abcam, ab10558, lot: GR269008-1), anti-phospho-Stat5 (Cell Signaling, 9314S), anti-PDGFRa (Abcam, ab203491, lot: GR3226597-1), IgG Alexa-Fluor 488 (Invitrogen, A32731, lot: SH251139), IgG Alexa Fluor 555 (Invitrogen, A32732, lot: SH251140), IgG Alexa Fluor 647 (Invitrogen, A32733, lot: Sl231745).

Confocal Imaging and Analysis. Laser scanning confocal microscopy was performed using a Leica WLL TCS SP8 Confocal Laser Scanning Microscope (Leica Microsystems) located in the Cell Sciences Imaging Facility (Stanford University, Stanford, CA). The 10×, 20× and 40× objectives were used (10× HC PL APO, air, N.A. 0.40; 20× and 40× HC PL APO IMM CORR CS2, H2O/Glycerol/oil, N.A. 0.75). Raw image stacks were imported into Fiji (Image-J, NIH) or Imaris (Bitplane) software for analysis. Fiji was used to make two-dimensional micrographs of the confocal data and to quantify fluorophore expression intensity. For analysis of clonality from Rainbow mouse tissue, surfaces were created for each color of the Rainbow construct expressed using the volume surface and thresholding tools in Imaris.

Recruitment of Human Specimens. Human abdominal adhesion and control specimens were obtained at the Stanford Hospital under Stanford University's IRB approval. Clinical inclusion criteria were as follows: For adhesion specimens—patients must have had at least one prior abdominal surgery, for control specimens—patients must have had no history of prior abdominal surgery. For all patients, surgery must be elective, and there must be no evidence of active inflammation/infection at time of operation. Written, informed consent was obtained from the patient in the pre-op holding area prior to surgery. Tissue was collected in the operating room, placed directly into sterile saline, and kept on ice for transport. Sample preparation and FACS isolation. Adhesion or control tissue from mouse or human specimens was minced on ice. The tissue was then digested for 60 minutes in a 37° C. water bath agitator in 2 mg/mL collagenase (collagenase type IV, ThermoFisher) digest buffer in Medium 199 (HyClone, GE Healthcare) consisting of 5% fetal bovine serum (Gibco FBS, ThermoFisher), DNase I (Worthington), Poloxamer 188 (Cat. P5556-100ML, Sigma), HEPES, and CaCl2. The digest was quenched with quench media (DMEM (Gibco DMEM, ThermoFisher) with 15% FBS), then centrifuged at 300×G for 5 minutes at 4° C., resuspended in quench media, and filtered through 100, 70, and 40 μm cell strainers (Falcon cell strainer, ThermoFisher). Red blood cell lysis was performed using Hybri-Max (Sigma) per the manufacturers protocol. Histopaque was performed using Histopaque-1119 (Sigma Aldrich), per the manufacturers protocol. Cells were counted and re-suspended in FACS buffer. Primary antibodies were applied, and cells were stained in the dark with gentle agitation for 30 minutes. Cells were then washed thoroughly in FACS buffer. Staining with secondary antibodies was conducted in the same manner. Propidium iodine (PI, Thermofisher, Cat. P3566, lot: 1755970, 3 μg/mL) or DAPI (Thermofisher, Cat. 3571) were used as a viability marker. Fibroblasts were isolated using the FACS Aria II system. For RNA sequencing, cells were sorted into chilled lysing reagent under RNA/DNAsefree conditions (Trizol LS, ThermoFisher). Flow-cytometry plots shown are representative of at least three independent experiments. Antibodies against the following cell surface markers primarily or secondarily conjugated to the same fluorophore were used for exclusion of "lineage" cells in mouse and human specimens in order to isolate fibroblasts in an unbiased manner: CD45, CD31, Ter119, Tie2, CD324, and CD326. This approach has been previously validated by our laboratory in other fibrotic pathologies. For phospho-specific flow cytometry analysis, a single cell suspension was prepared using manual tissue dispersion rather than enzymatic digestion to preserve phosphorylated signal, and then prepared using the BD Biosciences Cytofix/Cytoperm™ kit according to manufacturer's instructions. Phosphorylated protein analysis was conducted using the FACS Aria II system. Antibodies used for FACS included: Anti-phospho-JUN (Cell Signaling, s73d47G9, lot: 5), antiphospho-STAT5-PECy7 (BD Biosciences, 560117, lot: 8266820), anti-FSP-1 (Ray biotech, 188-11191, lot: 1804128), IgG Pacific Blue (Thermo Fisher, p31582, lot: 1929717), anti-PDGFRa (Abcam, ab90967, lot: gr321324-2), IgG Alexa-Fluor 647 (Abcam, ab150159, lot: GR241187-2), IgG Alexa-Fluor 488 (Abcam, ab150077, lot: GR3224145-2), IgG Alexa Fluor 647 (Abcam, ab: 150075, lot: GR269275-2), IgG Pacific Blue (Thermo Fisher, P10994, lot: 2045342), anti-S100A4-PE (BioLegend, 370003; lot b286200), anti-PDGFRa (Abcam, ab203491, lot: GR3226597-1), anti-CD45-FITC (Invitrogen, 11-9459-42, lot 4319940), anti-Ter119-FITC (Invitrogen, 11-5921-85, lot: 4322597), anti-CD31-FITC (Thermo Fisher, 303104, lot: B224877), anti-Tie2 (Thermo Fisher, 14-5987-82, lot: 2072830), anti-CD324 (Biolegend, 147302, lot: B228369), anti-CD326 (Biolegend, 118202, lot: B254013), 488 secondary (Abcam, ab150157), anti-CD45-Pacific Blue (Invitrogen, 48-0451-82 lot: 1936503), anti-Ter119-Pacific Blue (Invitrogen, 48-5921-82 lot: 1974934), anti-CD31-Pacific Blue (Invitrogen, 48-0311-82 lot: 1982691), anti-Tie2-biotin (Invitrogen, 13-5978-82, lot: 4304957), anti-CD324-biotin (Invitrogen, 13-3249-82 lot:1916204), eFluor450-Streptavidin (Invitrogen, 48-4317-82, lot 1988686), anti-CD326-Pacific Blue (Invitrogen, 48-5791-82 lot: 1984115), anti-CD45-PECy7 (Thermo Fisher, MHCD4512), anti-Ter119-PECy7 (Invitrogen, 25-5921-82, lot: 1994153), anti-CD31-PECy7 (Invitrogen, 25-0311-81, lot 4318668), anti-Tie2 (Invitrogen, 14-5987-82, lot: 2072830), anti-CD326-PECy7, (BioLegend, 324221 lot: B266928), and anti-CD324-PECy7 (Biolegend, 147310; lot: B255274).

FACS gating and data analysis was performed using FlowJo. Gating schemes were established with fluorescence-minus-one controls. Single cells were first gated using FSC and SSC parameters. Dead and lineage-positive (non-fibroblast) cells were then excluded by gating against PI or DAPI, and lineage panel antibody staining, respectively. Gating schemes to quantitate and/or isolate fibroblasts and specific fibroblast sub-populations of interest were validated by plating a portion of the sorted cells for morphological visualization, immunocytochemistry and/or qPCR assay.

Bulk mRNA Sequencing. For mouse and human specimens, RNA extraction was performed using Qiagen miRNeasy kit (cat. 1071023) with on column DNase treatment per the manufacturer's recommendations. The Clontech Smarter Ultra Low Input RNA kit (Takara Bio, Cat. 634848) was used to generate cDNA from 150 pg total RNA following the manufacturer's recommendations. Amplified cDNA was purified using SPRI Ampure Beads (Beckman Coulter, Cat. A63880) and the quality and quantity were measured using a High Sensitivity DNA chip on the Agilent 2100 Bioanalyzer (Agilent Technologies). cDNA was sheared to an average length of 300 basepairs using a Covaris S2 ultrasonicator (Covaris) and libraries were generated with the Clontech Low Input Library Prep kit (Takara Bio, Cat. 634947). The samples were uniquely barcoded, pooled, and sequenced on a single lane of the NextSeq 500 (Illumina). A total of 300 million paired-end, 151 base pair reads were obtained, resulting in 50 million reads per sample. Bulk mRNA Sequencing Data Analysis. A total of 9 human (6 adhesions and 3 controls) and 8 mouse (4 adhesions and 4 sham-surgery controls) samples were profiled by bulk RNAsequencing as described above. Raw FASTQ reads were aligned to GENCODE v29 reference transcripts (GRCh38.p12) for human and GENCODE vM20 reference transcripts (GRCm38.p6) for mouse with Salmon 40 v0.12.0 using the --seqBias, --gcBias, --posBias, --useVBOpt, --rangeFactorizationBins 4, and --validateMappings flags and otherwise default parameters for single-end mapping. Salmon results were merged into a single gene-level counts matrix using the R package, tximport 41 v1.4.0. Count normalization and differential gene expression analysis was performed using the DESeq2 v1.22.2 package in R 42. Counts were size-factor normalized using the 'DESeq' function and log 2—transformed. Pairwise differential gene expression analysis was performed using the lfcShrink function and indicating 'type=apeglm', which applies the adaptive t prior shrinkage estimator. As recommended, a threshold of P-adjusted<0.1 was used to define significance for differentially expressed genes. Gene set enrichment analysis (GSEA) was performed on pre-ranked gene lists of differentially expressed genes (n=851 genes for mouse, n=3,003 genes for human) ordered by log 2-fold change using the GSEA software provided by the Broad Institute. The 'HALLMARK_EPITHELIAL_MESENCHYMAL_TRAN-SITION' and "GO_REGULATION_OF_JUN_KI-NASE_ACTIVITY" gene sets were used to highlight genes involved in epithelial-to-mesenchymal (EMT) and Jun signaling pathway. Hypergeometric tests to analyze enrichment of gene ontology (GO) terms in the genes differentially expressed in the "Adhesion" versus "Sham" (mouse, n=451 genes) or "Healthy" (human, n=1,443 genes) groups were performed using the clusterProfiler v3.10.0 44 package in R.

Single cell barcoding, library preparation, and sequencing. Adhesion fibroblasts were FACS isolated from mouse and human specimens using an unbiased, lineage-based strategy as previously described. Four mouse specimens derived from litter mates were used pooled for each timepoint (POD 2 and POD 7). Individual human specimens were tagged with hashtag oligos (HTOs) per the manufacturer's protocol and then pooled. Cells were counted and filtered just prior to loading into the 10× machine. Single cells were barcoded using the 10× Chromium Single Cell platform, and cDNA libraries were prepared according to the manufacturer's protocol (Single Cell 3' v3, 10× Genomics, USA). In brief, cell suspensions, reverse transcription master mix and partitioning oil were loaded on a single cell chip, then run on the Chromium Controller. Reverse Transcription was performed within the droplets at 53° C. for 45 min. cDNA was amplified for a 12 cycles total on a BioRad C1000 Touch thermocycler. cDNA size selection was performed using SpriSelect beads (Beckman Coulter, USA) and a ratio of SpriSelect reagent volume to sample volume of 0.6. cDNA was analyzed on an Agilent Bioanalyzer High Sensitivity DNA chip for qualitative control purposes. cDNA was fragmented using the proprietary fragmentation enzyme blend for 5 min at 32° C., followed by end repair and A-tailing at 65° C. for 30 min. cDNA were double-sided size selected using SpriSelect beats. Sequencing adaptors were ligated to the cDNA at 20° C. for 15 min. cDNA was amplified using a sample-specific index oligo as primer, followed by another round of double sided size selection using SpriSelect beads. Final libraries were analyzed on an Agilent Bioanalyzer High Sensitivity DNA chip for qualitative control purposes. cDNA libraries were sequenced on a NextSeq 500 Illumina platform aiming for 50,000 reads per cell.

Data processing, fastq generation, and read mapping. Base calls were converted to reads with the software Cell Ranger (10× Genomics; version 3.1)'s implementation mkfastq. These were then aligned against either the GRCh38 v3.0.0 (for human) or mm10 v3.0.0 (for mouse) genomes using Cell Ranger' count function (an implementation of STAR v2.7.0) with SC3Pv3 chemistry and 5,000 expected cells per sample. Cell barcodes representative of quality cells were delineated from barcodes of apoptotic cells or background RNA based on a threshold of having at least 1000 transcripts profiled and less than 5% of their transcriptome of mitochondrial origin. For human samples, this resulted in 1542 unique genes detected per cell, 6,489 UMIs per cell, and 3.44% mitochondrial genes per cell. For mouse samples, we found 4183 unique genes detected per cell, 23,586 UMIs per cell, and 3.17% mitochondrial genes per cell.

Data normalization, hashtag oligo demultiplexing, and cell subpopulation identification. UMIs from each cell barcode were retained for all downstream analysis. Raw UMI counts were normalized with a scale factor of 10,000 UMIs per cell and subsequently natural log transformed with a pseudocount of 1 using the R package Seurat (version 3.1.1). Hashtag oligos (HTOs) for human samples were demultiplexed using Seurat's implementation HTODemux. Briefly, kmedoid clustering is performed on the normalized HTO values, after which a 'negative' HTO distribution is calculated. For each HTO, the cluster with the lowest average value is treated as the negative group and a negative binomial distribution is fit to this cluster. Using the 0.99 quantile of this distribution as a threshold, each cell is classified as positive or negative for each HTO. Cells that are positive for more than one HTOs are annotated as doublets and removed. Cells that are not positive for any HTO are also removed. Aggregated data was then evaluated using uniform manifold approximation and projection (UMAP) analysis over the first 15 principal components.47 Cell annotations are ascribed using SingleR (version 3.11) against the Blueprint+ENCODE reference database for human cells, and against the Immunological Genome Project (ImmGen) and mouse RNA-seq reference sets for mouse cells.

Generation of characteristic subpopulation markers and enrichment analysis. Cell-type marker lists were generated with two separate approaches. In the first approach, we employed Seurat's native FindMarkers function with a log fold change threshold of 0.25 using the ROC test to assign predictive power to each gene. However, in order to better account for the mutual information contained within highly correlated predictive genes, we also employed a characteristic direction analysis. The 50 most highly ranked genes from this analysis for each cluster were used to perform gene set enrichment analysis against the BROAD Institute databases in a programmatic fashion using EnrichR (version 2.1). Pseudotime analysis was performed using the Monocle2 package in R (version 2.4.0). Lineage differentiation analysis was performed in R using the CytoTRACE package.

Real-Time (RT) Quantitative (q)PCR. RNA was extracted from mouse and human specimens using the Direct-Zol RNA extraction kit (Zymo Research) per the manufacturer's guidelines. RNA concentrations were assessed using Nanodrop (ThermoFisher). cDNA library was created using the high capacity cDNA reverse transcription kit (Applied Biosystems) as per the manufacturer's instructions. The reverse transcription reaction was performed using a 2720 Thermal Cycler (Applied Biosystems). Power SYBR Green Master Mix (Applied Biosystems) was used for amplification using a 20 μl reaction mixture per the manufacturer's guidelines. Each experiment was carried out in triplicate for each data point, and the cycle threshold (Ct) value was used for analysis. Mean fold changes in gene expression were normalized against GAPDH for mouse specimens and beta-actin for human samples.

Human Adhesion Fibroblast Cytokine Analysis. Freshly-isolated human adhesion fibroblasts were plated in antibiotic-free media and cell supernatant was collected at 24 and 48 hours after plating, as well as cell-free media negative control. The 62-plex Luminex assay (custom-built by eBioscience) to assess cytokine content in the supernatant was conducted per the manufacturer's protocol. Three biological replicates were analyzed per timepoint. Median fluorescence intensity was used for quantification.

CRISPR-mediated genome engineering. Following the protocol from reported literature, the sequences of the site-specific guide RNAs (sgRNAs) were selected using the online CRISPR Design Tool from Feng Zhang's lab. Oligonucleotides with these sequences were cloned into the lentiCRISPRv2 vector (AddGene). The transfer plasmid (JUN CRISPR knock-out plasmid) was then cotransfected with a pRRE Packing plasmid (GAG and Pol genes), a pRSV Packing plasmid (Rev gene), and a pMD2.G enveloping plasmid into HEK293T cells. The cell media was collected, ultracentrifuged and frozen for use. In vitro T-5224 treatment. Freshly isolated mouse adhesion fibroblasts were grown to 90% confluence. Cultured cells were lifted using TrypLE (ThermoFisher Scientific) and re-plated the day of treatment in antibiotic-free media (DMEMF12 and 10% FBS). The cells were allowed to adhere, culture media was then removed and replaced with 0.1% bovine serum albumin (BSA) media for one hour. All cells were then stimulated with insulin for one hour (5 mg/ml). Wells were randomly assigned to treatment versus control conditions; treatment wells received T-5224 treatment (10 µM), control wells received vehicle only. Cells were lifted 24 hours later, and phospho-protein expression was analyzed using flow cytometry as previously described.

CRISPR Cas9 JUN-knock-down treatment. Freshly-isolated human adhesion fibroblasts were grown to 90% confluence. Cultured cells were lifted using TrypLE and re-plated the day of treatment in antibiotic-free media. The cells were allowed to adhere, culture media was then removed and replaced with 0.1% bovine serum albumin (BSA) media for one hour. Cells were then stimulated with insulin for one hour (5 mg/ml). Wells were randomly assigned to treatment, vehicle-control ("induced control") and vehicle-control-selection conditions; treatment wells received CRISPR Cas9 virus, vehicle-control received vehicle only. CRISPR Cas9 and vehicle control-selection wells received puromycin selection (1 µg/ml) dosed every 24 hours until complete cell death was seen in the vehicle-control-selection wells. Selection was further confirmed via flow cytometry. Cells from the treatment and vehicle-control wells were then lifted and processed for analysis.

Lentivirus preparation for virally-mediated JUN overexpression. 90% confluent 293T cells were transfected with 4 µg Transfer plasmid (JUN tet-on overexpression plasmid, tetracyclinecontrollable transactivator plasmid, JUN CRISPR knock-out plasmid, TK control reporter plasmid, E7TK CD47 enhancer reporter plasmid and Luciferase-GFP plasmid), 2 µg pRRE Packing plasmid (GAG and Pol genes), 1 µg pRSV Packing plasmid (Rev gene), 1 µg pMD2.G enveloping plasmid and 24 µg PEI. The cell media was collected and centrifuged, then the supernatant was filtered through a 0.22 µm strainer, ultra-centrifuged, and flash frozen for use.

Virally-mediated JUN overexpression treatment. NIH 3T3 and freshly isolated adhesion fibroblasts were grown to 90% confluence. Cultured cells were lifted using TrypLE and re-plated prior to treatment in antibiotic-free media (DMEMF12 and 10% FBS). The cells were allowed to adhere, culture media was then removed and replaced with 0.1% bovine serum albumin (BSA) media for one hour. Wells were randomly assigned to treatment versus vehicle control conditions. Aliquots of JUN overexpression virus (prepared as above) were thawed just prior to use and applied to treatment wells with polybrene (Sigma-Aldrich, 1:1000). After 6-hours incubation, the media was changed, and antibiotic-free media plus dox (2 µg/ml) was applied. Hygromycin selection was pursued at 48 hours. Selection was confirmed using flow cytometry.

Statistical analysis. Statistical analyses were performed using the software GraphPad Prism v.6 (unless otherwise noted). Results are expressed as absolute numbers, percentages, fractions, or mean+/−standard deviation (unless otherwise noted). Unpaired t-test assuming two-tailed distribution or one-way analysis of variance (ANOVA) and post hoc Tukey correction were used to compare groups where relevant. $P < 0.05$ was considered statistically significant. Data availability. Data to support the conclusions drawn in this manuscript can be found in the primary and supplemental figures. All RNA-seq data can be accessed from the Gene Expression Omnibus.

TABLE 1

Human Adhesions and Control Specimens

| Patient number | Sex | Specimen type | Months after prior surgery |
|---|---|---|---|
| 1 | F | Adhesion | 5 |
| 2 | M | Adhesion | 8 |
| 3 | F | Adhesion | 2 |
| 4 | M | Adhesion | 12 |
| 5 | F | Adhesion | 26 |
| 6 | F | Adhesion | 10 |
| 7* | M | Adhesion | 3 |
| 8 | M | Control | No prior surgery |
| 9 | M | Adhesion | 10 |
| 10* | M | Adhesion | 65 |
| 11 | M | Control | No prior surgery |
| 12* | M | Control | No prior surgery |
| 13* | F | Control | No prior surgery |
| 14 | F | Control | No prior surgery |
| 15* | F | Adhesion | 9 |
| 16* | F | Control | No prior surgery |
| 17 | F | Control | No prior surgery |
| 18 | F | Adhesion | 75 |
| 19* | M | Adhesion | 9 |
| 20 | M | Adhesion | 9 |
| 21* | F | Adhesion | 30 |
| 22 | M | Adhesion | 344 |
| 23* | M | Adhesion | 3 |
| 24 | M | Adhesion | 0 |
| 25 | M | Adhesion | 5 |
| 26 | F | Control | No prior surgery |
| 27 | M | Adhesion | 3 |
| 28 | M | Adhesion | 2 |
| 29 | M | Adhesion | 2 |
| 30 | M | Control | No prior surgery |
| 31 | M | Control | No prior surgery |
| 32* | F | Adhesion | 19 |
| 33* | M | Adhesion | 9 |
| 34* | F | Adhesion | 11 |
| | | Median | 9 months |

REFERENCES

Maciver, A. H., McCall, M. & Shapiro, A. M. J. Intra-abdominal adhesions: Cellular mechanisms and strategies for prevention. *Int J Surg* 9, 589-594, doi:10.1016/j.ijsu.2011.08.008 (2011).

Brochhausen, C. et al. Current strategies and future perspectives for intraperitoneal adhesion prevention. *J Gastrointest Surg* 16, 1256-1274, doi:10.1007/si 1605-011-1819-9 (2012).

Beyene, R. T., Kavalukas, S. L. & Barbul, A. Intra-abdominal adhesions: Anatomy, physiology, pathophysiology, and treatment. *Curr Probi Surg* 52, 271-319, doi:10.1067/j.cpsurg.2015.05.001 (2015).

Schreinemacher, M. H., ten Broek, R. P., Bakkum, E. A., van Goor, H. & Bouvy, N. D. Adhesion awareness: a national survey of surgeons. *World J Surg* 34, 2805-2812, doi:10.1007/s00268-010-0778-8 (2010).

Strik, C., Stommel, M. W., Schipper, L. J., van Goor, H. & Ten Broek, R. P. Risk factors for future repeat abdominal surgery. *Langenbecks Arch Surg* 401, 829-837, doi:10.1007/s00423-016-1414-3 (2016).

Bruggmann, D. et al. Intra-abdominal adhesions: definition, origin, significance in surgical practice, and treatment options. *Dtsch Arztebl Int* 107, 769-775, doi:10.3238/arztebl.2010.0769 (2010).

Harris, J. W. & Evers, B. M. in Sabiston Textbook of Surgery (ed C. M. Townsend) Ch. 49: Small Intestine, 1237-1295 (Elsevier, 2017).

Wernig, G. et al. Unifying mechanism for different fibrotic diseases. *Proc Natl Acad Sci USA* 114, 4757-4762, doi:10.1073/pnas.1621375114 (2017).

Marshall, C. D. et al. Creation of Abdominal Adhesions in Mice. *J Vis Exp*, doi:10.3791/54450 (2016).

Walmsley, G. G. et al. Murine Dermal Fibroblast Isolation by FACS. *J Vis Exp*, doi:10.3791/53430 (2016).

Horikawa, S. et al. PDGFRalpha plays a crucial role in connective tissue remodeling. *Sci Rep* 5, 17948, doi:10.1038/srep17948 (2015).

Saito, Y. et al. PDGFR Signaling Mediates Hyperproliferation and Fibrotic Responses of Subsynovial Connective Tissue Cells in Idiopathic Carpal Tunnel Syndrome. *Sci Rep* 7, 16192, doi:10.1038/s41598-017-16443-w (2017).

Olson, L. E. & Soriano, P. Increased PDGFRalpha activation disrupts connective tissue development and drives systemic fibrosis. *Dev Cell* 16, 303-313, doi:10.1016/j.devcel.2008.12.003 (2009).

Hamilton, T. G., Klinghoffer, R. A., Corrin, P. D. & Soriano, P. Evolutionary divergence of platelet-derived growth factor alpha receptor signaling mechanisms. *Mol Cell Biol* 23, 4013-4025 (2003).

Lawson, W. E. et al. Characterization of fibroblast-specific protein 1 in pulmonary fibrosis. *Am J Respir Crit Care Med* 171, 899-907, doi:10.1164/rccm.200311-1535OC (2005).

Louka, M. L. & Ramzy, M. M. Involvement of fibroblast-specific protein 1 (S100A4) and matrix metalloproteinase-13 (MMP-13) in CCl4-induced reversible liver fibrosis. *Gene* 579, 29-33, doi:10.1016/j.gene.2015.12.042 (2016).

Fu, C. et al. FSP1 promotes the biofunctions of adventitial fibroblast through the crosstalk among RAGE, JAK2/STAT3 and Wnt3a/beta-catenin signalling pathways. *J Cell Mol Med*, doi:10.1111/jcmm.14518 (2019).

Wieckowska, A. et al. Increased hepatic and circulating interleukin-6 levels in human nonalcoholic steatohepatitis. *Am J Gastroenterol* 103, 1372-1379, doi:10.1111/j.1572-0241.2007.01774.x (2008).

Schwaller, J. et al. Stat5 is essential for the myelo- and lymphoproliferative disease induced by TEL/JAK2. *Mol Cell* 6, 693-704 (2000).

Tsai, J. M. et al. Surgical adhesions in mice are derived from mesothelial cells and can be targeted by antibodies against mesothelial markers. *Sci Transl Med* 10, doi:10.1126/scitranslmed.aan6735 (2018).

Rinkevich, Y. et al. Skin fibrosis. Identification and isolation of a dermal lineage with intrinsic fibrogenic potential. *Science* 348, aaa2151, doi:10.1126/science.aaa2151 (2015).

Ransom, R. C. et al. Genetic dissection of clonal lineage relationships with hydroxytamoxifen liposomes. *Nat Commun* 9, 2971, doi:10.1038/s41467-018-05436-6 (2018).

Ueno, H. & Weissman, I. L. Clonal analysis of mouse development reveals a polyclonal origin for yolk sac blood islands. *Dev Cell* 1, 519-533, doi:10.1016/j.devcel.2006.08.001 (2006).

Schulien, I. et al. The transcription factor c-Jun/AP-1 promotes liver fibrosis during nonalcoholic steatohepatitis by regulating Osteopontin expression. *Cell Death Differ* 26, 1688-1699, doi:10.1038/s41418-018-0239-8 (2019).

Bridges, R. S. et al. Gene expression profiling of pulmonary fibrosis identifies Twist1 as an antiapoptotic molecular "rectifier" of growth factor signaling. *Am J Pathol* 175, 2351-2361, doi:10.2353/ajpath.2009.080954 (2009).

Vuga, L. J. et al. Cartilage oligomeric matrix protein in idiopathic pulmonary fibrosis. *PLoS One* 8, e83120, doi:10.1371/journal.pone.0083120 (2013).

Ichihara, S. et al. Ablation of aryl hydrocarbon receptor promotes angiotensin II-induced cardiac fibrosis through enhanced c-Jun/HIF-1alpha signaling. *Arch Toxicol* 93, 1543-1553, doi:10.1007/s00204-019-02446-1 (2019).

Schulz, J. N. et al. COMP-assisted collagen secretion—a novel intracellular function required for fibrosis. *J Cell Sci* 129, 706-716, doi:10.1242/jcs.180216 (2016).

Gulati, G. S. et al. Single-cell transcriptional diversity is a hallmark of developmental potential. *Science* 367, 405-411, doi:10.1126/science.aax0249 (2020).

Trapnell, C. et al. The dynamics and regulators of cell fate decisions are revealed by pseudotemporal ordering of single cells. *Nat Biotechnol* 32, 381-386, doi:10.1038/nbt.2859 (2014).

Ye, N., Ding, Y., Wild, C., Shen, Q. & Zhou, J. Small molecule inhibitors targeting activator protein 1 (AP-1). *J Med Chem* 57, 6930-6948, doi:10.1021/jm5004733 (2014).

Schuringa, J. J., Timmer, H., Luttickhuizen, D., Vellenga, E. & Kruijer, W. c-Jun and c-Fos cooperate with STAT3 in IL-6-induced transactivation of the IL-6 response element (IRE). *Cytokine* 14, 78-87, doi:10.1006/cyto.2001.0856 (2001).

Wong, V. W. et al. Focal adhesion kinase links mechanical force to skin fibrosis via inflammatory signaling. *Nat Med* 18, 148-152, doi:10.1038/nm.2574 (2011).

Wilson, D. H. et al. Non-canonical Wnt signalling regulates scarring in biliary disease via the planar cell polarity receptors. *Nat Commun* 11, 445, doi:10.1038/s41467-020-14283-3 (2020).

Linsky, C. B. et al. Adhesion reduction in the rabbit uterine horn model using an absorbable barrier, TC-7. *J Reprod Med* 32, 17-20 (1987).

Ransom, R. C. et al. Genetic dissection of clonal lineage relationships with hydroxytamoxifen liposomes. *Nat Commun* 9, 2971, doi:10.1038/s41467-018-05436-6 (2018).

Muzumdar, M. D., Tasic, B., Miyamichi, K., Li, L. & Luo, L. A global double-fluorescent Cre reporter mouse. *Genesis* 45, 593-605, doi:10.1002/dvg.20335 (2007).

Kamran, P. et al. Parabiosis in mice: a detailed protocol. *J Vis Exp*, doi:10.3791/50556 (2013).

Hu, M. S. et al. Gene expression in fetal murine keratinocytes and fibroblasts. *J Surg Res* 190, 344-357, doi:10.1016/j.jss.2014.02.030 (2014).

Patro, R., Duggal, G., Love, M. I., Irizarry, R. A. & Kingsford, C. Salmon provides fast and bias-aware quantification of transcript expression. *Nat Methods* 14, 417-419, doi:10.1038/nmeth.4197 (2017).

Soneson, C., Love, M. I. & Robinson, M. D. Differential analyses for RNA-seq: transcript level estimates improve gene-level inferences. *F1000Res* 4, 1521, doi:10.12688/f1000research.7563.2 (2015).

Love, M. I., Huber, W. & Anders, S. Moderated estimation of fold change and dispersion for RNA-seq data with DESeq2. Genome Bio/15, 550, doi:10.1186/s13059-014-0550-8 (2014).

Subramanian, A. et al. Gene set enrichment analysis: a knowledge-based approach for interpreting genome-wide expression profiles. *Proc Natl Acad Sci USA* 102, 15545-15550, doi:10.1073/pnas.0506580102 (2005).

Yu, G., Wang, L. G., Han, Y. & He, Q. Y. clusterProfiler: an R package for comparing biological themes among gene clusters. *OMICS* 16, 284-287, doi:10.1089/omi.2011.0118 (2012).

Dobin, A. et al. STAR: ultrafast universal RNA-seq aligner. *Bioinformatics* 29, 15-21, doi:10.1093/bioinformatics/bts635 (2013).

Stuart, T. et al. Comprehensive Integration of Single-Cell Data. *Cell* 177, 1888-1902 e1821, doi:10.1016/j.cell.2019.05.031 (2019).

Becht, E. et al. Dimensionality reduction for visualizing single-cell data using UMAP. *Nat Biotechnol*, doi:10.1038/nbt.4314 (2018).

Clark, N. R. et al. The characteristic direction: a geometrical approach to identify differentially expressed genes. *BMC Bioinformatics* 15, 79, doi:10.1186/1471-2105-15-79 (2014).

Chen, E. Y. et al. Enrichr: interactive and collaborative HTML5 gene list enrichment analysis tool. *BMC Bioinformatics* 14, 128, doi:10.1186/1471-2105-14-128 (2013).

Abudayyeh, O. O. et al. C2c2 is a single-component programmable RNA-guided RNA targeting CRISPR effector. *Science* 353, aaf5573, doi:10.1126/science.aaf5573 (2016).

Ran, F. A. et al. Genome engineering using the CRISPR-Cas9 system. *Nat Protoc* 8, 2281-2308, doi:10.1038/nprot.2013.143 (2013).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject to reduce adhesion formation or to reduce already-formed adhesions, the method comprising:

administering topically to abdominal cavity of an abdominal surgery patient thereof an effective dose of a small molecule inhibitor of the Activator Protein 1 (AP-1) transcription factor complex, wherein the small molecule inhibitor is T-5224 (3-[5-(4-Cyclopentyloxy-2-hydroxybenzoyl)-2-[(3-oxo-1,2-benzoxazol-6-yl) methoxy phenyl]propanoic acid).

2. The method of claim 1, wherein the inhibitor is administered prior to a surgical procedure performed on the subject.

3. The method of claim 1, wherein the inhibitor is administered after a surgical procedure performed on the subject.

4. The method of claim 1, wherein the inhibitor is formulated in a particulate form.

5. The method of claim 4, wherein the particulate form is a PLGA microparticle.

6. The method of claim 1, wherein the inhibitor is administered in a drug delivery device.

7. The method of claim 4, wherein the drug delivery device is a biodegradable matrix.

8. The method of claim 5, wherein the matrix is a hydrogel.

9. A method of treating a subject to reduce adhesion formation or to reduce already-formed adhesions, the method comprising:

administering topically to a surgical site or cavity of a subject in need thereof an effective dose of a small molecule inhibitor of the Activator Protein 1 (AP-1) transcription factor complex, wherein the small molecule inhibitor is T-5224 (3-[5-(4-Cyclopentyloxy-2-hydroxybenzoyl)-2-[(3-oxo-1,2-benzoxazol-6-yl) methoxy]phenyl]propanoic acid).

10. A method of treating a subject to reduce adhesion formation or to reduce already-formed adhesions, the method comprising:

administering topically to the abdominal cavity of a subject in need thereof an effective dose of a small molecule inhibitor of the Activator Protein 1 (AP-1) transcription factor complex, wherein the small molecule inhibitor is T-5224 (3-[5-(4-Cyclopentyloxy-2-hydroxybenzoyl)-2-[(3-oxo-1,2-benzoxazol-6-yl) methoxy]phenyl]propanoic acid).

* * * * *